(12) United States Patent
Fogg et al.

(10) Patent No.: US 7,094,898 B2
(45) Date of Patent: Aug. 22, 2006

(54) RUTHENIUM COMPOUNDS, THEIR PRODUCTION AND USE

(75) Inventors: Deryn Elizabeth Fogg, Ottawa (CA); Jay Christopher Conrad, Ottawa (CA)

(73) Assignee: University of Ottawa, Ottawa (CA)

( * ) Notice: Subject to any disclaimer, the term of this patent is extended or adjusted under 35 U.S.C. 154(b) by 194 days.

(21) Appl. No.: 10/855,485

(22) Filed: May 28, 2004

(65) Prior Publication Data

US 2005/0131233 A1    Jun. 16, 2005

Related U.S. Application Data

(60) Provisional application No. 60/549,927, filed on Mar. 5, 2004, provisional application No. 60/490,534, filed on Jul. 29, 2003, provisional application No. 60/473,885, filed on May 29, 2003.

(51) Int. Cl.
| | |
|---|---|
| C07F 15/00 | (2006.01) |
| C07F 9/02 | (2006.01) |
| B01J 31/00 | (2006.01) |
| C07C 6/04 | (2006.01) |

(52) U.S. Cl. ............................ 546/4; 548/103; 556/21; 556/23; 556/136; 556/137; 585/511; 585/643; 585/940; 502/152

(58) Field of Classification Search .................... 546/4; 548/103; 556/21, 23, 136, 137; 585/511, 585/643, 940; 502/152
See application file for complete search history.

(56) References Cited

U.S. PATENT DOCUMENTS

| | | | |
|---|---|---|---|
| 5,312,940 A | 5/1994 | Grubbs et al. | 556/136 |
| 5,342,909 A | 8/1994 | Grubbs et al. | 526/171 |
| 5,710,298 A | 1/1998 | Grubbs et al. | 556/22 |
| 5,728,917 A | 3/1998 | Grubbs et al. | 585/653 |
| 5,750,815 A | 5/1998 | Grubbs et al. | 585/511 |
| 5,849,851 A | 12/1998 | Grubbs et al. | 526/93 |
| 5,880,231 A | 3/1999 | Grubbs et al. | 526/171 |
| 5,922,863 A | 7/1999 | Grubbs et al. | 540/538 |
| 5,959,170 A | 9/1999 | Withers, Jr. | 585/500 |
| 5,969,170 A | 10/1999 | Grubbs et al. | 556/21 |
| 6,111,121 A | 8/2000 | Grubbs et al. | 556/21 |
| 6,121,473 A | 9/2000 | Schrock et al. | 556/57 |
| 6,346,652 B1 | 2/2002 | Schrock et al. | 585/643 |
| 6,486,263 B1 | 11/2002 | Fogg et al. | 525/338 |
| 6,500,975 B1 | 12/2002 | Schwab et al. | 556/22 |
| 6,515,084 B1 | 2/2003 | Grubbs et al. | 526/90 |
| 6,590,048 B1 | 7/2003 | Furstner et al. | 526/171 |
| 6,610,626 B1 | 8/2003 | Grubbs et al. | 502/155 |
| 6,624,265 B1 | 9/2003 | Grubbs et al. | 526/135 |
| 6,635,768 B1 | 10/2003 | Herrmann et al. | 548/101 |
| 2002/0058812 A1 | 5/2002 | Grubbs et al. | 546/2 |

(Continued)

FOREIGN PATENT DOCUMENTS

WO    WO96/04289    7/1995

(Continued)

OTHER PUBLICATIONS

U.S. Appl. No. 08/282826, filed Jul. 29, 1994, Grubbs et al.

(Continued)

*Primary Examiner*—Porfirio Nazario-Gonzalez

(57) ABSTRACT

A new class of compounds is disclosed that in preferred embodiments relate to Ru-based catalysts suitable for use in olefin metathesis reactions. Such compounds demonstrate high rates of catalytic turnover in comparison with other Ru catalysts known in the art. Moreover, the catalysts are highly stable, and readily suited to attachment to a solid support via the anionic ligands. The invention also pertains to methods of producing the catalysts, and their use in catalyzing olefin metathesis reactions.

32 Claims, 9 Drawing Sheets

Chart 1.

Scheme 1.

Scheme 2.

U.S. PATENT DOCUMENTS

| | | | |
|---|---|---|---|
| 2003/0055262 A1 | 3/2003 | Grubbs et al. | 548/103 |
| 2003/0069374 A1 | 4/2003 | Grubbs et al. | 526/171 |
| 2003/0083445 A1 | 5/2003 | Grubbs et al. | 526/161 |
| 2003/0100776 A1 | 5/2003 | Grubbs et al. | 549/513 |
| 2003/0181609 A1 | 9/2003 | Grubbs et al. | 526/171 |
| 2003/0195357 A1 | 10/2003 | Stuer et al. | 546/2 |
| 2003/0236427 A1 | 12/2003 | Grubbs et al. | 558/238 |
| 2004/0210055 A1 | 10/2004 | Nolan et al. | 546/2 |

FOREIGN PATENT DOCUMENTS

| | | |
|---|---|---|
| WO | WO 00/71554 | 11/2000 |

OTHER PUBLICATIONS

U.S. Appl. No. 08/282827, filed Jul. 29, 1994, Grubbs et al.

Amoroso et al., "An Attractive Route to Olefin Methathesis Catalysts: Facile Synthesis of a Ruthenium Alkylidene Complex Containing Labile Phosphane Donors", *Adv. Synth. Catal.* 2002, 344, 757-763.

Arduengo et al., "Electronic Stabilization of Nucleophilic Carbenes", *J. Am. Chem. Soc.* 1992, 114, 5530-5534.

Braddock, D.C. and Wildsmith, A.J., "On the use of tandem allylic acetate isomerisation and ringclosing metathesis with palladium(0) phophine complexes and ruthenium benzylidenes as orthogonal catalysts", *Tetrahedron Letters*, 42(2001), 3239-3242.

Buchmeiser, M.R., "Homogeneous Metathesis Polymerization by Well-Defined Group VI and Group VIII Transition-Metal Alkylidenese: Fundamentals and Applications in the Preparation of Advanced Materials", *Chem. Rev.* 2000, 100, 1565-1604.

Buchowicz et al., "A novel ruthenium carbine dimmer that is active in the metathesis of internal alkenes; the crystal structure of $Ru_2(=CHPh)_2(CF_3CO_2)_2(\mu-CF_3CO_2)_2(PCy_3)_2(\mu-H_2O)$", *Journal of Organometallic Chemistry*, 1999, 588, 205-210.

Buchowicz et al., "Novel Ruthenium (II)$_2$ Carboxylates as Catalysts for Alkene Metathesis", *Chem. Eur. J.* 2001, 7, No. 13, 2842-2847.

Chang et al., "Synthesis and Characterization of New Ruthenium-Based Olefin Metathesis Catalysts Coordinated with Bidentate Schiff-Base Ligands", *Organometallics*, 1998, 17, 3460-3465.

Coalter et al., "R-Group reversal of isomer stability for $RuH(X)L_2(CCHR)$ vs. $Ru(X)L_2(CCH_2R)$: access to four-coordinate ruthenium carbenes and carbynes", *New J. Chem.* 2000, 24, 925-927.

Coalter et al., "Carbene transposition involving double dehydrogenation of an $sp^3$ carbon", *Chem. Commun.*, 2001, 1158-1159.

Connon, S.J. and Blechert, S., "Recent Developments in Olefin Cross-Metathesis", *Angew. Chem. Int. Ed.*, 2003, 42, 1900-1923.

Conrad et al., "The First Highly Active, Halide-Free Ruthenium Catalyst for Olefin Metathesis", *Organometallics*, 2003, 22, 3634-3636.

Conrad et al., "Concise Route to Highly Reactive Ruthenium Metathesis Catalysts Containing a Labile Donor and an N-Heterocyclic Carbene (NHC) Ligand", *Organometallics* 2003, 22, 1986-1988.

De Clerq, B. and Verport, F., "Assessing the Scope of the Introduction of Schiff Bases as Co-Ligands for Monometallic and Homobimetallic Ruthenium Ring-Opening Metathesis Polymerisation and Ring-Closing Metathesis Initiators", *Adv. Syn. Catal.* 2002, 344, 639-648.

De Clerq, B. and Verport, F., "Activity of a New Class of Ruthenium Based Ring-Closing Metathesis and Ring-Opening Metathesis Polymerization Catalysts Coordinated with a 1,3-Dimesityl-4,5-Dihydroimidazol-2-Ylidene and a Schiff Base Ligand", *Tetrahedron Letters* 43 (2002) 9101-9104.

Dias, E.L. and Grubbs, R.H., "Synthesis and Investigation of Homo- and Heterobimetallic Ruthenium Olefin Metathesis Catalysts Exhibiting Increased Activities", *Organometallics* 1998, 17, 2758-2767.

Dinger, M.B. amd Mol, J.C., "High Turnover Numbers with Ruthenium-Based Metathesis Catalysts", *Adv. Synth. Catal.* 2002, 344, 671-677.

Fürstner, A., "Olefin Metathesis and Beyond", *Angew. Chem. Int. Ed.*, 2000, 39, 3012-3043.

Fürstner, A. and Ackermann, L., "A most user-friendly protocol for ring closing metathesis reactions", *Chem. Commun.* 1999, 95-96.

Fürstner, A. and Langermann; K., "Conformationally Unbiased Macrocyclization Reactions by Ring Closing Metathesis", *J. Org. Chem.* 1 996, 61:3942-3943.

Fürstner et al., "Ruthenium Carbene Complexes with N,N Bismesityl)imidazol-2-ylidene Ligands: RCM Catalysts of Extended Scope", *J. Org. Chem.* 2000, 65, 2204-2207.

Fürstner et al., "Alkyne Metathesis: Development of a Novel Molybdenum-Based Catalyst System and its Application to the Total Synthesis of Epothilone A and C", *Chem. Eur. J.* 2001, 7, No. 24, 5299-5317.

Hoveyda, A.H. and Schrock, R.R., "Catalytic Asymmetric Olefin Metathesis", *Chem. Eur. J.* 2001, 7, 945-950.

Hoveyda et al., "Ru complexes bearing bidentate carbens: from innocent curiosity to uniquely effective catlysts for olefin metathesis", *Org. Biomol. Chem.*, 2004, 2, 8-23.

Huang et al., "Influence of Sterically Demanding Carbene Ligation on Catalytic Behavior and Thermal Stability of Ruthenium Olefin Metathesis Catalysts", *Organometallics* 1999, 18, 5375-5380.

Huang et al., "Olefin Metathesis-Active Ruthenium Complexes Bearing a Nucleophilic Carbene Ligand", *J. Am. Chem. Soc.* 1999, 121, 2674-2678.

Jung et al. "A Series of Vinylidene-, Yinyl, Carbene- and Carbyneruthenium(II) Complexes with $[Ru(PCy_3)_2$ ]as Molecular Building Blocks", *Eur. J. Inorg. Chem.* 2004, 469-480.

Krause et al., "Synthesis and Reactivity of Homogenous and Heterogeneous Ruthenium-Based Metathesis Catalysts Containing Electron-Withdrawing Ligands", *Chem. Eur. J.*, 2004, 10, 777-784.

Krause et al., "Monolithic Polymer Supports for Heterogenized Metatheses Catalysts," *Polymer Reprints* 2003, 44(1) 790 & 791.

McConville et al., "Synthesis of Chiral Molybdenum ROMP Initiators and All-Cis Highly Tactic $Poly(2,3-(R)_2$ norbornadiene)(R= $CF_3$ or $CO_2Me$)", *J. Am. Chem. Soc.* 1993, 115, 4413-4414.

Optstal et al., "Synthesis of Highly Active Ruthenium Indenylidene Complexes for Atom-Transfer Radical Polymerization and Ring-Opening Metathesis Polymerization", Agnew. Chem. Int. Ed. 2003, 42, 2876-2879.

Opstal et al., "Easily Accessible Ring Opening Metathesis and Atom Transfer Radical Polymerization Catalysts based on Arene, Norbonadiene and Cyclooctadiene Ruthenium Complexes Bearing Schiff Base Ligands", *Adv. Synth. Catal.* 2003, 345, No. 3, 393-401.

Prüths et al., "Preparation, Reactivity, and Structural Peculiarities of Hydroxyalkyl-Funtionalized Second-Generation Ruthenium Carbene Carbene Complexes", *Organometallics* 2004, 23, 280-287.

Sanford et al., "Mechanism and Activity of Ruthenium Olefin Metathesis Catalysts", *J. Am. Chem. Soc.* 2001, 123, 6543-6554.

Sanford et al., "A Versatile Precursor for the Synthesis of New Ruthenium Olefin Metathesis Catalysts", *Organometallics* 2001, 20, 5314-5318.

Sanford et al., "Synthesis and Reactivity of Neutral and Cationic Rutheium (II) Tris(pyrazolyl)borate Alkylidenes", *Organometallics* 1998, 17, 5384-5389.

Sanford et al., "Ruthenium-Based Four-Coordinte Olefin Metathesis Catalysts", *Agnew. Chem. Int. Ed.* 2000, 39, 3451-3453.

Schmidt et al., "Ring-Closing Olefin Metathesis and Radical Cyclization as Competing Pathways", *J. Org. Chem.* 2004, 69, 1421-1424.

Scholl et al., "Synthesis and Activity of a New Generation of Ruthenium-Based Olefin Metathesis Catalysts Coordinated with 1,3-Dimesity-4,5-dihydroimidazol-2-ylidene Ligands", *Org. Lett.*, vol. 1, No. 6, 1999, 953-956.

Schrock, R.R., "Olefin Methatsis by Molybdenum Imido Alkylidene Catalysts", *Tetrahedron* 55, 1999, 8141-8153.

Schurer et al., "Synthesis and Application of a Permanently Immobilized Olefin-Metathesis Catalyst", *Angew. Chem. Int. Ed.*, 2000, 39,3898-3901.

Totland et al., "Ring Opening Metathesis Polymerization with Binaphtholate or Biphenolate Complexes of Molybdenum", *Macromolecules* 1996, 29, 6114-6125.

Trnka, T.M. and Grubbs, R.H., "The Development of $L_2X_2Ru=CHR$ Olefin Metathesis Catalysts: An Organometallic Success Story", *Acc. Chem. Res.* 2001, 34, 18-29.

Tsang et al., "Alkylidene and Metalacyclic Complexes of Tungsten that Contain a Chiral Biphenoxide Ligands Synthesis, Asymmetric Ring-Closing Metathesis, and Mechanistic Investigations", *J. Am. Chem. Soc.* 2003, 125, 2652-2666.

Ulman, M. and Grubbs, R.H., "Ruthenium Carbene-Based Olefin Metathesis Initiators: Catalyst Decomposition and Longevity", *J. Org. Chem.* 1999, 64, 7202-7207.

Van Veldhuizen et al., "A Recyclable Chiral Ru Catalyst for Enantioselective Olefin Metathesis Efficient Catalytic Asymmetric Ring-Opening/Cross Metathesis in Air", *J. Am. Chem. Soc.* 2002, 124, 4954-4955.

Van Veldhuizen et al., "Chiral Ru-Based Complexes for Aysmmetric Olefin Metathesis: Ehancement of Catalyst Activity through Steric and Electronic Modifications", *J. Am. Chem. Soc.* 2003, 125, 12502-12508.

Volland et al., "An 'Old Hydridre' in a new synthesis: a convenient approach to Grubbs-type carbene complexes $(PPh_3)_2aCl_2RU=CH-CH=CR_2$ and their hexacoordinate acetonitrile adducts", *J. Organometallic Chemistry*, 2002, 641, 220-226.

Werner et al. "Synthesis and Reactions of Stable 16-Electron Osmium (0) Complexes [OsCl(NO)(PR$_3$)]Including the X-ray Crystal Structure of [OsCl2(NO) ($\eta^1$ -CH=CPh$_2$)Pi-Pr$_3$]$_2$", Organometallics, vol. 14, 1995, 612-618.

Weskamp et al. "Highly Active Ruthenium Catalysts for Olefin Metathesis: The Synergy of N-Heterocyclic Carbenes and coordinatively Labile Ligands" *Angew. Chem. Int. Ed.* 1999, 38, 2416-2419.

Wu et al., "Reactions of Ruthenium Carbenes of the Type $(PPh_3)_2Ru=CH-CH=CPh_2$ (X=Cl and $CF_3COO$) with Strained Acyclic Olefins and Functionalized Olefins", *J. Am Chem. Soc.* 1995, 117, 5503-5511.

Catalyst Design in Olefin Metathesis and Tandem Catalysis, Yale (Dec. 4, 2003).

Catalyst Design in Olefin Metathesis DSM Tandem Catalysis New Orleans (Nov. 21, 2003). :

Catalyst Design in Olefin Metathesis and Tandem Catalysis Milwaukee (Mar. 8, 2003).

Ru-Alkylidene and Alkylidyne Complexes of Electron-Deficient Phenoxides, American Chemical Society Meeting, New Orleans (Mar. 27, 2003.

Catalyst Design in Olefin Metathesis, Mt. Allison University, Sackville, New Brunswick (Mar. 3, 2004).

Catalyst Design in Olefin Metathesis DSM Pharma, Netherlands (Mar. 11, 2004).

Catalyst Design in Olefin Metathesis, Queen's University, Kingston, Ontario (Nov. 26, 2004).

Catalyst Design in Olefin Metatheisis, XII National Brazilian Meeting on Organic Chemistry , Sao Carlos, Brazil (Sep. 11, 2004).

Symposium on Late Materials in Catalysis, 87th CSC. London, Ontario (May 29-Jun. 1, 2004).

14th International Symposium on Homogenous Catalysis, Munich , Germany (Jul. 5-9, 2004).

36th International Congress on Coordination Chemistry, Merida, Mexico (Jul. 18-23, , 2004).

Chart 1.

Scheme 1.

Scheme 2.

4c

5

RUTHENIUM COMPOUNDS, THEIR PRODUCTION AND USE

CROSS REFERENCE TO RELATED APPLICATIONS

This application is related to commonly owned co-pending provisional patent applications Ser. Nos. 60/473,885 filed May 29, 2003, 60/490,534 filed Jul. 29, 2003, and 60/549,927 filed Mar. 5, 2004, and claims the benefit of these earlier filing dates.

FIELD OF THE INVENTION

The present invention relates to ruthenium and osmium coordination compounds. In particular, the present invention relates to metal alkylidene complex compounds, having high stability and high rates of catalytic turnover for olefin metathesis reactions.

BACKGROUND TO THE INVENTION

Transition-metal catalyzed C—C bond modulation via olefin metathesis is of considerable interest and synthetic utility. Initial studies in this area were based on catalytically active mixtures consisting of transition-metal chlorides, oxides or oxychlorides, cocatalysts such as $EtAlCl_2$ or $R_4Sn$, and promoters including $O_2$, EtOH or PhOH. These systems catalyze olefin metathesis reactions, however their catalytic centers are ill-defined and systematic control of their catalytic activity is not possible.

Recent efforts have been directed towards the development of well-defined metathesis active catalysts based on transition metal complexes. The results of research efforts during the past two decades have enabled an in-depth understanding of the olefin metathesis reaction as catalyzed by transition metal complexes.

Group VIII transition metal olefin metathesis catalysts, specifically ruthenium and osmium alkylidene complexes, have been described in U.S. Pat. Nos. 5,312,940 and 5,342,909 and U.S. patent applications Ser. Nos. 08/282,826 and 08/282,827, all of which are incorporated herein by reference. The ruthenium and osmium alkylidene complexes disclosed in these patents and applications are of the general formula:

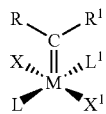

wherein M is ruthenium or osmium, X and $X^1$ are anionic ligands, and L and $L^1$ are neutral electron donors.

U.S. Pat. Nos. 5,312,940 and 5,342,909 disclose specific vinyl alkylidene ruthenium and osmium complexes and their use in catalyzing the ring opening metathesis polymerization ("ROMP") of strained olefins. In all of the specific alkylidene complexes disclosed in these patents, $R^1$ is hydrogen and R is either a substituted or unsubstituted vinyl group.

U.S. patent application Ser. Nos. 08/282,826 and 08/282,827 disclose specific vinyl alkylidene ruthenium and osmium complexes and their use in catalyzing a variety of metathesis reactions. The catalysts disclosed in these applications have specific neutral electron donor ligands L and $L^1$; namely, phosphines in which at least one substituent is a secondary-alkyl or cycloalkyl group. In all of the specific alkylidene complexes disclosed in the patent applications, $R^1$ is hydrogen and R is either a substituted or unsubstituted vinyl group.

In another example, U.S. Pat. No. 5,959,170, issued Oct. 19, 1999, discloses similar ruthenium or osmium catalysts, wherein L and $L^1$ are each trialkyl phosphine ligands, where at least one of the alkyl groups on the phosphine is a secondary alkyl or cycloalkyl. The catalysts are suitable for catalyzing an array of metathesis reactions including ring-opening metathesis polymerization of cyclic olefins, ring closing metathesis of acyclic dienes, cross metathesis involving at least one acyclic or unstrained cyclic olefin, depolymerization of unsaturated polymers and synthesis of telechetic polymers.

In another example, U.S. Pat. No. 6,111,121, issued Aug. 29, 2000, reported novel ruthenium alkylidene compounds that are stable in the presence of a variety of functional groups and can be used to catalyze olefin metathesis reactions on unstrained cyclic and acyclic olefins. The alkylidene compounds disclosed comprise a compound of Formula I, wherein M is Os or Ru; $R^1$ is hydrogen; R is selected from the group consisting of hydrogen, substituted or unsubstituted alkyl, and substituted or unsubstituted aryl; X and $X^1$ are independently selected from any anionic ligand; and L and $L^1$ are independently selected from any neutral electron donor. The compounds are suitable for use in ROMP and ring closing metathesis reactions.

In further examples, U.S. Pat. Nos. 6,121,473, and 6,346,652, issued Sep. 19, 2000 and Feb. 12, 2002 respectively, disclose compositions and methods generally involving molybdenum or tungsten-based catalysts of the general formula (II):

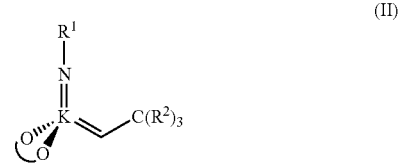

wherein K is preferably Mo or W, $R^1$ and $R^2$ each independently selected from $C_1$–$C_{12}$ alkyl, heteroalkyl, aryl, heteroaryl and adamantyl, and the linked oxygen atoms pertaining to a chiral dialkoxide. The compositions are suitable for use as catalysts for ring-closing metathesis reactions involving racemic dienes, in which enantiomeric cyclic olefin products are generated. Methods are also provided for catalytic enantioselective desymmetrization.

The teachings of U.S. Pat. Nos. 5,959,170, 6,111,121, 6,121,473, and 6,346,652 are also incorporated herein by reference.

In a final example, International Patent publication WO00/71554, published Nov. 30, 2000 discloses ruthenium or osmium based metathesis catalysts that include an alkylidene group and an imidazolidine-based ligand. The inclusion of the imidazolidine ligand to the previously described ruthenium or osmium catalysts provides some improvements to the properties of these complexes. The imidazolidine ligand maintains the functional group tolerance of the previously described ruthenium complexes, and enhances metathesis activity.

Over the past decade, olefin metathesis has emerged as a powerful synthetic tool. For example, ring-closing metathesis (RCM) reactions and cross-metathesis reactions have had a major impact in organic synthesis, including natural products synthesis, (Ref. 1a–1c) while metathesis polymerization techniques have given access to a new class of polymer materials (Ref. 1d). Grubbs' development of robust, functional group-tolerant catalysts based on ruthenium (Ref. 1a) was a milestone in the still ongoing evolution of this methodology (see compound of Formula Ia, FIG. 1). Considerable current effort is directed at discovery of new Ru catalysts with expanded activity, selectivity, and lifetime (an important recent addition being highly reactive N-heterocyclic carbene (NHC) derivatives; Ref. 2–4, 5a, for example see compounds of Formula 1b–1e, as shown in FIG. 1). While exchange of the neutral "L-donor" ligands in these systems is now facile, Ref. 2,5 the steric and electronic consequences are frequently dramatic. Fine tuning of activity and selectivity has remained elusive. In contrast, the Group 6 catalysts pioneered by Schrock afford exceptional control over activity and selectivity, including asymmetric ring-closing and ring-opening metathesis. (Ref. 1c, 6–8) Key to this versatility is the presence of modular, tunable aryloxide or alkoxide ligands, vs. the simple chloride ligands ubiquitous (Ref. 9–12) in the Ru chemistry.

While much effort has focused on modification of neutral "L-donor" ligands in the ruthenium systems (as noted above), modification of the anionic ligands is much less explored, and has so far met with limited success. Metathesis catalysts of low to moderate activity are obtained by replacing chloride with carboxylate (Ref. 9a, b, c): or by the use of heterobifunctional salicylaldimine (Ref. 9d), or NHC-naphtholate ligands (Ref. 10). Installation of alkoxide ligands affords four-coordinate species 2a/b (see FIG. 1, Scheme 1), (Ref. 11,12). Despite the nominal coordinative unsaturation of these complexes, they exhibit near-zero metathesis activity (Ref. 12; Table 1). Reaction of compound 1a or $RuCl_2(P^iPr_3)_2(CHPh)$ with phenoxide anion gives alkylidynes (compounds 4a and 4b), via deprotonation of the benzylidene ligand. (Ref. 11)

There remains a continuing need to develop improved catalysts for olefin metathesis reactions, including, but not limited to, ring-opening metathesis polymerization, ring closing metathesis, cross-metathesis reactions (for example involving at least one acyclic or unstrained cyclic olefin), and depolymerization of olefin polymers.

SUMMARY OF THE INVENTION

It is an object of the present invention, at least in preferred embodiments, to provide an olefin metathesis catalyst having a high rate of catalytic turnover.

It is another object of the invention, at least in preferred embodiments, to provide an olefin metathesis catalyst having a high degree of stability.

It is another object of the present invention, at least in preferred embodiments, to provide an improved method of olefin metathesis.

It is another object of the present invention, at least in preferred embodiments, to provide an olefin metathesis catalyst that is suitable for enabling the production of stereospecific products, including enantiospecificity and E/Z selectivity.

It is another object of the present invention, at least in preferred embodiments, to provide an olefin metathesis catalyst that is catalytically active whilst remaining bound to a solid support.

The inventors have discovered that selectivity of Ruthenium alkylidine catalysts for alkylidene or alkylidyne products in the exchange reaction with alkoxides/aryloxides and other compounds is likely controlled by steric matching or mismatching between incoming pseudohalide and ancilliary donor ligands. Importantly, the inventors have demonstrated this by selective synthesis of four-coordinate alkylidene or five coordinate alkylidene complexes. The five-coordinate alkylidene complexes can function as olefin metathesis catalysts having strikingly high catalytic turnover rates. Moreover, the novel catalysts present additional advantages including high stability, and at least in preferred embodiments a capacity to generate stereospecific product enantiomers. Furthermore the catalysts, at least in preferred embodiments, can be readily and permanently fixed to a solid support for improved industrial application, and catalyst purification.

In one aspect, the present invention provides for a compound of the formula Ia or Ib:

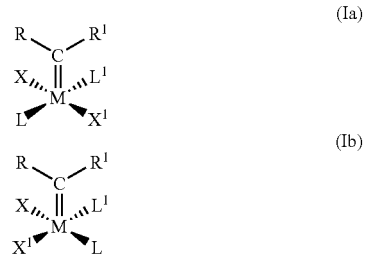

wherein:

M is selected from the group consisting of Ru and Os;

R and $R^1$ are independently selected from the group consisting of hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl; each optionally substituted with one or more $C_1$–$C_5$ alkyl, halogen, $C_1$–$C_5$ alkoxy, phenyl optionally substituted with halogen, $C_1$–$C_5$ alkyl, or $C_1$–$C_5$ alkoxy;

X and $X^1$ are anionic ligands, wherein X and $X^1$ are each independently selected from -Z-Q, or wherein one of X and $X^1$ is halide and the other of X and $X^1$ is -Z-Q, each Z comprising O, S, N, or C, and each Q comprising a planar electron withdrawing group; and L and $L^1$ are independently selected from any neutral electron donor; wherein any 2–3 of X, $X^1$, L, or $L^1$ are optionally covalently linked to form a chelating multidentate ligand.

Preferably, each Q is a $C_3$–$C_{20}$ heterocyclic or aromatic cyclic, bicyclic, or multicyclic ring system that is unsubstituted or substituted with 1–20 electron-withdrawing groups and/or one or more $C_1$–$C_{10}$ alkyl groups.

Preferably, each Z is S and each Q is CN.

Preferably the electron-withdrawing group or groups with respect to Q are each independently selected from the group consisting of $NO_2$, $CF_3$, halide, ester, and ketone groups. Preferably, at least one Q is a 6-carbon ring substituted in at least one position by a halide atom. More preferably at least one Q is selected from $C_6F_5$, $C_6Cl_5$, and $C_6Br_5$. Most preferably at least one of X and $X^1$ is $OC_6Br_5$.

In another aspect, X and $X^1$ are preferably linked to form a multidentate chelating ligand. In this scenario, X and $X^1$ are preferably linked to form a diolate, biphenolate or binaphthalate group that is unsubstituted or substituted with at least one halide. More preferably, the biphenolate group is of the formula $O_2C_{12}F_8$ or its derivatives, especially ones containing substituents ortho to the oxygen atoms.

Preferably, one of L and $L^1$ in the compounds of formula I is selected from the group consisting of N,N'-bis(mesityl) imidazol-2-ylidene (IMes), N,N'-bis-(mesityl)-imidazolidine ($H_2$IMes), N,N'-bis($C_3$–$C_{12}$ aryl or $C_1$–$C_{12}$ alkyl)imidazolidine and N,N'-bis($C_1$–$C_{12}$ alkyl or $C_3$–$C_{12}$ aryl) imidazol-2-ylidene; and the other of L or $L^1$ is pyridine unsubstituted or substituted with one or more electron withdrawing groups. More preferably, the pyridine group is substituted in the 3-position by Br.

In specific preferred aspects, both X and $X^1$ comprise -Z-Q, wherein each Z is oxygen.

In another embodiment the present invention provides for a catalyst for catalyzing olefin metathesis reactions, the catalyst comprising a compound according to the present invention, wherein M is Ru. Preferably, the olefin metathesis reaction comprises a reaction selected from ring-closing metathesis, ring-opening metathesis and cross-metathesis.

In specific preferred aspects, the catalyst is capable of generating stereospecific products.

Preferably, the catalyst is suitable for tethering to a solid support. More preferably the catalyst may be tethered through X, or $X^1$, or through both X and $X^1$. Most preferably the catalyst remains catalytically active without separation from the solid support. Most preferably, the solid support is selected from the group consisting of Sepharose™, glass beads, magnetic beads, and polystyrene.

Preferably, the catalyst remains active in fluorous reaction media.

In another aspect the present invention provides for a method for olefin metathesis, the method comprising the steps of exposing the olefin to a catalyst of the present invention, and purifying or partially purifying the products. Preferably, the olefin metathesis reaction is selected from ring-closing metathesis, ring opening metathesis, and cross-metathesis.

In another aspect the present invention provides for a method for producing a catalyst for olefin metathesis reactions, comprising the steps of:

providing a compound according to forumla I, wherein M is Ru, X and $X^1$ are halide, and each L a neutral ligand; reacting the compound with TlOY, wherein Y is a cyclic or bicyclic carbon-ring system comprising from 3 to 12 carbon atoms that are unsubstituted, or substituted with from 1 to 10 electron-withdrawing groups; and purifying or partially purifying the catalyst.

Preferably, X and $X^1$ are Cl, and one of L or $L^1$ is pyridine, optionally substituted with one or more electron withdrawing groups, and the other of L and $L^1$ is IMes.

In another aspect the present invention provides for a compound of formula III:

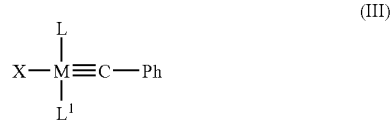

(III)

wherein M is Ru or Os;
X is an anionic ligand of the formula -Z-Q, wherein each Z is selected from the group consisting of unsubstituted or substituted O, S, N, or C and each Q comprising a planar electron withdrawing group; and L and $L^1$ are independently selected from any neutral electron donor; wherein any 2–3 of X, $X^1$, L, or $L^1$ are optionally covalently linked to form a chelating multidentate ligand.

Preferably, each Q is a $C_3$–$C_{20}$ heterocyclic or aromatic cyclic, bicyclic, or multicyclic ring system that is unsubstituted or substituted with 1–20 electron-withdrawing groups and/or one or more $C_1$–$C_{10}$ alkyl groups.

Preferably, each Z is S and each Q is CN.

Preferably, Q is a 6-carbon ring unsubstituted or substituted with one or more halide atoms. Preferably, Z is oxygen and Q is $C_6F_5$.

In another aspect the present invention provides for the use of a catalyst according to the present invention, for catalyzing an olefin metathesis reaction.

DETAILED DESCRIPTION OF THE INVENTION

Figure 1:
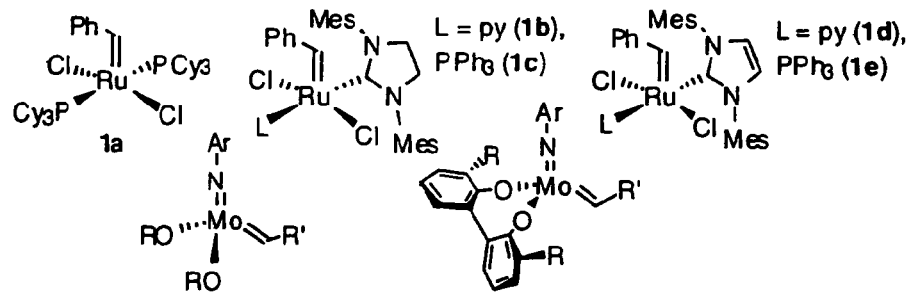
FIG. 1 provides a summary of Ru and Mo catalysts of the prior art (Chart 1), examples of transmetallation reactions of Grubbs-class Ru alkylidenes (Scheme 1), and methods for producing selected Ru compounds of the present invention (Scheme 2).
Figure 1:
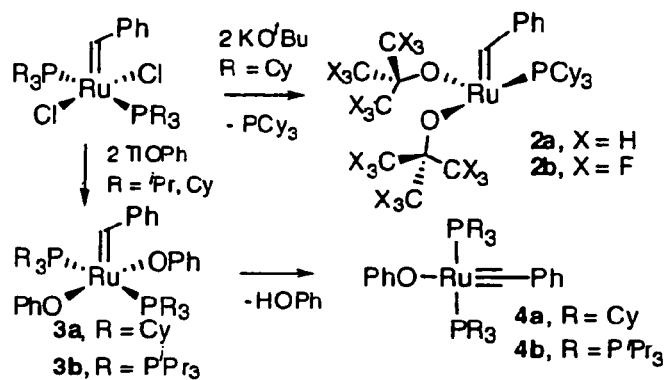
Figure 1:
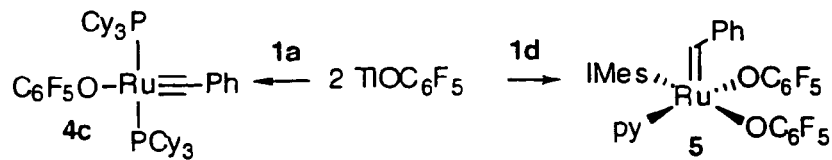

The present invention pertains to the development of a new class of Ru and Os compounds. Some of these compounds are useful as catalysts in olefin metathesis, and present significant advantages over other olefin metathesis catalysts that are known in the art.

In contrast to Ru catalysts, group 6 catalysts have limited utility in organic or industrial synthesis due to extreme sensitivity to deactivation upon exposure to air, water, and polar functional groups. Therefore, Ru systems present a significant advantage with regard to such sensitivity. Ru olefin metathesis catalysts generally comprise a Ru atom that is coordinated by several ligands, which often include a alkylidene group, as well as anionic and neutral ligands. Within Ru systems, ligand modification has previously focussed largely upon varying the neutral ligands (L, and $L^1$ in the compound of formula I), which has dramatic consequences for activity and selectivity. Fine-tuning of activity and selectivity by modulation of the anionic ligands has previously met with limited success. In general, most complexes obtained by attempted replacement of the anionic donors by phenoxides or alkoxides are not metathesis active or show low activity, owing either to steric congestion or to the formation of complexes without a metathesis active site.

The inventors have discovered that selectivity for alkylidene or alkylidyne products is likely controlled by steric matching/mismatching between incoming pseudohalide and ancillary donor ligands. Moreover, the inventors have demonstrated the successful application of this strategy to selective synthesis of either four-coordinate or five coordinate alkylidene complexes. Unexpectedly, the latter achieve strikingly high turnover number (for example over 40,000) in ring-closing metathesis (RCM) for diethyldiallylmalonate when used as a test substrate (see examples).

Importantly, the inventors have evidence that preferential pi-coordination of aryloxides is a common problem that prevents formation of the target complexes with a metathesis-capable active site. In accordance with the present invention, this problem has been circumvented using electron deficient ligands including, but not limited to, aryloxides, which preferentially coordinate as anionic donors through oxygen, rather than binding through the aromatic ring. The catalyst compounds of the present invention include Ru complexes that comprise any anionic ligands having a carbon ring system that coordinates Ru though a 'spacer atom', the spacer atom selected from the group including, but not limited to, oxygen, sulfur, nitrogen and carbon. The spacer atom may be unsubstituted or substituted. Most preferably the spacer atom is oxygen or sulfur.

The inventors have further identified that steric congestion is another major contributor toward formation of metathesis-inactive complexes. This problem is circumvented by the use of planar ligand sets, or ligands of reduced steric demand.

The use of alternative "pseudohalide" anionic ligands or ligand sets can reduce steric demand, leading to the generation of modular, tunable ligands for selective Ru catalysts. Importantly, the anionic ligands can be adapted to achieve stereoselective catalysis for the production of specific product enantiomers from achiral or prochiral substrates.

The synthesis of the new catalysts is straightforward and high yields can be readily obtained under specific conditions. The pseudohalide ligands are modular, such that they can be easily modified in terms of steric demand, and can be easily adapted for inclusion of chirality. This offers the ability to fine-tune metathesis activity and selectivity within Ru catalysts. Stereoselective metathesis provides a particularly important opportunity, given the increasing importance of metathesis technologies in natural product and small molecule synthesis. In this regard the inventors have succeeded in generating novel Ru compounds suitable for use as metathesis catalysts, which include multidentate anionic ligands (see examples).

The compounds of the present invention include those of formula Ia or Ib:

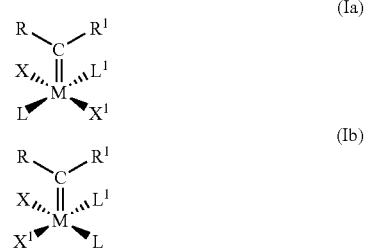

wherein:

M is selected from the group consisting of Ru and Os;

R and $R^1$ are independently selected from the group consisting of hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_{2-20}$ alkenyloxy, aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl; each optionally substituted with one or more $C_1$–$C_5$ alkyl, halogen, $C_1$–$C_5$ alkoxy, phenyl optionally substituted with halogen, $C_1$–$C_5$ alkyl, or $C_1$–$C_5$ alkoxy;

X and $X^1$ are anionic ligands, wherein X and $X^1$ are each independently selected from -Z-Q, or wherein one of X and $X^1$ is halide and the other of X and $X^1$ is -Z-Q, each Z comprising O, S, N, or C, and each Q comprising a planar electron-withdrawing group;

L and $L^1$ are independently selected from any neutral electron donor; and wherein any 2–3 of X, $X^1$, L, or $L^1$ are optionally covalently linked to form a chelating multidentate ligand. Without wishing to be bound by theory, it is believed that this alternative anionic ligand coordination of the Ru atom imparts the improved properties of catalyst configuration and activity in accordance with the above discussion. Molecular modelling of catalyst configurations strongly suggests that the compounds of the present invention permit improved access for substrate coordination and processing (see Examples, and FIG. 2).

Preferably, the substitutions to the Z spacer atoms if present may be selected from the group consisting of hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl; each optionally substituted with one or more $C_1$–$C_5$ alkyl, halogen, $C_1$–$C_5$ alkoxy, phenyl optionally substituted with halogen, $C_1$–$C_5$ alkyl, or $C_1$–$C_5$ alkoxy The compounds of the present invention include a range of Ru coordination compounds, in which the Ru atom is coordinated by anionic ligands. These anionic ligands include, but are not limited to, cyclic, bicyclic or multicyclic ring systems that do not contact the Ru atom via ring-carbon atoms. Instead, the anionic ligands bind Ru via a 'spacer atom' selected from, but not limited to, oxygen, sulfur, nitrogen, or carbon; most preferably oxygen. This feature differentiates the compounds of the present invention over those of the prior art. Without wishing to be bound by theory, it is believed that this feature confers particular advantages upon the compounds of the present invention. The structure of the corresponding complexes (see for example FIG. 2) indicates the absence of steric contraints to provide a suitable coordination site for the incoming substrate. This contrasts directly with the alkoxide coordinated Ru complexes described by Sanford et al. (Reference 12), which exhibit comparatively low catalytic activity presumably resulting from the bulk of the anionic alkoxide ligands. The inventors attribute the near-zero metathesis activity of alkoxide-Ru catalysts to steric crowding compounded by thermal instability. The replacement of alkoxide, for example, with aryloxide appears to significantly relieve these steric contraints, dramatically improving catalytic activity.

Preferably, the compounds of formula I include X and $X^1$, wherein both anionic ligands comprise -Z-Q. However, the invention is not limited in this regard. The invention further encompasses compounds of the formula I in which one of the anionic ligands X or $X^1$ comprises halogen, and the other anionic ligand comprises -Z-Q. In this way, the compounds of the invention include those in which only one of the "traditional" halide anions has been replaced by -Z-Q. Such compounds may be formed intentionally, or in specific circumstances may result from unsuccessful attempts to generate compounds in which both X and $X^1$ are -Z-Q. In any event, the presence of a single anionic ligand of the formula -Z-Q is within the realms of the present invention. Indeed, such compounds in which one of X or $X^1$ is halide, and the other of X and $X^1$ is -Z-Q may be particularly useful as catalysts, for example, in olefin metathesis reactions. Without wishing to be bound by theory, such catalysts may exhibit preferred characteristics such as alternative reaction mechanisms or even a capacity to generate stereospecific products. Such catalyst compounds may exhibit alternative steric constraints.

Under specific circumstances where both X and $X^1$ are -Z-Q, the anionic ligands of the compounds of the present invention may be optionally linked to form multidentate ligands such as, for example, diolate, biphenolate and binaphtholate groups. Such multidentate ligands are particularly suitable for use in the production of chirally active Ru catalysts, for the generation of specific product enantiomers. This option presents particular advantages to the catalysts of the present invention, in the generation of small molecule therapeutics, in which chirality is essential for biological activity. The inventors have succeeded in the production of compounds of formula I, wherein the anionic ligands are covalently linked to form a multidentate ligand (see Examples).

In preferred embodiments of the present invention, the Ru catalysts include anionic ligands that comprise a partly or fully halide-substituted carbon ring system linked to the spacer atom. For example, in a most preferred embodiment, the compounds of the present invention include anionic ligands of the formula $OC_6Hal_5$, wherein the oxygen atom directly coordinates the Ru atom. The presence of one or more electron-withdrawing halide substituents on the carbon ring system presents additional advantages by allowing the olefin metathesis reaction to proceed in, for example, fluorous media without excessive degradation of the Ru catalyst or unwanted side-reactions (for example ring-closing metathesis of diethyldiallylmalonate can be carried out in perfluorobenzene with complete conversion to the ring-closed product—see Examples).

In preferred embodiments, the Ru catalyst compounds of the present invention may include pyridine as a neutral ligand. In most preferred embodiments the pyridine may comprise one or more electron withdrawing groups such as for example Bromine. Without wishing to be bound by theory, it is considered that the presence of for example, a bromine substituent increases the lability of the pyridine/Ru bond, thereby to increase the catalytic efficiency and turn-over rate of the corresponding catalyst (see Examples).

Facile Catalyst Purification

The presence of halide groups can facilitate catalyst purification, and allow catalyst to be chemically separated from product, enabling synthesis of products for demanding applications such as pharmaceutical synthesis without heavy-metal contamination. This also allows recovery of active catalyst for subsequent reuse. Separation can be very simply effected, for example by column chromatography on, for example, silica gel using ethyl acetate-hexanes as eluant, which leaves the catalyst at the top of the column. Previous attempts to remove the catalysts of the prior art by this method can result in poor separation, necessitating multiple purification cycles. This significant advantage is discussed in more detail in the examples. Alternatively, extraction can be effected by carrying out reactions in mixed fluorous-organic solvents. The catalyst can be separated from organic products or reagents on the basis of its preferred solubility in the fluorous medium, and the preferred solubility of non-fluorinated organic products in the organic medium. Another possible method involves use of fluorous solvents after catalysis is complete, enabling recovery of the catalyst species.

Solid Support Attachment

Another significant advantage of the compounds of the present invention pertains to facile and 'permanent' solid support attachment. In this regard, the aryl groups of each anionic ligand can be modified to permit anchoring of the anionic ligand to a solid support. To date, the Ru catalyst compounds of the prior art have typically been attached to solid supports via the neutral ligands, or via the alkylidene group (see, for example, a review of cross-metathesis of olefins provided by Reference 18, and also Reference 19). In direct contrast, the compounds of the present invention present an opportunity for solid support attachment via one or both of the anionic ligands. In this way, the compounds of the present invention may retain significant catalytic activity whilst remaining bound to the solid support, by virtue of the alternative configuration of the coordinated Ru complex.

The nature of the anchoring of Ru catalysts of the prior art differs from those of the present invention. Like their parent, non-supported catalysts, such prior art catalyst compounds require loss of one "L-donor" ligand before they can effect metathesis. If the "anchoring" L-donor ligand is lost, the catalyst will detach from the solid support before catalysis can proceed. Again, this will result in leaching of the catalyst off the solid support. The inventors reasonably expect anchoring via a covalent Ru—X bond to be more stable than anchoring via a dative Ru-L bond, particularly when both anionic ligands are tethered to the solid support, thereby conferring improved robustness to the solid support-catalyst linkage.

The nature of the 'permanent' Ru complex—solid support interaction contrasts directly with comparable 'boomerang' Ru catalysts of the prior art. Typically, such 'boomerang' catalysts are tethered to a solid support through the neutral ligands or the alkylidene group. Such prior art catalyst compounds must be detached from the solid support before catalysis can proceed, and therefore must be reattached to the solid support for catalyst purification, or multiple rounds of olefin metathesis (hence the terminology, 'boomerang'). It is an important advantage of the compounds of the present invention, at least in preferred embodiments, to permit fixed solid support attachment such that catalytic activity is maintained whilst the compound is bound to the support. In this way, there is no need for catalyst detachment and re-attachment, thereby avoiding inevitable catalyst losses that are experienced with comparable 'boomerang' catalysts.

Importantly, both the solid-phase and fluorous-phase reactions can be used to enable olefin metathesis in a continuous operation rather than the batch operation currently required. Alternatively, in batch reactions, the catalyst activity can be maintained during repeated rounds of olefin metathesis reactions. For example, the active catalyst may be adhered to the solid support via the anionic ligands to form a 'flow-through' column suitable for passing an olefin metathesis reaction mixture therethrough. Organic precursors are added at the top of the column, and organic products are collected at the bottom. In this way, the presence of the anionic donor ligand can facilitate recovery, separation and recycling of active catalyst. This presents clear advantages for industrial use of the catalyst, and natural product synthesis.

The inventors have established various strategies for the selective synthesis of alkylidene or alkylidyne derivatives of ruthenium, via steric matching/mismatching between two and three dimensional L-donor ligands and an incoming pseudohalide. Many of the compounds of the present invention exhibit excellent activity for metathesis reactions, and in particular RCM, even at very low catalyst loading. This chemistry affords convenient access to a new, active, and modular class of Ru catalysts for olefin metathesis.

EXAMPLES

Example 1

Figure 2:
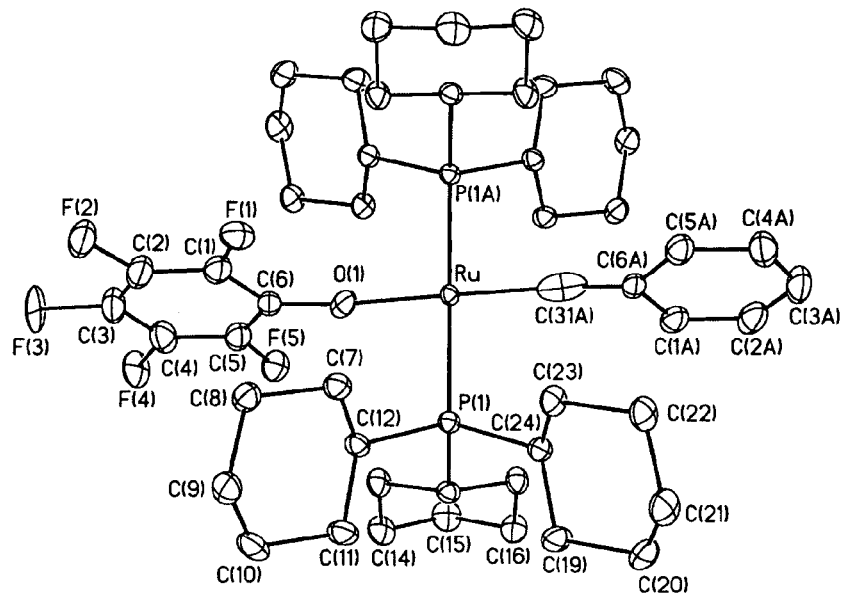
FIG. 2 provides Oak Ridge Thermal Ellipsoid Plot Program for Crystal Structure Illustrations (ORTEP) representations of compounds of formula 4c and 5; hydrogen atoms and solvates have been omitted. Thermal ellipsoids at 30% probability level. Aryloxide and alkylidyne ligands in the compound of formula 4c related by centre of inversion. The description provides the corresponding tables of crystal data collection and refinement parameters, atomic coordinates, bond lengths and angles, anisotropic displacement parameters and hydrogen coordinates.
Figure 2:
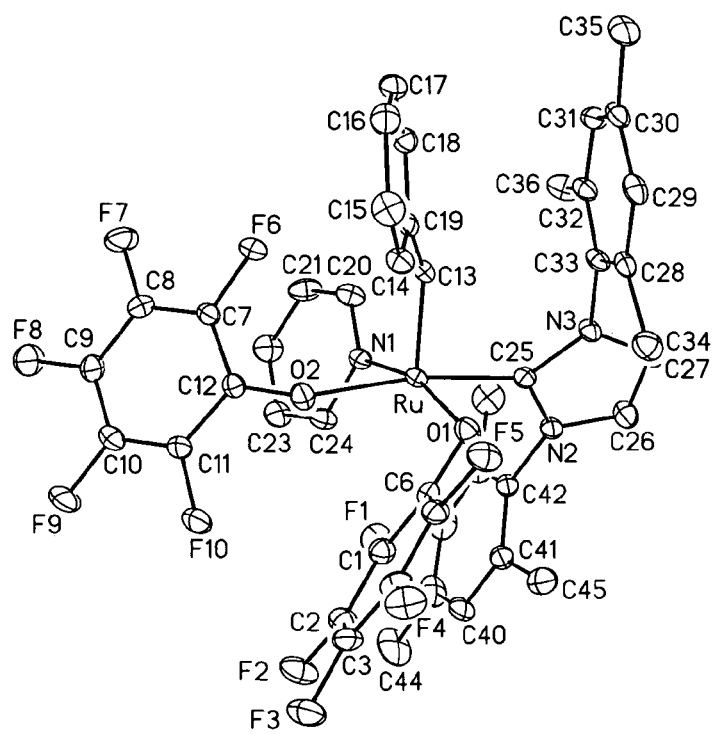

Production of Compound 4c (see FIGS. 1 and 2)

Treatment of compound 1a (FIG. 1) with $TlOC_6F_5$ effected quantitative conversion to four-coordinate alkylidyne compound 4c (FIG. 1, Scheme 2) within 3 hours at room temperature. The reaction is carried out under $N_2$ at room temperature using standard Schlenk or drybox techniques and dry, oxygen-free solvents. Addition of $TlOC_6F_5$ (566 mg, 1.46 mmol) in 7 mL toluene to a purple solution of $RuCl_2(CHPh)(PCy_3)_2$ (600 mg, 0.73 mmol) in 7 mL benzene resulted in quantitative reaction (as judged by NMR analysis) within 3 h, accompanied by a colour change to dark green. The suspension was filtered through Celite™ and the filtrate concentrated to dryness. On redissolving the residue in cold (−35° C.) ether, a green powder of 4c slowly deposited. This was filtered off and washed with cold ether. Yield 395 mg (56%); isolated yields are limited by high solubility in ether. Characterization data: $^1H$ NMR ($C_6D_6$, 298K) δ 7.68 (d, 2H, $J_{HH}$=7.6 Hz, Ph o-CH), 6.97 (t, 1H, $J_{HH}$=7.5, Ph p-CH), 6.75 (t, 2H, $J_{HH}$=7.9, Ph m-CH), 2.23–2.18 (m, 8H, Cy), 1.94–1.54 (m, 36H, Cy), 1.30–1.15 (m, 8H, Cy), 1.08–0.90 (m, 8H, Cy). $^{31}P\{^1H\}$ NMR ($C_6D_6$, 298K) δ 42.59 (s). $^{13}C\{^1H\}$ NMR ($C_6D_6$, 298K) δ 250.2 (RuCPh, located by HMBC), 153–125 (CF, CH), 35.6–26.6 ($CH_2$). $^{19}F\{^1H\}$ NMR ($C_6D_6$, 298K) δ −90.27 (dd, 2F, $J_{FF}$=11.3, 22.6 Hz), −93.35 (t, 2F, $J_{FF}$=22.1 Hz), −106.73 to −106.98 (m, 1F). Anal. Calcd. for $C_{49}H_{71}F_5OP_2Ru$: C, 63.00; H, 7.66%. Found: C, 62.74; H, 8.12%. Crystals deposited from benzene solution. The complex was isolated as a green, air-stable, ether-soluble powder; yields were limited to ca. 60% by its high solubility. The approximately square planar molecular structure (FIG. 2) closely resembles that reported for compound 4b (Ref. 11). Formation of compound 4c despite the acidity of the perfluorophenol coproduct implies a powerful driving force for the reaction.

Modelling studies point towards steric crowding within the five-coordinate intermediate (cf. Compound 3, see FIG. 1), sufficient to promote interaction between the alkylidene proton and the phenoxide oxygen. This is ultimately relieved by elimination of perfluoroalcohol. Failure to observe the corresponding reaction for the t-butoxide system (Ref. 11, 12) despite the thermodynamically more favourable liberation of t-butanol, is consistent with prohibition of the alkylidene-alkoxide interaction by the bulk of the t-butyl substituent. Relief of steric pressure can then only be accommodated by phosphine loss.

Example 2

Production of Compound 5 (see FIGS. 1 and 2)

$Ru(OC_6F_5)_2(CHPh)(py)(IMes)$

The analysis disclosed in Example 1 led the inventors to consider that alkylidene complexes of simple aryloxide ligands could potentially be accessed by attenuating the bulk of the neutral ligands as well as the pseudohalide. For this reason, the inventors turned their attention to NHC complexes of the type shown as compound 1d (FIG. 1), containing an approximately two-dimensional IMes ligand (IMes=N,N'-bis(mesityl)imidazol-2-ylidene) (Ref. 13). Reaction of $TlOC_6F_5$ with compound 1d was selective for transmetallation, yielding solely alkylidene 5. Addition of $TlOC_6F_5$ (470 mg, 1.21 mmol) with $RuCl_2(CHPh)(IMes)(py)_2$ (440 mg, 0.607 mmol) in 20 mL benzene gave complete reaction (as judged by NMR analysis) within 8 h. The green suspension was filtered through Celite™ to remove TlCl. The Celite was washed with $CH_2Cl_2$, and the combined filtrate was reduced to dryness. Precipitation from $CH_2Cl_2$-hexane afforded a green, air-stable powder. Yield 526 mg (92%). Compound 5 was isolated in 92% yield, and characterized by spectroscopic, microanalytical and crystallographic analysis <<<$^1H$ NMR ($CDCl_3$, 298K) δ 18.76 (s, Ru═CH), 7.96 (d, 2H, $J_{HH}$=5.2 Hz, Ph CH), 7.47–7.38 (m, 4H, CH), 7.15 (s, 2H, CH), 7.10 (t, 2H, $J_{HH}$=7.7 Hz, CH), 7.03 (s, 2H, CH), 6.81 (t, 2H, $J_{HH}$=6.9, CH), 6.66 (s, 2H), 2.37 (s, 6H, $CH_3$), 2.27 (s, 6H, $CH_3$), 1.58 (s, 6H, $CH_3$). $^{13}C\{^1H\}$ NMR ($CDCl_3$, 298K) δ 313.89 (s, Ru═CH), 183.46 (s, NCN), 154.41 to 123.94 (CH, CF), 21.51 (s, Mes $CH_3$), 18.39 (s, Mes $CH_3$), 17.47 (s, Mes $CH_3$). $^{19}F\{^1H\}$ NMR ($CDCl_3$, 298K) δ −86.43 to −86.54 (m, 2F), −86.70 to −86.74 (m, 2F), −94.27 (t, 2F, $J_{FF}$=22.3 Hz), −94.50 (t, 2F, $J_{FF}$=22.5 Hz), −104.79 to −105.01 (m, 1F), −105.81 to −106.04 (m, 1F). IR ν(C═C) 1646 $cm^{-1}$. Anal. Calcd. for $C_{43}H_{55}F_{10}N_3O_2Ru$: C, 57.45; H, 3.75; N, 4.47%. Found: C, 57.46; H, 3.63; N, 4.56%. X-ray quality crystals were grown by slow evaporation of a toluene solution. As shown in FIG. 2, its geometry is square pyramidal, with alkylidene occupying the apical site, consistent with the high trans effect of this ligand.

Example 3

Comparison of Ru Compounds for the Catalysis of a Test RCM Reaction

Retention of the potentially labile pyridine ligand within compound 5 (FIG. 1) attests to the absence of steric constraints in this five-coordinate complex. Importantly, it also signifies the presence of a potential coordination site for incoming substrate in compound 5, in contrast with the sterically encumbered alkoxide complexes of compound 2 (Ref. 12). Indeed, compound 5 exhibits dramatically increased activity for ring closing metathesis (Table 1). Thus, the alkoxide derivatives show very poor catalytic activity for RCM of diethyldiallylmalonate even at high catalyst loadings (20 mol %; i.e. a ratio of 5 mol substrate per mol of catalyst). Catalyst 2a achieves less than one turnover; catalyst 2b achieves two turnovers. In contrast, catalyst 5 effects >99% ring-closing of this substrate at lower catalyst loadings (ranging from 5 mol % to 0.05 mol %) over periods ranging from 20 minutes to 3 hours. Catalytic experiments were carried out under argon in refluxing chloroform, using between 0.05 and 0.5 mM of diene substrate and from 0.01 to $2.5 \times 10^{-6}$ mM of catalyst; conversions were determined by $^1$H NMR and by GC.

TABLE 1

Ring-closing metathesis via Ru-alkylidene catalysts*

| Entry | Cat | S | [S]/[C] | Solvent | Time (min) | Conv (%) | TOF (h$^{-1}$) |
|---|---|---|---|---|---|---|---|
| 1[a] | 2a | 6a | 5 | $C_6D_6$ | 5760 | <5 | <<1 |
| 2[a] | 2b | 6a | 5 | $C_6D_6$ | 720 | 40 | <<1 |
| 3 | 5 | 6a | 10 | $C_6D_6$ | 15 | 56[b] | 22[b] |
| 4 | 5 | 6a | 20 | $C_6F_6$ | 120 | >99 | 10 |
| 5 | 5 | 6a | 20 | $CDCl_3$ | 20 | >99 | 60 |
| 6 | 5 | 6b | 20 | $CDCl_3$ | 20 | >99[c] | 60 |
| 7 | 5 | 7 | 20 | $CDCl_3$ | 90 | >99 | 13 |
| 8 | 5 | 6a | 2,000 | $CDCl_3$ | 180 | >99 | 667 |
| 9 | 5 | 6a | 200,000 | $CDCl_3$ | 1440 | 20 | 1667 |

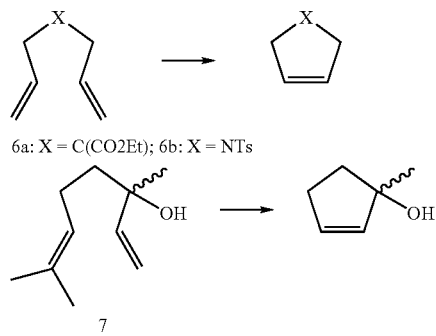

6a: X = C(CO2Et); 6b: X = NTs

7

Conditions: [S] = 0.05–0.5 mM; [C] = 0.01–2.5 × 10$^{-6}$ mM; reactions under Ar, at 60° C. ($C_6D_6$) or at reflux; conversions determined by $^1$H NMR; TOF = turnover frequency. [a]Ref. 12.
[b]Catalyst incompletely dissolved. [c]92% selectivity for the expected 2,5-dihydropyrrole product. [17]

With reference to Table 1, metathesis activity is retained in fluorocarbon solvents (Entry 4), and at exceptionally low catalyst loadings (Entries 8–9). Up to 40,000 turnovers are observed for RCM of the benchmark substrate diethyldiallylmalonate, using only $5 \times 10^{-4}$ mol % of compound 5. A lower limit of 0.05 mol % has been established for chlororuthenium catalyst compound 1c under comparable conditions (Ref. 14). Catalyst loadings of 5–20 mol % are typical in Ru-catalyzed RCM, owing to the short lifetimes of the active Ru-methylidene intermediate (Ref. 15, 16). Even at 20 mol %, however, compounds 2a and 2b achieve turnover numbers of only 0.25 and 2 respectively (Ref. 12).

Example 4

Crystallographic Data for Compounds 4c (CCDC) and 5 (see FIG. 2)

Crystallographic data (excluding structure factors) have been deposited with the Cambridge Crystallographic Data Centre as CCDC publications #208990 (4c) and 208989 (5). These data can be obtained free of charge on application to the CCDC at 12 Union Road, Cambridge CB2 1EZ, UK; fax: (+44) 1223-336-033; email deposit@ccdc.cam.ac.uk. X-ray quality crystals were grown from benzene solution. Suitable crystals were selected, mounted on thin glass fibers using paraffin oil, and cooled to the data collection temperature. Data were collected on a Bruker AXS SMART 1k CCD diffractometer using 0.3° ω-scans at 0, 90, and 180° in φ. Initial unit-cell parameters were determined from 60 data frames collected at different sections of the Ewald sphere. Semi-empirical absorption corrections based on equivalent reflections were applied (Blessing, R., Acta Cryst., 1995, A51, 33–38). No symmetry higher than triclinic was observed in the diffraction data, and solution in the centrosymmetric space group option, P-1, yielded chemically reasonable and computationally stable results of refinement for both 4c and 5. The structures were solved by direct methods, completed with difference Fourier syntheses and refined with full-matrix least-squares procedures based on $F^2$. The molecule 4c resides on an inversion center such that the phenoxide ligand is disordered with the alkylidyne ligand. For 5, a molecule of cocrystallized benzene solvent was located at an inversion centre. All non-hydrogen atoms were refined with anisotropic displacement parameters. All hydrogen atoms were treated as idealized contributions. All scattering factors and anomalous dispersion factors are contained in the SHEXTL 5.10 program (Sheldrick, G. M., SHELXTL V5.10, Siemens Analytical X-ray Instruments Inc., Madison Wis. 1997).

Example 5

Variation of Anionic Ligands

Depending upon reaction conditions, the inventors have achieved replacement of up to two halide ligands (e.g. Cl) from Ru with a generally planar group. However, under specific conditions the inventors sometimes observe the replacement of only one halide. Regardless of whether one or two halide ligands are replaced, desirable catalytic activities are generally observed (see below). For this reason, the compounds and methods of the invention are not intended to be limited to Ru complexes comprising either one or two modified anionic ligands. For example, in the examples described herein, the inventors observed successful replacement of two Cl ligands on Ru with two $OC_6F_5$ ligands. However, presumably as a result of steric constraints, only one Cl ligand was replaced with $OC_6Cl_5$ or $OC_6Br_5$ under the reaction conditions described.

Experimental. Experiments carried out under inert atmosphere of either Ar or $N_2$ using Schlenk techniques or a glovebox.

$Ru(OC_6F_5)_2(CHPh)(3-Br-py)(IMes)$

Two equivalents of $TlOC_6F_5$ (409 mg, 1.05 mmol) are added directly to $RuCl_2(CHPh)(IMes)(3-Br-py)_2$ (465 mg, 0.526 mmol) in toluene (20 mL). The suspension is stirred overnight and the white TlCl precipitate is removed by filtration through Celite. The Celite is washed with $CH_2Cl_2$ (5 mL) and the green solution is reduced to dryness under vacuum. The green residue is precipitated from a minimum amount of $CH_2Cl_2$ with pentane (20 mL). Green powder is isolated by filtering and drying under vacuum, 451 mg, 84%. $^1H$ NMR $C_6D_6$ δ 18.84 (s, 1H, RuCH), 8.14 (m, 1H, py CH), 7.85(d, $J_{HH}$=5.8, 1H, py CH), 7.60 (d, $J_{HH}$=7.6, 2H, Ph CH), 7.19–7.14 (m, 1H, Ph, CH), 6.98–6.88 (m, 4H, Ph, Mes), 6.59–6.54 (m, 1H, py CH), 6.48 (s, Mes CH), 6.05 (s, 2H, NCH), 5.66 (dd, $^3J_{HH}$=8.2 $^3J_{HH}$=5.8, py Ch), 2.23 (s, 6H, Mes $CH_3$), 2.15 (s, 6H, Mes $CH_3$), 1.51 (s, 6H, Mes $CH_3$). $^{13}C\{^1H\}$ $CDCl_3$ δ 313.43 (s, RuCH), 182.81 (s, NCN), 155.36 (s, Ar CH), 153.00 (s, Ar CH), 152.00 (s, Ar C) 143.31–134.91 (m, Ar CF), 140.02 (s, Ar C), 137.74 (s, Ar CH), 136.63 (s, Ar C), 136.19 (s, Ar C), 134.92 (s, Ar C), 129.58 (s, Ar CH), 129.24 (s, Ar CH), 128.02 (s, Ar CH), 124.85 (s, Ar CH), 123.75 (s, NCHCHN), 119.37 (s, Ar C), 21.64 (s, $CH_3$), 18.44 (s, $CH_3$), 17.58 (s, $CH_3$). $^{19}F\{^1H\}$ $CDCl_3$-87.24 to –87.43 (m, 4F), –95.40 to –95.58 (m, 4F), 105.38 (tt, $^3J_{FF}$=22.6, $^4J_{FF}$=8.5, 1F), –106.77 (tt, $^3J_{FF}$=25.4 $^4J_{FF}$=8.5, 1F). Anal. calcd $C_{43}H_{54}F_{10}BrN_3O_2Ru$: C, 53.00; H, 3.11; N, 3.99%. Found C, 52.68; H, 3.36; N, 4.12%.

$Ru(OC_6Cl_5)Cl(CHPh)(IMes)(py)$

One equivalent of $TlOC_6Cl_5$ (130 mg, 0.276 mmol) is added directly to $RuCl_2(CHPh)(IMes)(Py)_2$ (200 mg, 0.276 mmol) in benzene (20 mL). The suspension is stirred overnight and the white TlCl precipitate is removed by filtration through Celite. Then the solvent is removed under vacuum. The green residue is precipitated from a minimum amount of toluene and hexanes (40 mL) at –78° C. At this point there is still a trace of less than 5% of unidentified side product ($^1H$ NMR RuCHPh=17.84). The green solid is then dissolved in toluene (5 mL) and filtered through neutral alumina three times. Clean final product is isolated by removing solvent under vacuum to 0.5 mL and precipitating with hexane (20 mL) at –78° C., filtered and dried under vacuum, 170 mg (70%). $^1H$ NMR $C_6D_6$ δ 19.78 (s, RuCH, 1H), 8.29 (br s, 2H, py), 8.12 (br s, 2H, Ph), 7.15–7.11 (m, 2H, Ph), 6.88 (t, $J_{HH}$=9, 2H, Ph), 6.74 (s, 2H, CHMes), 6.33 (s, 2H, CHMes), 6.17 (t, $J_{HH}$=7.2, 1H, py), 6.12 (s, 2H, NCH), 5.92–5.88 (m, 2H, py), 2.46 (s, 6H, Mes $CH_3$), 2.07 (s, 6H, Mes $CH_3$), 2.00 (s, 6H, Mes $CH_3$). $^{13}C\{^1H\}$ $C_6D_6$ δ 314.87 (s, RuCH), 181.39 (s, NCN), 161.47 (s, Ar C), 152.67 (s, Ar C), 151.45 (s, Ar CH), 138.92 (s, Ar C), 137.08 (s, Ar C), 137.00 (s, Ar C), 135.72 (s, Ar CH), 129.99 (s, Ar CH), 129.19 (s, Ar CH), 129.07 (s, Ar CH), 129.03 (s, Ar CH), 127.99 (s, Ar CH), 127.77 (s, Ar CH), 124.27 (s, Ar CH), 122.91 (s, NCHCHN), 20.87 (s, $CH_3$), 18.57 (s, $CH_3$), 17.91 (s, $CH_3$). New alkylidenes appear when dissolved in $CDCl_3$ over 4 hours.

$Ru(OC6Br5)Cl(CHPh)(py)(IMes)$

One equivalent of $TlOC_6Br_5$ (191 mg, 0.276 mmol) are added directly to $RuCl_2(CHPh)(IMes)(py)_2$ (200 mg, 0.276 mmol) in benzene (20 mL). The suspension is stirred for four hours and the white TlCl precipitate is removed by filtration through Celite. Then the solvent is removed under vacuum. The green residue is precipitated from a minimum amount of toluene and pentane (40 mL) at –35° C. After drying 257 mg (85%) of green powder is obtained. Precipitation at a warmer temperature enables removal of unwanted decomposition products. Filtering through alumina causes the color to turn purple and no product is obtained. $^1H$ NMR ($CDCl_3$) δ 19.28 (s, Ru=CH, 1H), 7.99–7.97 (m, ArH, 2H), 7.88 (d, $J_{HH}$=7.32, ArH, 2H), 7.37–7.34 (m, ArH, 2H), 7.24–7.20 (m, ArH, 2H), 7.17–6.89 (m, ArH, 4H), 6.70–6.69 (m, ArH, 2H), 6.52 (s, ArH, 2H), 2.29 (s, $CH_3$, 6H), 2.21 (s, $CH_3$, 6H), 1.84 (s, $CH_3$, 6H). $^{13}C\{^1H\}$ ($CDCl_3$) δ 315.60 (s, Ru=CH), 181.53 (s, NCN), 163.19 (s, Ar C), 152.49 (s, Ar C), 151.34 (s, Ar CH), 139.27 (s, Ar C), 137.54 (s, Ar C), 137.07 (s, Ar C), 136.06 (s, Ar CH), 133.73 (s, Ar C), 129.88 (s, Ar CH), 129.73 (s, Ar CH), 129.42 (s, Ar CH), 129.11 (s, Ar CH), 128.21 (s, Ar C), 127.76 (s, Ar CH), 125.49 (s, Ar C), 124.85 (s, Ar CH), 123.35 (s, NCHCHN), 120.12 (s, Ar C), 116.36 (s, Ar C),107.77 (s, Ar C), 21.28 (s, $CH_3$), 18.77 (s, $CH_3$), 17.93 (s, $CH_3$).

$Ru(OC_6Br_5)Cl(CHPh)(Br-py)(IMes)$

One equivalent of $TlOC_6Br_5$ (111 mg, 0.161 mmol) is added directly to $RuCl_2(CHPh)(IMes)(3-Br-py)_2$ (142 mg, 0.161 mmol) in benzene (20 mL). The green solution is stirred overnight and the white TlCl precipitate is removed by filtration through Celite. The Celite is washed with toluene (5 mL) and the green solution is reduced to dryness under vacuum. The green residue is precipitated from a minimum amount of toluene with pentane (–35°, 20 mL). Green powder is isolated by filtering and drying under vacuum, 172 mg (91%). $^1H$ NMR ($C_6D_6$) δ 19.55 (s, RuCH, 1H), 8.64 (br s, ArH, 1H), 7.98 (br s, ArH, 1H), 7.16–7.07 (m, ArH, 3H), 6.84 (t, J=7.9, ArH, 2H), 6.72 (s, Mes ArH, 2H), 6.34 (s, Mes ArH, 2H), 6.27 (br s, ArH, 1H), 6.11 (s, I ArH, 2H), 5.48 (br s, 1H), 2.42 (s, Mes $CH_3$, 6H), 2.15 (s, Mes $CH_3$, 6H), 1.97 (s, Mes $CH_3$, 6H). $^{13}C\{^1H\}$ $C_6D_6$ δ 315.54 (s, RuCH), 180.36 (s, NCN), 163.69 (s, Ar C), 153.46 (s, Ar C), 153.06 (s, RuCHC), 150.07 (s, Ar C), 139.42 (s, Ar C), 138.82 (s, Ar CH), 137.64 (s, Ar C), 137.57 (s, Ar C), 137.15 (s, Ar C), 137.15 (s, Ar C), 130.28 (s, Ar CH), 129.79 (s, Ar CH), 129.66 (s, Ar CH), 129.50 (s, Ar CH), 129.37 (s, Ar C), 128.40 (s, Ar CH), 128.26 (s, Ar CH), 126.49 (s, Ar C), 126.08 (s, Ar C), 124.79 (s, Ar CH),124.19 (s, NCHCHN), 120.74 (s, Ar C), 119.61 (s, Ar C), 116.65 (s, Ar C), 108.87 (s, Ar C), 21.39 (s, $CH_3$), 19.05 (s, $CH_3$), 18.32 (s, CH3). $IR^1$: ν (C=C) 1603 (w), 1586 (w), 1553 (m). Anal. calcd $C_{39}H_{34}Br_6N_3ORu$: C, 39.81; H, 2.91; N, 3.57%. Found C, 39.29; H, 2.87; N, 3.18%.

$Ru(SCN)_2(CHPh)(py)(IMes)$

Two equivalents of AgSCN (91.6 mg, 0.552 mmol) are added directly to $RuCl_2(CHPh)(IMes)(Py)_2$ (200 mg, 0.276 mmol) in benzene (20 mL). The suspension is stirred for 16 hours and the off white AgCl precipitate is removed by filtration through Celite. Then the solvent is removed under vacuum. The green residue is precipitated from a minimum amount of benzene and pentane (40 mL). After drying under vacuum overnight 184 mg (97%) of green powder is obtained. $^1H$ NMR ($CDCl_3$) δ 17.99 (s, RuCH, 1H), 8.38 (d, $^2J_{HH}$=3.9, 2H, ArH), 7.69 (d, $^2J_{HH}$=4.0, 2H, ArH), 7.56 (d, $^2J_{HH}$=5.5, 2H, ArH), 7.34–7.24 (m, 2H, ArH), 7.09–6.88 (m, 3H, Arh), 6.86–6.82 (m, 4H, ArH, NCH), 6.58 (t, $^2J_{HH}$=6.1, 2H, ArH), 6.43 (s, 4H, ArH), 2.09 (s, 12H, $CH_3$), 1.96 (s, 6H, $CH_3$). $^{13}C\{^1H\}$ $CDCl_3$ δ 324.24 (s, RuCH), 180.26 (s, NCN), 151.84 (s, ArC), 150.69 (s, ArCH), 149.94 (s, ArCH), 139.05 (s, ArC), 136.98 (br s, SCN), 136.58 (s, ArC),136.29 (s, ArCH), 134.99 (s, ArCH), 131.06 (s, ArCH), 130.49 (s, ArCH), 128.88 (s, ArCH), 128.29 (s, ArCH), 128.15 (s, ArCH), 124.98 (s, NCH), 123.83 (s, ArCH), 20.89 (s, $pCH_3$), 17.83 (s, $oCH_3$). IR: ν (SCN) 2095 (s), (C=C) 1600 (m).

$Ru(SC_6F_5)_2(CHPh)(IMes)(py)$

To $RuCl_2(CHPh)(IMes)(py)_2$ (200 mg) stirring in 20 mL of $C_6H_6$ is added two equivalents of $TlSC_6F_5$ (223 mg). Reaction is complete after 15 min and color changes from green to red. As observed by $^1$H and $^{19}$F NMR, stirring for longer periods transforms the compound apparently to the cis isomer noted by the appearance of a new benzylidene and addition sets of peaks in the $^{19}$F spectrum. After filtering through Celite to remove AgCl the solvent is removed under vacuum. The red residue is then precipitated from 10 mL of pentane at −78° C. The brown powder is collected on a filter and dried overnight to yield 55 mg (20%). trans $^1$H NMR (C$_6$D$_6$) δ 19.19 (s, RuCH, 1H), 8.54 (s, $^2$J$_{HH}$=7.53, 2H, ArH), 7.60 (br s, 2H, ArH), 7.23 (t, $^2$J$_{HH}$=7.1, 1H, ArH), 6.42 (br s, 1H, ArH), 6.19 (br s, 2H, ArH), 5.84 (br s, 1H, ArH), 5.41 (s, 2H, NCH), 2.85–2.34 (br s, 12H, CH$_3$), 2.34–1.97 (br s, 6H, CH$_3$). cis $^1$H NMR (C$_6$D$_6$) 18.20 (s, RuCH, 1H). $^{19}$F{$^1$H} C$_6$D$_6$ δ −56.22 (d, J$_{FF}$=26.82, 2F), −88.63 (t, J$_{FF}$=21.74, 1F), −90.99 (t, 22.3, 2F) second order splitting is poorly resolved.

Ru(CHPh)(3,5-CF$_3$—OC$_6$H$_3$)$_2$(IMes)(py)

Green solution with KCl precipitate. $^1$H NMR (C$_6$D$_6$) δ 18.69 (s, Ru=CH, 1H), 7.80 (d, J$_{HH}$=7.7, ArH, 2H), 7.39 (d, J$_{HH}$=7.7, ArH, 2H), 6.96–6.94 (m, ArH, 4H), 6.89–6.84 (m, ArH, 3H), 6.78 (s, ArH, 2H), 6.67–6.63 (m, ArH, 2H), 6.46 (s, ArH, 2H), 6.34 (s. ArH, 1H), 6.09–6.04 (m, ArH, 2H), 6.03 (s, ArH, 2H), 2.18 (s, CH$_3$, 6H), 1.41 (s, CH$_3$, 12H).

Ru(O$_2$C$_{20}$H$_4$F$_8$)(CHPh)(IMes)(py)

To a solution of RuCl$_2$(CHPh)(IMes)(Py)$_2$ (141 mg, 0.194 mmol) in benzene (20 mL) is added solid Tl$_2$O$_2$C$_{20}$H$_4$F$_4$ (180 mg, 0.214 mmol). After stirring overnight a white precipitate forms (TlCl) and is removed by filtering through Celite, completely washing product through with 5 mL CH$_2$Cl$_2$. Solvent is then removed under vacuum. The green residue is dissolved in 3 mL of CH$_2$Cl$_2$ and filtered through a plug of alumina in a pipette three times. The solvent is reduced to the minimum solvating volume and green solid is precipitated by adding hexane (10 mL) and filtered. An impurity ($^1$H NMR CD$_2$Cl$_2$ 17.88 s) grows in over time and is more pronounced in CDCl$_3$. Large crystals are grown by slow evaporation of THF solution with n-decane layered on top. First crop 42 mg, a brown substance is isolated from the filtrate. $^1$H NMR CD$_2$Cl$_2$ δ 19.19 (s, RuCH), 7.92 (d, J$_{HH}$=9.0, 1H), 7.76–7.72 (m, 2H), 7.51–7.43 (m, 2H), 7.25 (t, J$_{HH}$=9.0, 1H), 7.14 (s, 3H), 7.11–7.01 (m, 1H), 7.09–7.08 (m, 1H), 7.03–6.94 (m, 4H), 6.91–6.90 (m, 1H), 6.88 (s, 1H), 6.87–6.81 (m, 2H), 6.55 (d, J$_{HH}$=9.0, 1H), 3.73–3.63 (m, 2H, THF), 2.56 (s, 6H, CH$_3$), 2.11 (s, 6H, CH$_3$), 1.88–1.75 (m, THF CH$_3$, 8H). δ 310.16 (s, Ru=CH), 183.29 (s, NCN), 155.58–124.02 (Ar, CH, CF), 25.93 (s, CH$_3$), 21.40 (s, CH$_3$), 18.11 (s, CH$_3$). MALDI-TOF [M-py (79)]$^+$= 924 m/z. IR nujol ν(C=C) 1663, 1601, 1565 cm$^{-1}$. New alkylidenes appear when dissolved in CDCl$_3$, not soluble in C$_6$D$_6$.

Example 6

Comparison of Ring Closing Metathesis Turnover Rates for Compounds of Formula I

Several compounds that fall within the scope of formula I were studied for their capacity to cyclize the test substrate diethyldiallyl malonate substantially in accordance with Example 3. The results shown in FIG. 3 compare the turnover rates for the reaction, as catalyzed by each of the aforementioned compounds, under various conditions of temperature and solutes, 0.5 mol % Ru, 0.1M DEDAM.

Poor turnover rates were observed for all of the test compounds at room temperature, compared to higher temperatures.

Most unexpectedly, the observed rates of catalytic turnover did not correlate with the degree of electronegativity of the substituents on the anionic ligands. Ru(OC$_6$Cl$_5$)Cl (CHPh)(IMes)(py) and Ru(OC$_6$Br$_5$)Cl(CHPh)(IMes)(py) comprising anionic ligands having chlorine and bromine substituents respectively, gave rise to much higher catalytic turnover rates than Ru(OC$_6$F$_5$)$_2$(CHPh)(IMes)(py) which included anionic ligands having fluorine substituents. For example, Ru(OC$_6$Cl$_5$)Cl(CHPh)(IMes)(py) produced turnover rates typically at least 4-fold higher than for Ru(OC$_6$F$_5$)$_2$ (CHPh)(IMes)(py) under similar conditions (either 61° C./CDCl$_3$, or 40° C./CH$_2$Cl$_2$). Moreover, under specific conditions Ru(OC$_6$Br$_5$)Cl(CHPh)(IMes)(py) produced turnover rates even higher than for Ru(OC$_6$Cl$_5$)Cl (CHPh)(IMes)(py)(40° C./CH$_2$Cl$_2$ or 60° C./C$_6$D$_6$). Therefore, the overall results shown in FIG. 3 suggest that the catalytic turnover efficiency of the compounds may correlate inversely with the electron density at the spacer atom.

Figure 3:
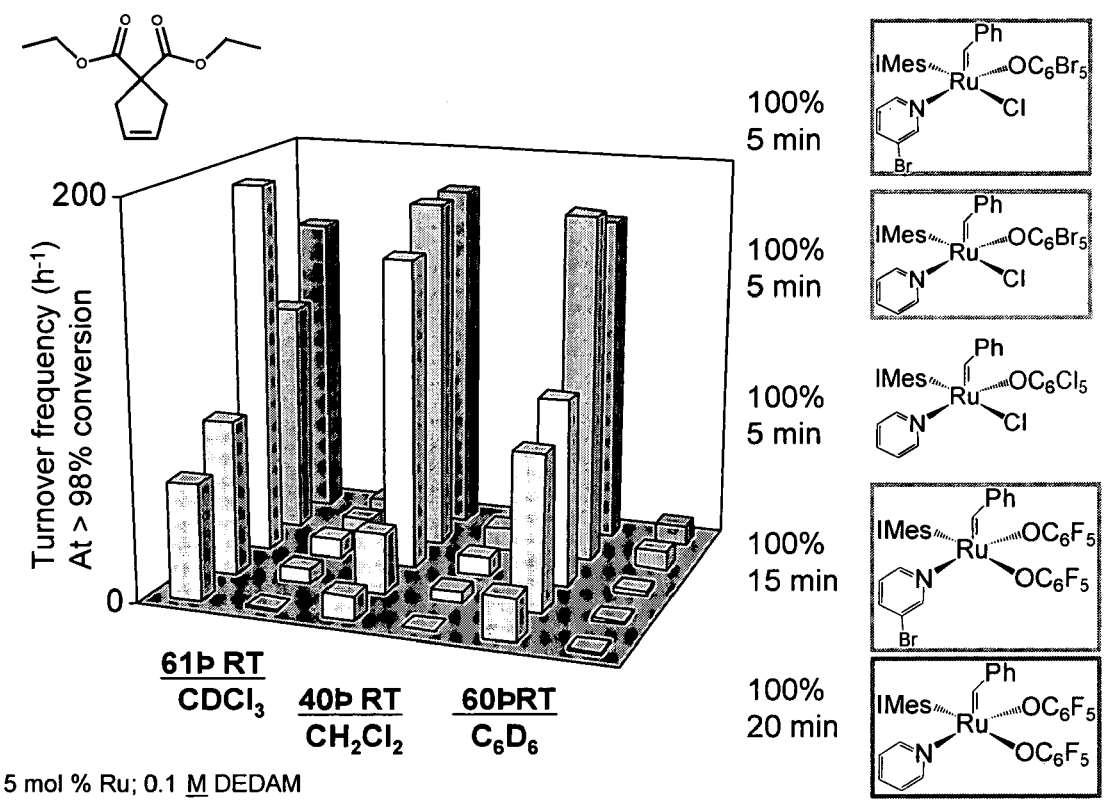
FIG. 3 provides a graph to compare turnover frequency ($h^{-1}$) at more than 98% conversion for compounds of the present invention under various test conditions. The test reaction involved ring-closing metathesis of diethyldiallyl malonate.

FIG. 3 illustrates another interesting result, specifically in relation to the neutral ligand, pyridine. The presence of the electronegative bromine subtituant at the 3-position of the pyridine can further enhance the catalytic turnover efficiency of the test compounds. For example, Ru(OC$_6$F$_5$)$_2$(CHPh)(3-Br-py)(IMes) which includes bromine substituted pyridine, exhibits a greater turnover rate that corresponding Ru(OC$_6$F$_5$)$_2$(CHPh)(py)(IMes) regardless of the reaction conditions. Without wishing to be bound by theory, the presence of the electron withdrawing bromine on the pyridine ring is expected to increase the lability of pyridine—Ru coordination, thereby enhancing the capacity of the pyridine to function as a leaving moiety for substrate-catalyst attachment (see Example 12). In view of these observations, the compounds of the present invention encompass, at least in preferred embodiments, Ru complexes comprising pyridine or similar neutral ligands including one or more electron withdrawing substituents such as halide atoms.

Also of note is the activity of Ru(OC$_6$Cl$_5$)Cl(CHPh) (IMes)(py) in CDCl$_3$, which is significantly higher than for the other solvents.

These results demonstrate a clear trend between pKa and activity. However this relationship is complicated by the change in size of the phenoxy substituents. Bromine is much bigger than fluorine and is therefore much more bulky, perhaps helping to push the pyridine off the active site. There is likely a synergy between steric and electronic parameters but it remains possible that one factor operates independently.

Example 7

Comparison of Ring Opening Metathesis Metathesis Turnover Rates for Various Compounds of Formula I Several compounds of formula I were tested for their capacity to catalyze ring opening metathesis, using cyclooctene as a test substrate. The graph shown in FIG. 4 illustrates the degree of conversion of the cyclized substrate to the corresponding product.

The general protocol involved the following: to a rapidly stirring solution of catalyst (1.925×10$^{-6}$ mol) in 3.85 mL of solvent was added 50 uL (0.385 mmol) cis-cyclooctene. [S]=0.1 M, [C]=0.5 mmol. Then 0.75 mL was removed and put into an NMR tube which is fitted with a plastic top and sealed with a small amount of parafilm. The sample was then placed in the NMR probe and set to spin at 20 MHz. Spectra were recorded at set time integrals. Experiments at elevated temperatures were done in a Schlenk tube using a one point protocol. Conversion was determined by ¹HNMR integration of olefinic peaks.

In accordance with Example 6, an inverse correlation was generally observed between the degree of electronegativity of the substituents on the anionic ligands, and the rate of conversion of the test substrate. Ru(OC$_6$Br$_5$)Cl(CHPh)(IMes)(py) ("Br/py") gave rise to very rapid conversion of the substrate in ring opening metathesis, with almost 100% conversion in less than one hour. Under the same reaction conditions, Ru(OC$_6$Cl$_5$)Cl(CHPh)(IMes)(py)("Cl/py") was a less efficient catalyst for ring opening metathesis of cyclooctene, with almost complete conversion in less than 2 hours. Ru(OC$_6$F$_5$)$_2$(CHPh)(IMes)(py)("F/py") was much less efficient, with only 70% product conversion after 10 hours reaction time.

Figure 4:
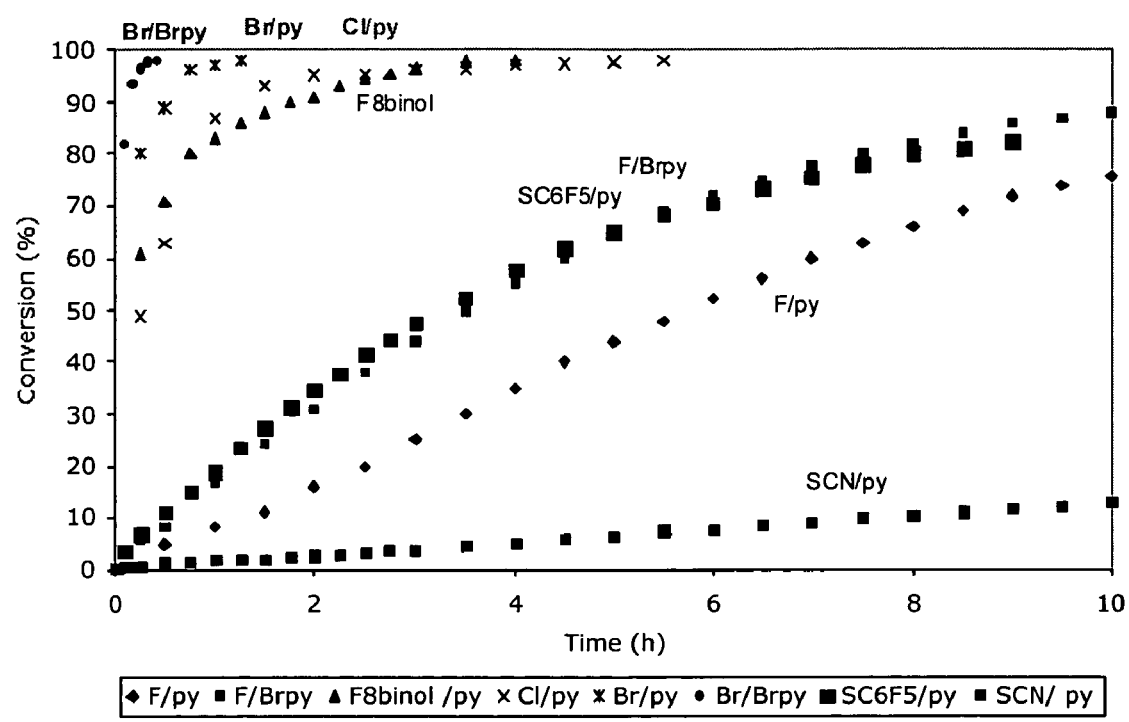
FIG. 4 provides a graph to compare percentage conversion for ring opening metathesis of cyclooctene for selected catalysts of the present invention.

The presence of a bromine substituent on the neutral pyridine ligand also enhanced the rate of cyclooctene conversion, as shown in FIG. 4. This increase was apparent for Ru compounds comprising either bromine or fluorine substituted anionic ligands (compare results for Ru(OC$_6$F$_5$)$_2$(CHPh)(3-Br-py)(IMes) ("F/Brpy") with the results for Ru(OC$_6$F$_5$)$_2$(CHPh)(IMes)(py) ("F/py"), and compare the results for Ru(OC$_6$Br$_5$)Cl(CHPh)(IMes)(3-Br-py) ("Br/Brpy") with Ru(OC$_6$Br$_5$)Cl(CHPh)(IMes)(py)("Br/py").

Ru(O$_2$C$_{20}$H$_4$F$_8$)(CHPh)(IMes)(py)("F8binol") also exhibited impressive conversion efficiency comparable to Ru(OC$_6$Cl$_5$)Cl(CHPh)(IMes)(py)("Cl/py") and indicated in FIG. 4. This highlights the potential of multidentate ligands to generate catalyst within the scope of the present invention that exhibit advantageous catalytic properties such as the capacity to generate chiral products.

Two further compounds of the present invention, which comprise sulfur instead of oxygen as the atom directly coordinating the Ru, were tested for their capacity for RCM of cyclooctene. Firstly, as shown in FIG. 4, Ru(SC$_6$F$_5$)$_2$(CHPh)(IMes)(py) ("SC6F5/py") exhibited a rate of conversion of cyclooctene comparable with Ru(OC$_6$F$_5$)$_2$(CHPh)(IMes)(3-Br-py)("F/Brpy"). Strikingly, the presence of the sulfur atoms appeared to enhance catalytic activity when compared with the equivalent fluorophenoxy coordinated catalyst comprising unsubstituted pyridine Ru(OC$_6$F$_5$)$_2$ (CHPh)(IMes)(py)("F/py"). In contrast, Ru(SCN)$_2$(CHPh)(py)(IMes) ("SCN/py") exhibited a definite albeit relatively low level of catalytic activity. The SCN derivative was much slower but appeared to have a linear reaction slope, indicating that the limiting step is not pyridine dissociation but rather propagation.

Nonetheless, the results using both Ru(SC$_6$F$_5$)$_2$(CHPh)(IMes)(py) and Ru(SCN)$_2$(CHPh)(py)(IMes) demonstrate that the compounds of the present invention are not limited only to those comprising anionic ligands that coordinate Ru via oxygen. Rather, other "linker" or "spacer" atoms including but not limited to sulfur also generate catalytic compounds with desirable properties for metathesis reactions.

Example 8

Comparison of Ring Closing Metathesis Activity of Ru(OC$_6$F$_5$)$_2$(CHPh)(IMes)(py) with Different Substrates Ru(OC$_6$F$_5$)$_2$(CHPh)(IMes)(py) was used to test for the capacity of the compounds of the present invention to catalyze a range of ring closing metathesis reactions. Table 2 provides a summary of the reactions tested, including the substrates used, and the expected products generated. Standard conditions were used for each reaction, and included 0.1M substrate, 5 mol % of catalyst, with reactions conducted under reflux conditions in CDCl. To a small Schlenk flask charged with 1 mL of solvent is added 0.005 mmol of catalyst then 0.1 mmol of substrate, [C]=0.1 M, [S]=0.005 M. The mixture is then stirred rapidly and heated to reflux (oil bath set to 65° C.). Conversion is determined by either GC with decane internal standard or by ¹HNMR integration of allylic and olefinic peaks, with dioxolane internal standard.

The results shown in tables 2 and 3 demonstrate the capacity of the compounds of the present invention to modify a broad range of substrates, and highlight the commercial potential of the corresponding catalyst formulations. Particularly noteworthy are entries 10 and 11 in Table 2, which pertain to ring closure to produce 10 and 16 member heterocyclic rings. (Macrocyclizations and large ring closure are discussed in greater detail in later examples). These results provide compelling evidence that the catalyst compounds of the present invention are suitable for ring closing metathesis to generate heterocyclic rings with 6 or more members. Moreover, the compounds of the present invention frequently out-perform those of the prior art, including the first generation Grubbs catalysts (GI) and the second generation Grubbs catalysts (GII) as indicated. A key following Table 2 indicates the various catalyst compounds listed in the Table. The data relating to the catalyst compounds of the present invention, which include compounds a, b, h, i, and j (see Key), are indicated in Table 3 in bold.

TABLE 2

RCM reactions catalyzed by Ru(OC$_6$F$_5$)$_2$(CHPh)(IMes)(py)

| | Substrate | Product | Conv. (%) | Time | Comments |
|---|---|---|---|---|---|
| 1 | 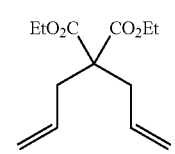 | 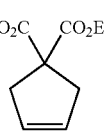 | >99 | 15 min | Benchmark five membered ring substrate, also test for cat compatibility with ester functionality |

TABLE 2-continued

RCM reactions catalyzed by Ru(OC$_6$F$_5$)$_2$(CHPh)(IMes)(py)

| | Substrate | Product | Conv. (%) | Time | Comments |
|---|---|---|---|---|---|
| 2 | 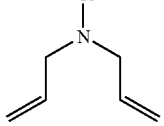 | 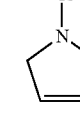 | >99 | 45 min | Nitrogen heterocycle, tests compatibility with protected nitrogens, rearranges under heating conditions |
| 3 | 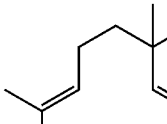 | 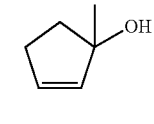 | >99 | 15 min | Tests steric pressure with trisubstituted olefin, also free alcohol compatibility |
| 4 | 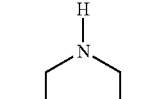 |  | 10 | 4 h | Free amine compatibility, known to poison catalysts |
| 5 | 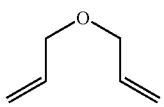 |  | — | — | Ether compatibility |
| 6 | 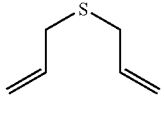 |  | >99 | 15 min | Sulfur compatibility, thioester |
| 7 | 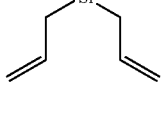 | 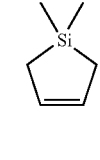 | 30 | 15 min | Si compatibility, impurities often pose a problem, used unpurified substrate |
| 8 | 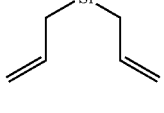 | 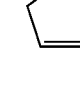 | 86 | 15 min | Si compatibility, impurities often pose a problem, used unpurified substrate |
| 9 | 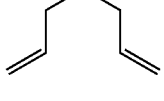 | 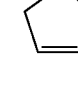 | NR | 15 min | Allylic alcohol compatibility, ethylene may reenter and rearrange product |
| 10 | 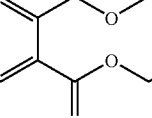 | 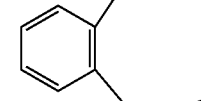 | 62 | 15 min | Formation of 10 membered ring, more difficult than 5 membered rings, unpurified substrate |

TABLE 2-continued

RCM reactions catalyzed by Ru(OC₆F₅)₂(CHPh)(IMes)(py)

| | Substrate | Product | Conv. (%) | Time | Comments |
|---|---|---|---|---|---|
| 11 | (structure: CH₂=CH-(CH₂)₈-C(=O)-O-(CH₂)₄-CH=CH₂) | (16-membered macrolactone) | 70<br>1.5:1 Z:E<br>95<br>2:1 | 5 h<br>17 h | 16 membered ring, competing oligomerization may be a problem, high dilution and slow addition required "value added" product |

TABLE 3 comparison of the catalytic activity of the compounds of the present invention to catalyse the reactions summarized in Table 2 (Note - the key following Table 3 indicates the catalyst used for the reaction. Some of the data from Table 3 is derived from various literature references, as indicated)

| | Substrate | Product | Cat. | mol % | T °C. | Solvent | Time | Conv. (sel.) | TON | TOF h⁻¹ |
|---|---|---|---|---|---|---|---|---|---|---|
| 1 | EtO₂C, CO₂Et (diallyl) | EtO₂C, CO₂Et (cyclopentene) | a[20] | 5 | 62 | CDCl₃ | 15 m | 100 | 20 | 80 |
| | | | b | 5 | 21 | C₆D₆ | 90 m | 100 | 20 | 13 |
| | | | b | 5 | 40 | CH₂Cl₂ | 5 m | 100 | 20 | 240 |
| | | | c[21] | 0.05 | 40 | CH₂Cl₂ | 2 h | 70 | 1400 | 700 |
| | | | a[20] | 0.05 | 62 | CDCl₃ | 1 h | 92 | 1840 | 1840 |
| | | | d[22] | 5 | 20 | CDCl₃ | 30 m | 30 | 20 | 40 |
| | | | e[23] | 20 | 60 | C₆D₆ | 96 h | 5 | 1 | <<1 |
| | | | f[24] | 3 | 70 | C₆D₅Cl | 1 h | 100 | 30 | 30 |
| | | | g[25] | 5 | 55 | CH₂Cl₂ | 4 h | 100 | 20 | 5 |
| | | | h | 5 | 40 | CH₂Cl₂ | 5 m | 100 | 20 | 240 |
| | | | i | 5 | 40 | CDCl₃ | 5 m | 100 | 20 | 240 |
| | | | j | 5 | 60 | CDCl₃ | 5 m | 100 | 20 | 240 |
| | | | k | 5 | 60 | | 5 m | 100 | 20 | 240 |
| 2 | Ts-N(allyl)₂ | Ts-pyrroline | a[20] | 5 | 62 | CDCl₃ | 20 m | 100 (91) | 20 | 60 |
| | | | GII | 1 | 21 | CH₂Cl₂ | 1 h | 100 | 100 | 100 |
| | | | h | 5 | 21 | CDCl₃ | 4 h | 88 (81) | 18 | 4.5 |
| | | | h | 5 | 62 | CDCl₃ | 4 h | 100 (75) | 20 | 5 |
| | | | j | 5 | 62 | CDCl₃ | 15 m | 100 | 20 | 80 |
| | | | k | 5 | 62 | CDCl₃ | 15 m | 100 | 20 | 80 |
| 3 | (linalool-type, OH) | (cyclopentenol) | a[20] | 5 | 62 | CDCl₃ | 15 m | 100 | 20 | 80 |
| | | | a | 5 | 62 | CDCl₃ | 1 h | 100 | 2000 | 2000 |
| | | | GI[27] | 5 | 21 | CDCl₃ | 1 h | 100 | 20 | 20 |
| | | | g[25] | 5 | 55 | C₆D₅Cl | 4 h | 96 | 19.2 | 4.8 |
| | | | h | 5 | 62 | CDCl₃ | 15 m | 100 | 20 | 80 |
| | | | j | 5 | 62 | CDCl₃ | 15 m | 100 | 20 | 80 |
| | | | k | 5 | 62 | CDCl₃ | 15 m | 100 | 20 | 80 |
| 4 | HN(allyl)₂ | pyrroline | a | 5 | 62 | CDCl₃ | 4 h | 10 | 2 | 5 |
| 5 | diallyl ether | dihydrofuran | a | 5 | 62 | CDCl₃ | 1 h | 100 (32) | 20 | 20 |
| | | | g[25] | 5 | 55 | C₆D₅Cl | 4 h | 100 | 20 | 5 |
| | | | h | 5 | 62 | CDCl₃ | 15 m | 90 (94) | 18 | 72 |
| | | | j | 5 | 62 | CDCl₃ | 15 m | 100 (77) | 20 | 80 |
| | | | k | 5 | 62 | CDCl₃ | 15 m | 100 | 20 | 80 |
| 6 | diallyl sulfide | dihydrothiophene | a | 5 | 62 | CDCl₃ | 15 m | 100 | 20 | 80 |
| | | | h | 5 | 62 | CDCl₃ | 15 m | 100 | 20 | 80 |
| | | | j | 5 | 62 | CDCl₃ | 15 m | 100 | 20 | 80 |
| | | | k | 5 | 62 | CDCl₃ | 15 m | 100 | 20 | 80 |

TABLE 3-continued comparison of the catalytic activity of the compounds of the present
invention to catalyse the reactions summarized in Table 2 (Note - the key
following Table 3 indicates the catalyst used for the reaction. Some of the data
from Table 3 is derived from various literature references, as indicated)

| | Substrate | Product | Cat. | mol % | T ° C. | Solvent | Time | Conv. (sel.) | TON | TOF h$^{-1}$ |
|---|---|---|---|---|---|---|---|---|---|---|
| 7 | (diallyldimethylsilane) | (silacyclopentene) | a | 5 | 62 | CDCl$_3$ | 15 m | 30 | 6 | 24 |
| | | | h | 5 | 62 | CDCl$_3$ | 15 m | 15 | 3 | 12 |
| | | | j | 5 | 62 | CDCl$_3$ | 15 m | 18 | 3.6 | 14.4 |
| 8 | (diallyldiphenylsilane) | (silacyclopentene) | a | 5 | 62 | CDCl$_3$ | 15 m | 86 | 17.2 | 68.8 |
| | | | GII[26] | 5 | 110 | Toluene | 5 h | 70 | 14 | 2.8 |
| | | | h | 5 | 62 | CDCl$_3$ | 15 m | 100 | 20 | 80 |
| | | | j | 5 | 62 | CDCl$_3$ | 15 m | 94 | 18.8 | 75.2 |
| | | | k | 5 | 62 | CDCl$_3$ | 15 m | 100 | 20 | 80 |
| 9 | (diallyl carbinol) | (cyclopentenol) | a | 5 | 62 | CDCl$_3$ | 15 m | 0 | 0 | 0 |
| 10 | (diallyl phthalate) | (macrolactone) | a | 5 | 62 | CDCl$_3$ | 15 m | 37 | 12.4 | 49.6 |
| | | | g[25] | 5 | 55 | C$_6$D$_5$Cl | 4 h | 96 | 19.2 | 4.8 |
| | | | h | 5 | 62 | CDCl$_3$ | 15 m | 44 | 9 | 35 |
| | | | j | 5 | 62 | CDCl$_3$ | 15 m | 41 | 8.2 | 32.6 |

Key to catalyst compounds indicated in Table 3

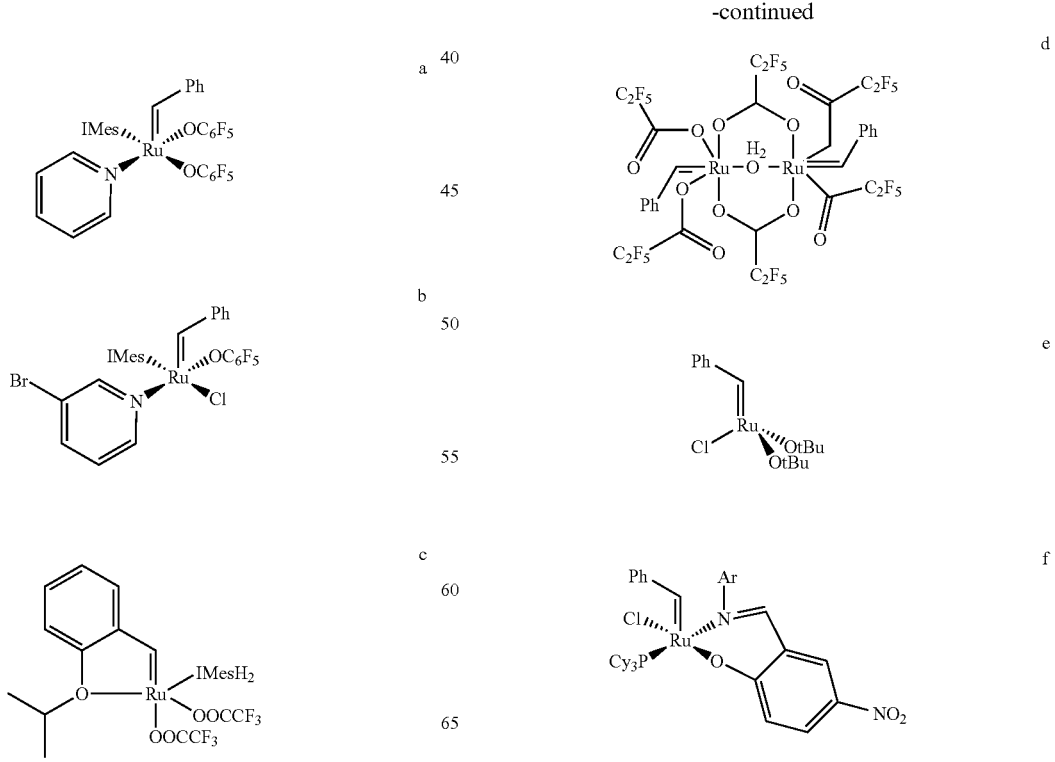

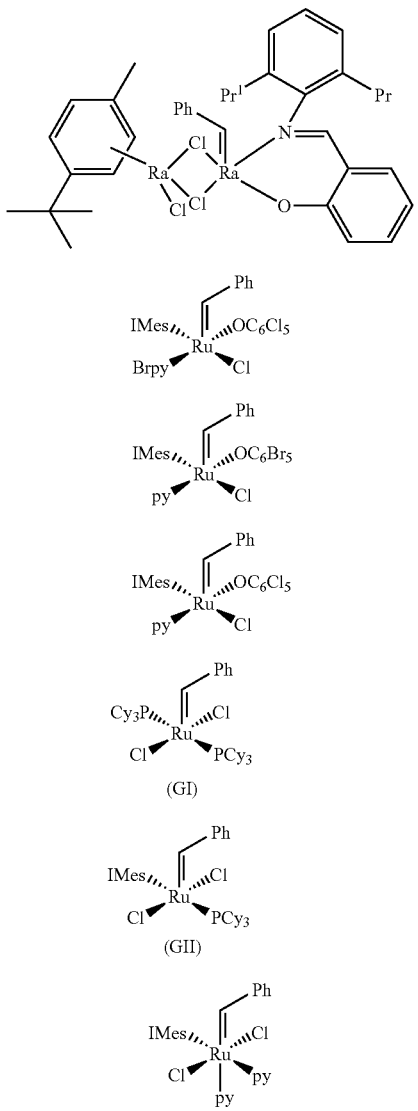

Example 9

Analysis of RCM with Low Catalyst Loading

Experiments were conducted to compare the capacity of various compounds of the present invention to effect ring-closing metathesis of the test substrate diethyldiallyl malonate (DDM). Table 4 compares the turn over numbers for DDM following a 24 hour reaction at 60° C. in CDCl$_3$ with a 200,000:1 catalyst loading.

TABLE 4

TON of DDM, 200,000:1, 24 hours 60° C. CDCl$_3$

| Test compound | TON |
| --- | --- |
| Ru(OC$_6$F$_5$)$_2$(CHPh)(IMes)(py) | 40,000 |
| Ru(OC$_6$F$_5$)$_2$(CHPh)(IMes)(3-Br-py) | 15,961 |
| Ru(OC$_6$Cl$_5$)Cl(CHPh)(IMes)(py) | 22,000 |
| Ru(OC$_6$Br$_5$)Cl(CHPh)(IMes)(py) | 22,000 |
| Ru(OC$_6$Br$_5$)Cl(CHPh)(IMes)(3-Brpy) | 20,000 |
| Grubbs I | 8,660 |
| Grubbs II | 12,391 |

The results in Table 4 indicate that Ru(OC$_6$F$_5$)$_2$(CHPh)(IMes)(py) outperforms the other test compounds including the various of the Grubbs systems in the RCM of DDM at low catalyst loadings. The results of a separate experiment are provided in Table 5, which compared the turn over frequency of various compounds of the present invention for RCM of DDM following a 1 hour reaction at 60° C. in CDCl$_3$.

TABLE 5

TOF of DDM, 2000:1, 1 hour 60° C. CDCl$_3$

| Test compound | TOF |
| --- | --- |
| Ru(OC$_6$F$_5$)$_2$(CHPh)(IMes)(py) | 1850 |
| Ru(OC$_6$F$_5$)$_2$(CHPh)(IMes)(3-Br-py) | 1240 |
| Ru(OC$_6$Br$_5$)Cl(CHPh)(IMes)(3-Brpy) | 850 |

The results in Table 5 demonstrate that the flouro derivative achieves a higher TOF for 100% conversion of 2000 equivalents of DDM. However, the use of a general protocol for closing all substrates with only 0.05 mol % catalyst is of limited scope—only the 'easiest' substrates such as DDM can be fully converted under such conditions.

Example 10

Analysis of the Generation of Alternative Products During RCM Catalysis

The inventors have conducted some preliminary analysis of alternative products generated during RCM with various catalyst compounds of the present invention. For this purpose, two standard RCM reactions were utilized for this comparative analysis, as indicated in FIGS. 5 and 6.

Figure 5:
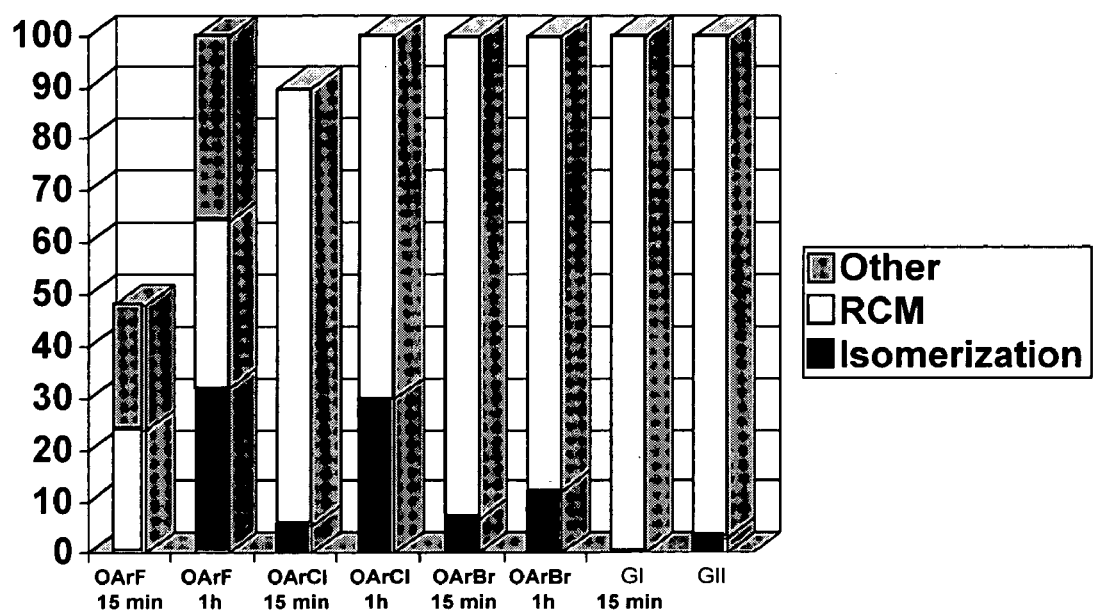
FIG. 5 provides a graph to compare reaction products, including isomerization products, following RCM of diallyl ether using various compounds of the present invention.
Figure 5:
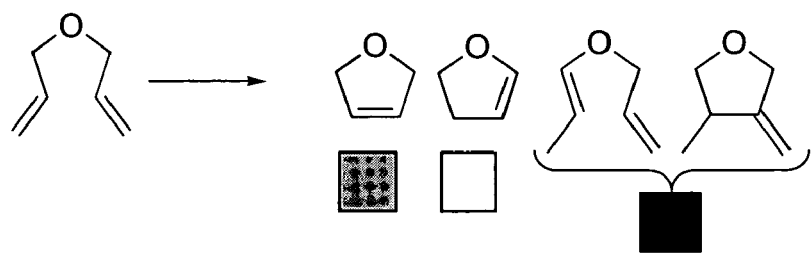

FIG. 5 illustrates a comparison of reactions conducted at 62° C. with the test substrate diallyl ether. OArF=Ru(OC$_6$F$_5$)$_2$(CHPh)(IMes)(py), OArCl=Ru(OC$_6$Cl$_5$)Cl(CHPh)(IMes)(py), OArBr=Ru(OC$_6$Br$_5$)Cl(CHPh)(IMes)(py), and Cl=RuCl$_2$(CHPh)(IMes)(py)$_2$. The results indicate that the more active Ru(OC$_6$Cl$_5$)Cl(CHPh)(IMes)(py) and Ru(OC$_6$Br$_5$)Cl(CHPh)(IMes)(py) catalysts are more likely produce RCM product than Ru(OC$_6$F$_5$)$_2$(CHPh)(IMes)(py). In fact, only one third of the products generated after a one hour reaction with the flourophenoxy coordinated catalyst resulted directly from RCM. The other products were formed via double bond migrations of diallylether to vinyl ethers. These compounds were characterized by GC-MS and $^1$H NMR.

Figure 6:
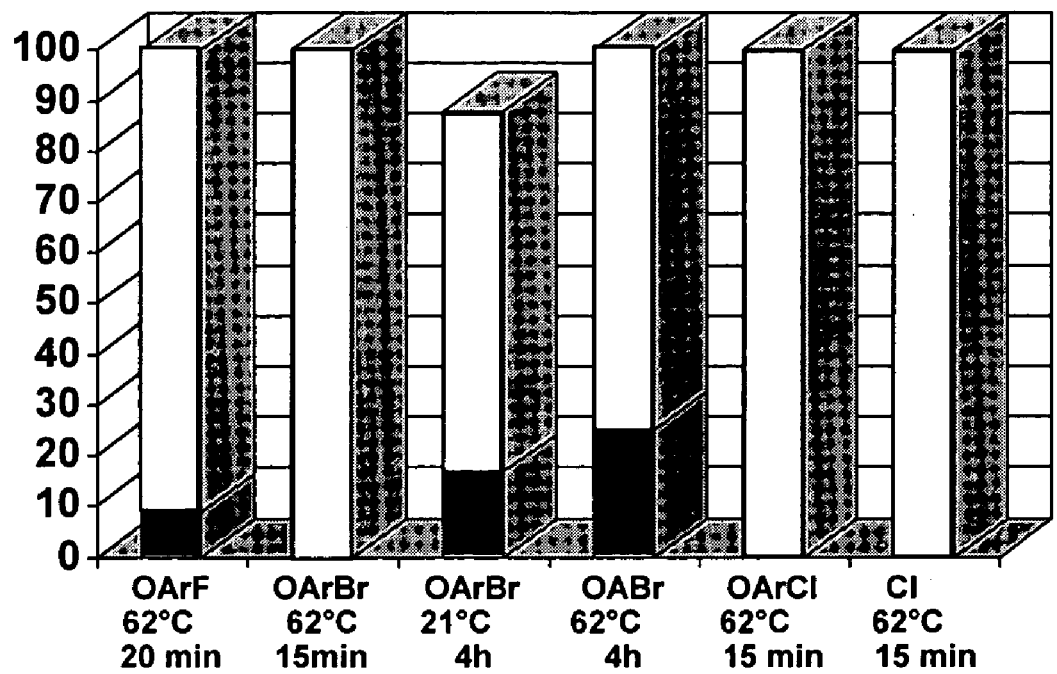
FIG. 6 provides a graph to compare reaction products, including isomerization products, following RCM of diallyl-N-tosylamine using various compounds of the present invention.
Figure 6:
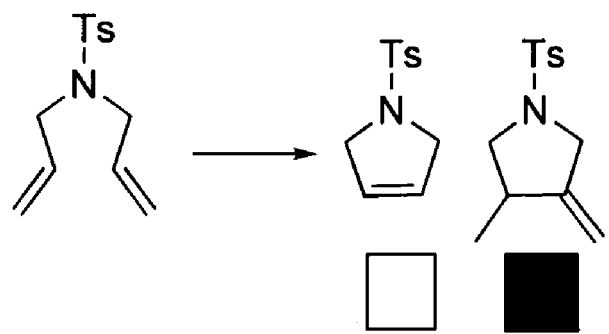

Another example is illustrated in FIG. 6. In this example, all test compounds performed well as RCM catalysts for diallyl amine. Formation of the isomerized product increased slightly over time. However, the degree of isomerization appeared indifferent to the reaction temperature. In general, highly active catalysts appeared to convert the substrate to RCM product cleanly, wherein the Ru(OC$_6$F$_5$)Cl(CHPh)(IMes)(py) catalyst showed high activity for product rearrangement, adding ethylene even before RCM had gone to completion.

Example 11

RCM of Large Sized Rings

The compounds of the present invention have been tested for their capacity to catalyze ring closing metathesis of large macrocyclic compounds. Various substrates were selected to test the catalysts for specific properties, as discussed below:

Example 11a

RCM of Oxa-cyclohexadec-11-en-2-one (Exaltolide)

Analysis of RCM of Oxa-cyclohexadec-11-en-2-one (Exaltolide) allowed for analysis of catalyst E:Z selectivity.

To reduce cross metathesis products high dilution ([S]=10 mM, [C]=0.5 mM) and slow addition is used. Conversion and isomer ratios determinded by $^1$H NMR integrations of olefinic peaks in crude reaction mixture. Product also verified by MS and DEPT 135.

Oxa-cyclohexadec-11-en-2-one (Exaltolide): 30 mg (0.111 mmol) of diene and 5 mol % of catalyst were dissolved in 10 mL each of solvent and added slowly (1 drop per second) through a dropping funnel to 5 mL of refluxing solvent. The resulting mixture was then refluxed for a total of 3 hours, for Ru(OC$_6$F$_5$)$_2$(CHPh)(py)(IMes) total reaction time is 18 hours. After reaction the solvent is removed under vacuum and dissolved in CDCl$_3$ for NMR analysis.

The results are shown below:

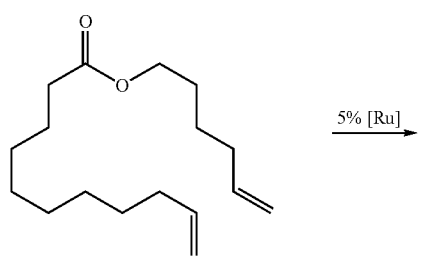

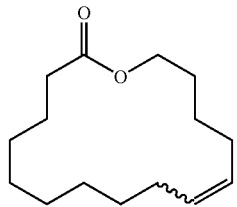

References 28 and 29:

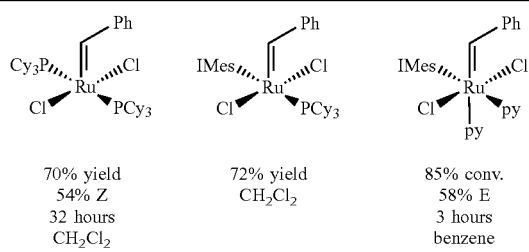

GC-MS, $^1$H NMR and DEPT

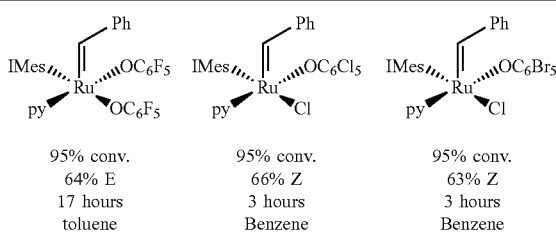

Example 11b

RCM of 1,6-Dioxa-cyclopentadec-3-ene

To reduce cross metathesis products high dilution ([S]=10 mM, [C]=0.5 mM) and slow addition is used. Conversion and isomer ratios determined by $^1$H NMR integrations of olefinic peaks in crude reaction mixture. Product also verified by MS and DEPT 135.

1,6-Dioxa-cyclopentadec-3-ene: 30 mg (0.141 mmol) of diene and 5 mol % of catalyst were dissolved in 10 mL each of solvent and added slowly (1 drop per second) through a dropping funnel to 5 mL of refluxing solvent. The resulting mixture was then refluxed for a total of 3 hours, for Ru(OC$_6$F$_5$)$_2$(CHPh)(py)(IMes) total reaction time is 18 hours. After reaction the solvent is removed under vacuum and dissolved in CDCl$_3$ for NMR analysis and GC-MS.

The results are shown below:

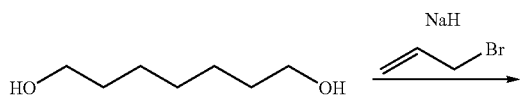

-continued

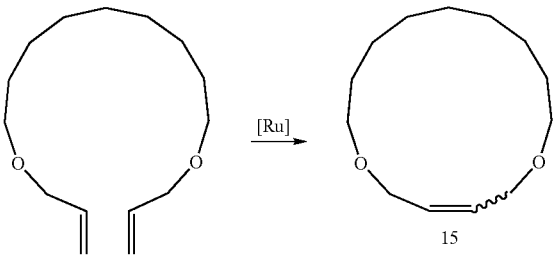

1,6-dioxacyclohexadec-3-ene
GC-MS, ¹H NMR and DEPT, NOE, TOCSY, COSY

| Literature: [Ru] 28% yield 24 hours 90% E | IMes‸‸Ru(Cl)(Cl)(py)(py)=CHPh | IMes‸‸Ru(OC₆F₅)(OC₆F₅)(py)=CHPh | IMes‸‸Ru(OC₆Cl₅)(Cl)(py)=CHPh | IMes‸‸Ru(OC₆Br₅)(Cl)(py)=CHPh |
|---|---|---|---|---|
| | 99% conv. 55% Z 3 hours Benzene | 99% conv. 59% Z 17 hours toluene | 99% conv. 58% Z 3 hours Benzene | 95% conv. 61% Z 3 hours Benzene |

Controlling the E/Z stereochemistry of ring closed macrocycles is important. Often in RCM there is no selectivity and the desired product may be the minor isomer. Generally the most difficult isomer to obtain is the Z isomer. Typically macrocyclized products are 50/50 mixtures or are slightly enriched in E. So far the only reliable methods for obtaining Z products are by synthesizing diazo tethers and closing with ill defined metal catalyzed reactions. This is especially more difficult to perform on more complex substrates. Other examples of Z selective cyclizations include the tailoring of substrate, such as functional group serics or chelation adding unnecessary steps to substrate production. There exists no general method for selective ring closing reactions. Part of the problem lies in the complex nature of the intermediates, there exists four possible metallocyclobutane intermediates for $C_2$ catalysts and 8 for unsymmetrical catalysts. In a general scheme it is apparent that there are two opportunities for the substrate to alter its orientation to accommodate the least sterically demanding conformation. The new catalysts accomplish selectivity by increasing the steric definition around the catalytic pocket.

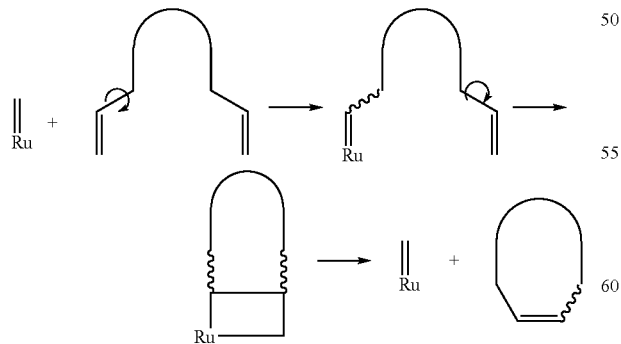

In the Grubbs systems of the prior art, the intermediates show no bias toward either E or Z: no steric discrimination occurs, resulting in the observed 1:1 E:Z mixture of products:

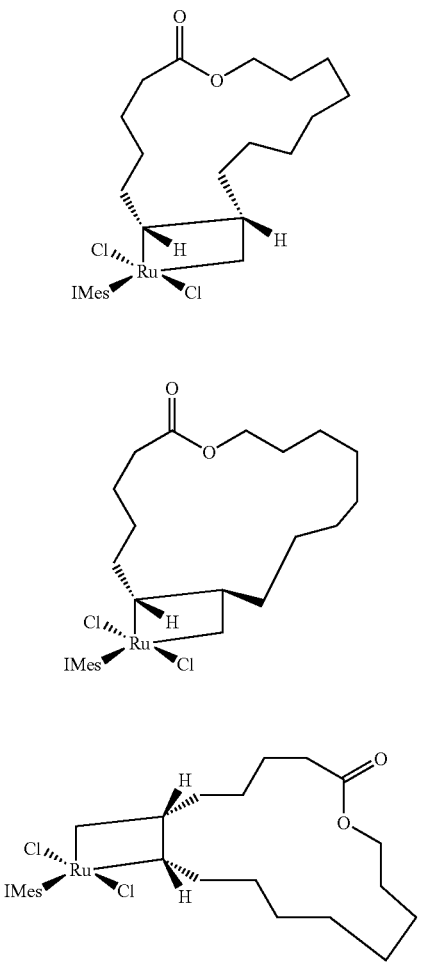

-continued

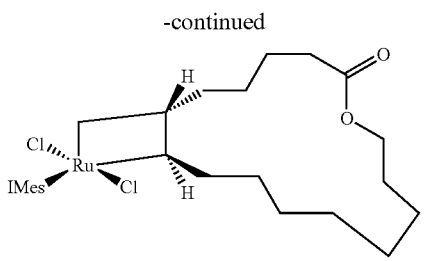

However in the Ru(OC$_6$F$_5$)$_2$(CHPh)(py)(IMes) system of the present invention, steric pressure in the intermediate, arising from the unsymmetically disposed OAr and IMes groups, confers an E/Z bias, resulting in a 2:1 E:Z ratio in the product. Since there are 8 possible intermediates. the selectivity is not perfect: in the intermediates that begin with apical methylidene, the substrate is further away from the IMes and OArF groups, and may limit the selectivity.

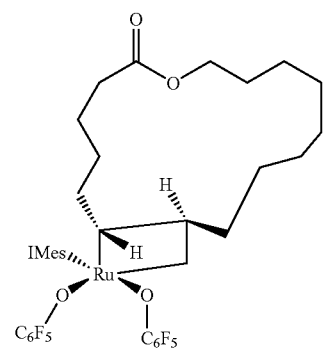

Intermediate for E

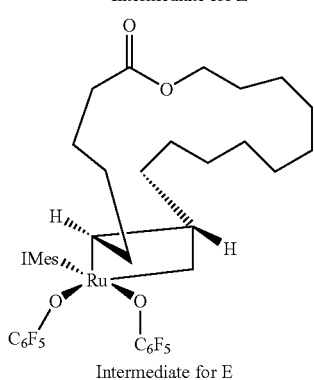

Intermediate for Z

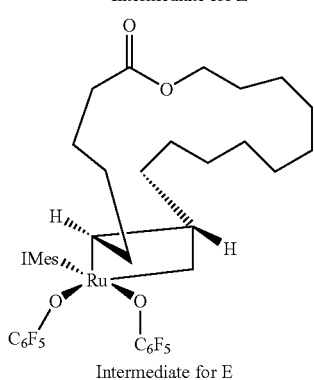

Intermediate for E

-continued

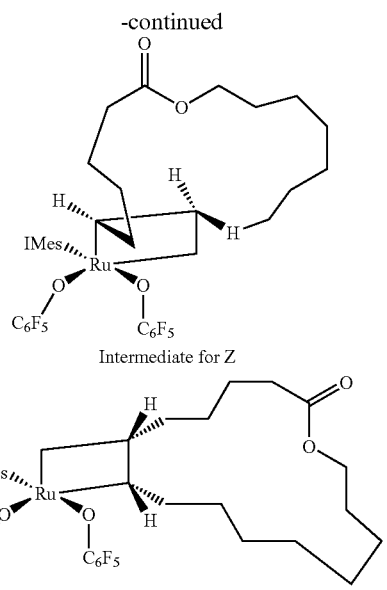

Intermediate for Z

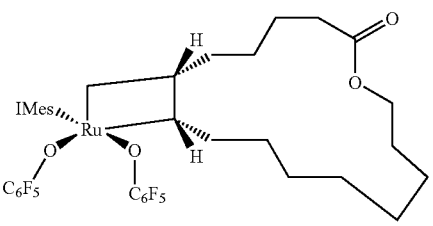

Intermediate for Z

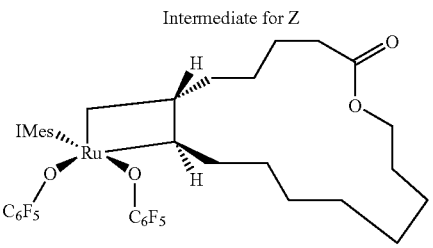

Intermediate for E

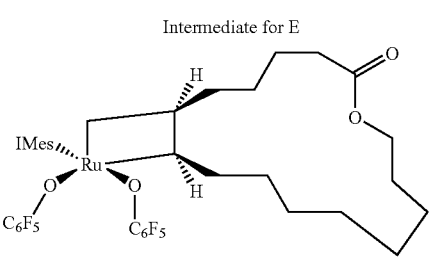

Intermediate for Z

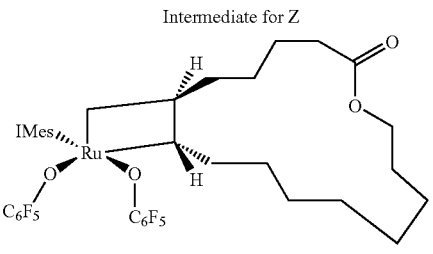

Intermediate for E

The real intermediate probably lies between these extremes but for simplicity exact square pyramids have been depicted. On the other extreme both mono substituted pseudohalide catalysts Ru(OC$_6$Cl$_5$)Cl(CHPh)(IMes)(py) and Ru(OC$_6$Br$_5$)Cl(CHPh)(py)(IMes) give products enriched in Z. Again the steric requirements of the intermediates may account for this selectivity. In these two cases it is unknown whether the OC$_6$X$_5$ group is cis or trans to IMes. Nevertheless, it is apparent that increasing the steric bulk around the active site has an impact on product stereochemistry. In the monosubstituted compounds this results in Z-selective ring closing of macrocycles.
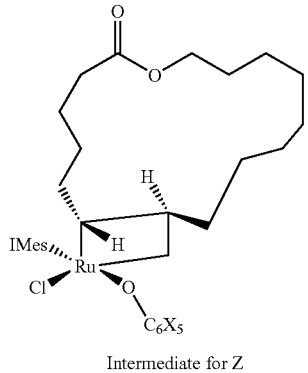
Intermediate for Z
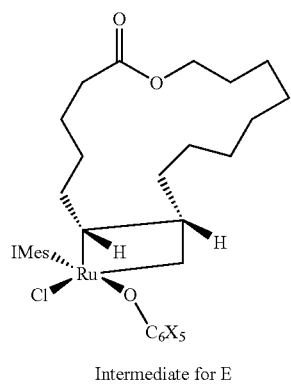
Intermediate for E
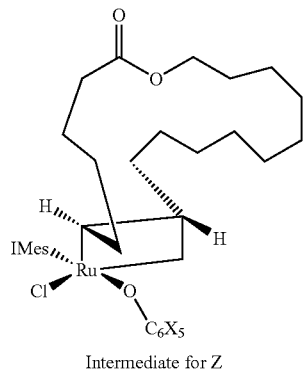
Intermediate for Z
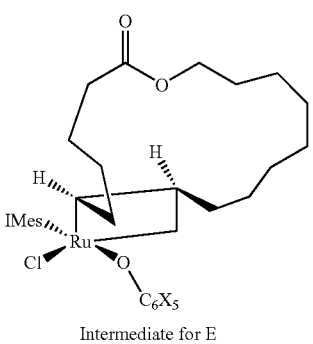
Intermediate for E
-continued
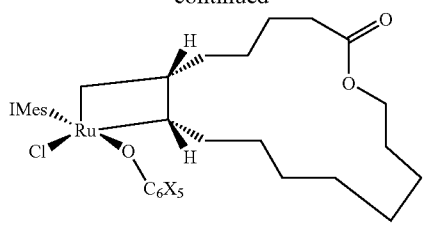
Intermediate for E
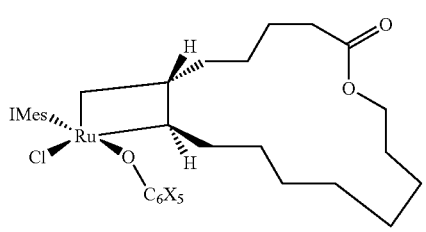
Intermediate for Z
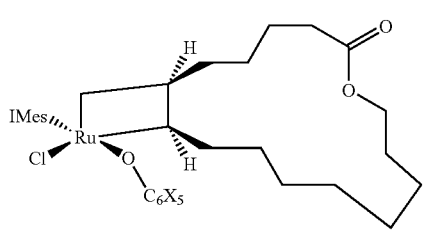
Intermediate for E
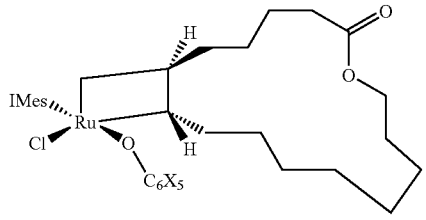
Intermediate for Z
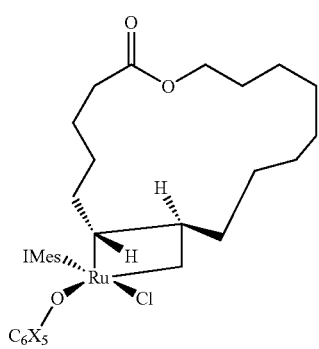
Intermediate for Z -continued

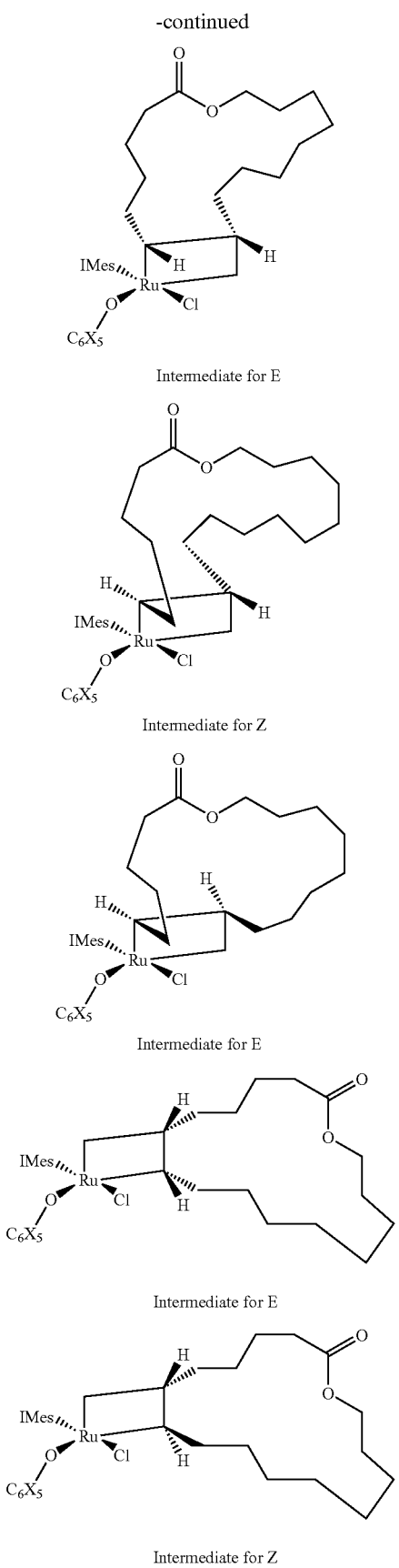

Intermediate for E

Intermediate for Z

Intermediate for E

Intermediate for E

Intermediate for Z

-continued

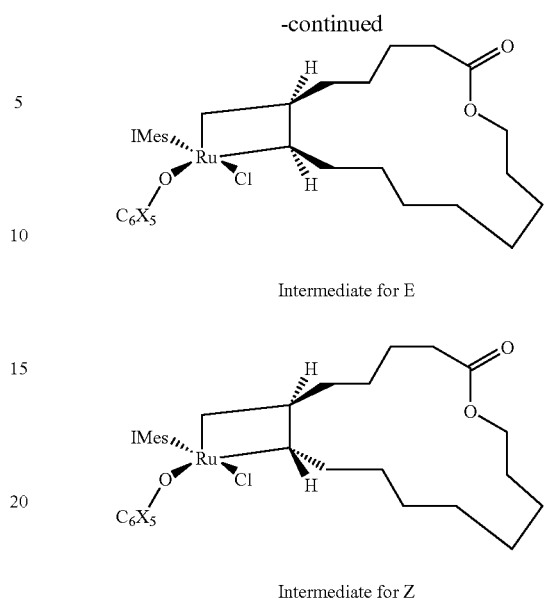

Intermediate for E

Intermediate for Z

A similar trend is observed for formation of 15 membered macrocycles. In this case, there is minimal functional group bias to aid in directing E or Z formation, only two (symmetrically disposed) ether groups. Selectivity with Ru(OC$_6$Br$_5$)Cl(CHPh)(py)(IMes) is 60% Z.

Example 12

Analysis of Pyridine Lability with the Compounds of the Present Invention

Figure 7:
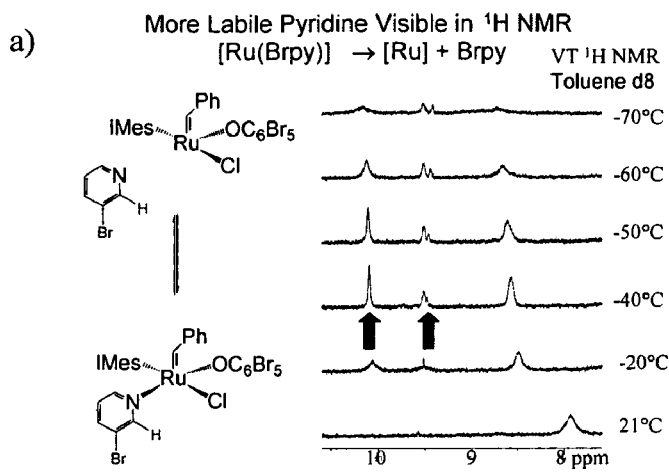
FIG. 7 illustrates $^1$HNMR analysis to compare the lability of pyridine neutral ligands with Ru.
Figure 7:
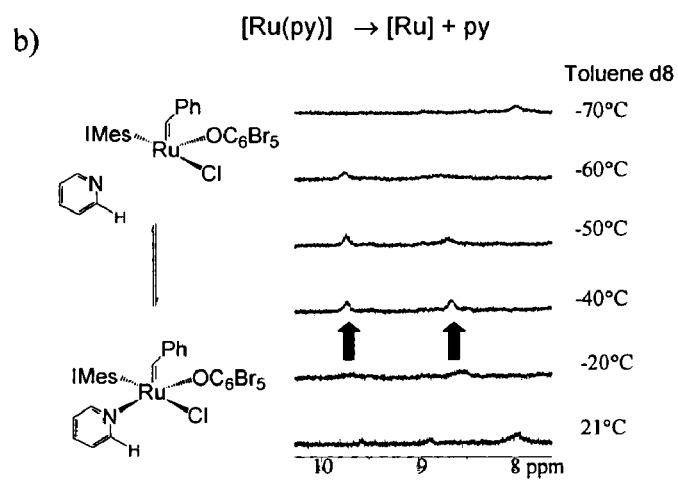
Figure 7:
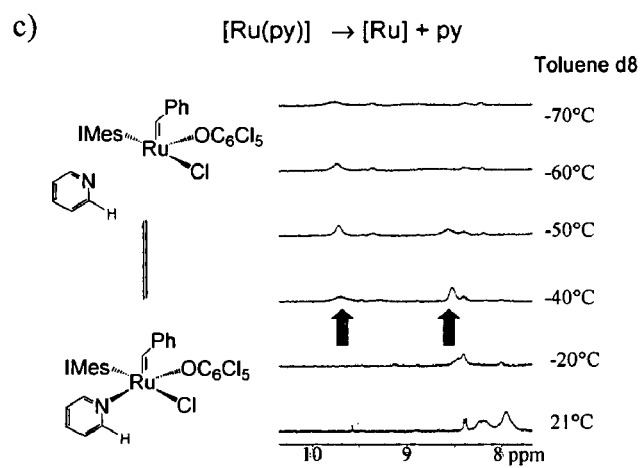

Without wishing to be bound by theory, the compounds of the present invention are predicted to operate as catalysts by the incorporation of a very broad range of neutral ligands. However, pyridine is a particularly preferred ligand by virtue of the lability of the pyridine-Ru dative bond, and the apparent lack of interference of the pyridine with catalytic activity. The inventors have conducted analysis of the temperature dependent lability of the pyridine-Ru interaction with various compounds of the present invention, as shown in FIG. 7.

Reactions were conducted in toluene, and $^1$H NMR was used to study the equilibrium between pyridine-Ru interaction at various temperatures. The vertically oriented arrows indicate the positions of the expected peaks for pyridine, which sharpen upon cooling, presumably due to dissociation of pyridine from Ru. FIG. 7a relates to the dissociation of the 3-Br-pyridine ligand from Ru(OC$_6$Br$_5$)Cl(CHPh)(IMes). The notable sharpening of the peaks upon cooling to $-40°$ C. indicates increased lability of the 3-Br-pyridine bond with Ru(OC$_6$Br$_5$)Cl(CHPh)(IMes). This contrasts directly with the results for unsubstituted pyridine from either Ru(OC$_6$Br$_5$)Cl(CHPh)(IMes)(FIG. 7b) or Ru(OC$_6$Cl$_5$)Cl(CHPh)(IMes)(FIG. 7c). The peaks do not sharpen until lower temperature in the same manner as in FIG. 7a suggesting decreased lability of the pyridine-Ru interaction.

These results indicate that the presence of the Br as an electron-withdrawing substituent on the pyridine increases the capacity of the pyridine for dissociation from the Ru atom, which in turn correlates with the observed increase in catalytic activity for complexes containing 3-Br-pyridine.

Example 13

Cross-Metathesis with Ru(OC$_6$F$_5$)$_2$(CHPh)(IMes)(py)

Ru(OC$_6$F$_5$)$_2$(CHPh)(IMes)(py) was used to test for the capacity of the compounds of the present invention to catalyze cross-metathesis reactions. Standard conditions were used to test the capacity of Ru(OC$_6$F$_5$)$_2$(CHPh)(IMes)(py) in the following cross-metathesis reactions:

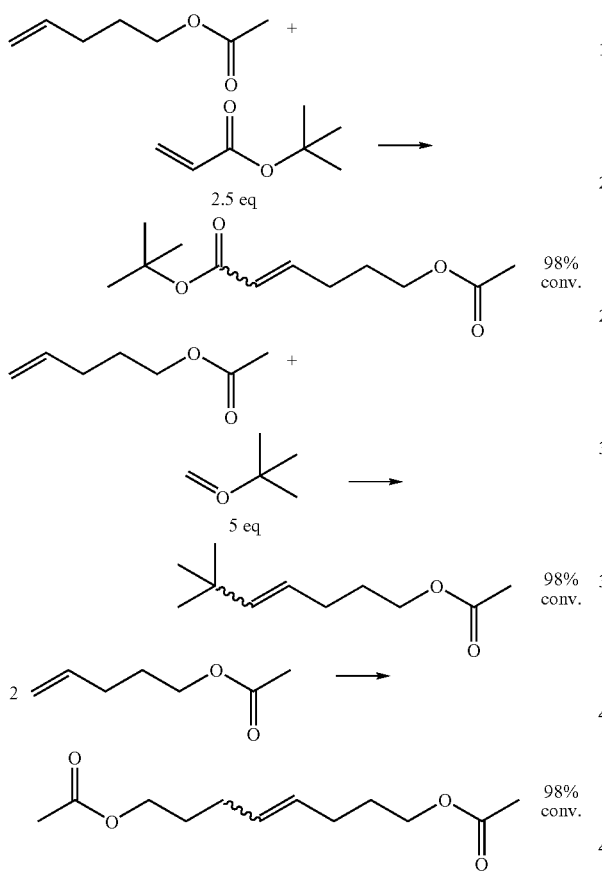

Under standard conditions with 0.1M substrate, 5 mol % catalyst, refluxing CDCl$_3$, the catalyst was capable of achieving almost 100% conversion, thereby demonstrating the capacity of the compounds of the present invention to catalyze cross-metathesis reactions.

Example 14

Production and Crystallographic Data for Ru(O$_2$C$_{20}$H$_4$F$_8$)(CHPh)(IMes)(py)

The inventors have succeeded in the production of a Ru compound encompassed by formula I, which includes a multidentate anionic ligand. Effectively, the multidentate anionic ligand comprises two fluorinated binaphtholate groups tethered together by a covalent link. The compound in question, designated Ru(O$_2$C$_{20}$H$_4$F$_8$)(CHPh)(IMes)(py), is illustrated below:

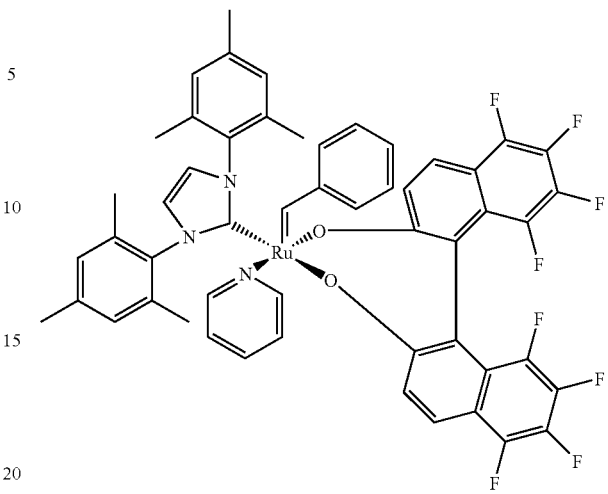

Crystallographic data for this compound is shown after the examples.

Figure 8:
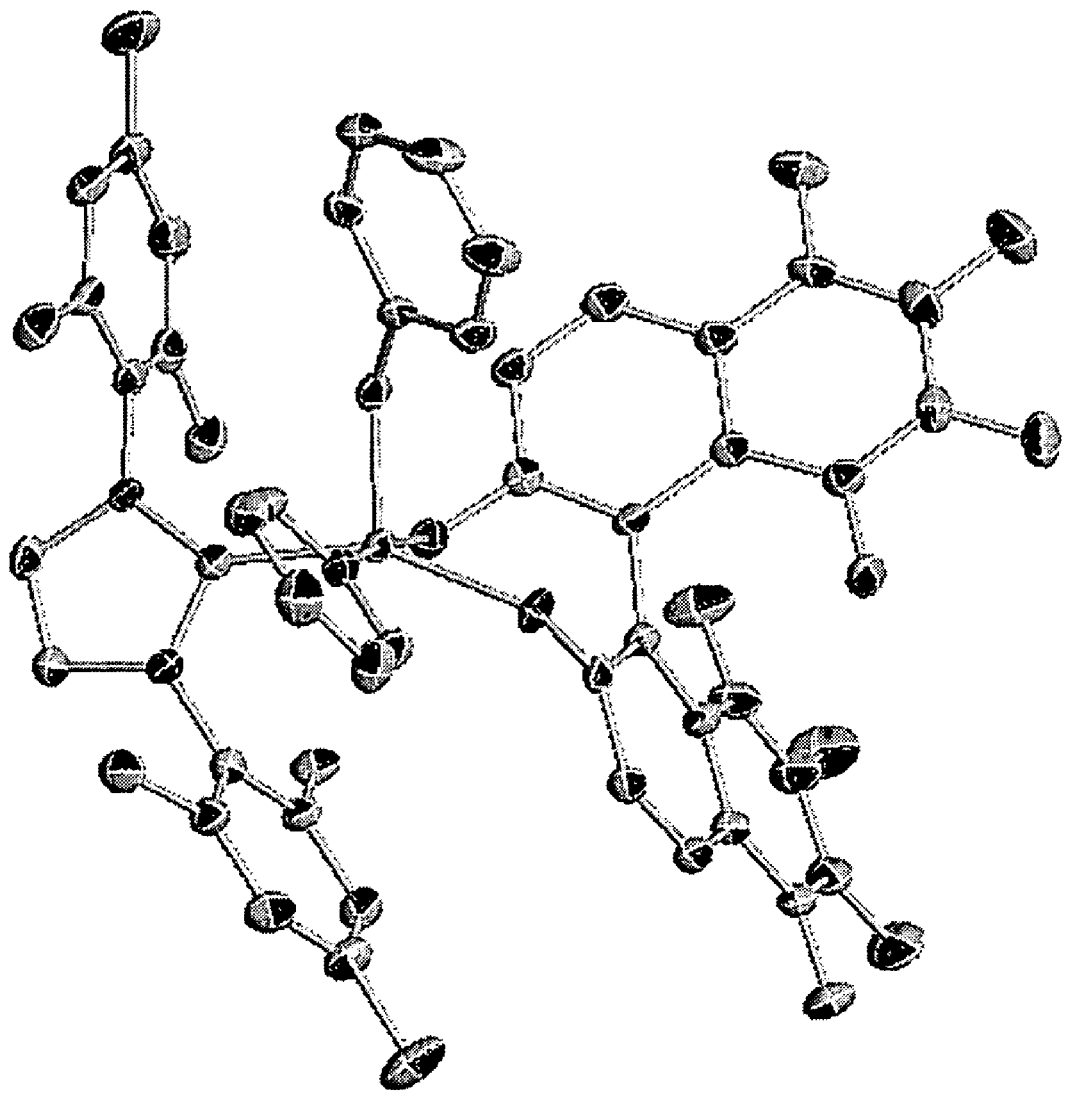
FIG. 8 provides Oak Ridge Thermal Ellipsoid Plot Program for Crystal Structure Illustrations (ORTEP) representations of the compound $Ru(O_2C_{20}H_4F_8)(CHPh)(IMes)$ (py)—(compound 14); hydrogen atoms and solvates have been omitted. Thermal ellipsoids at 30% probability level.

The inventors have further succeeded in generating X-ray crystal structure data for Ru(O$_2$C$_{20}$H$_4$F$_8$)(CHPh)(IMes)(py) as shown in FIG. 8.

The capacity of Ru(O$_2$C$_{20}$H$_4$F$_8$)(CHPh)(IMes)(py) to catalyze ROMP of cyclooctene was also tested. A surprisingly high conversion rate was observed (see Example 7 and FIG. 4, F8binol/py).

Example 15

Figure 9:
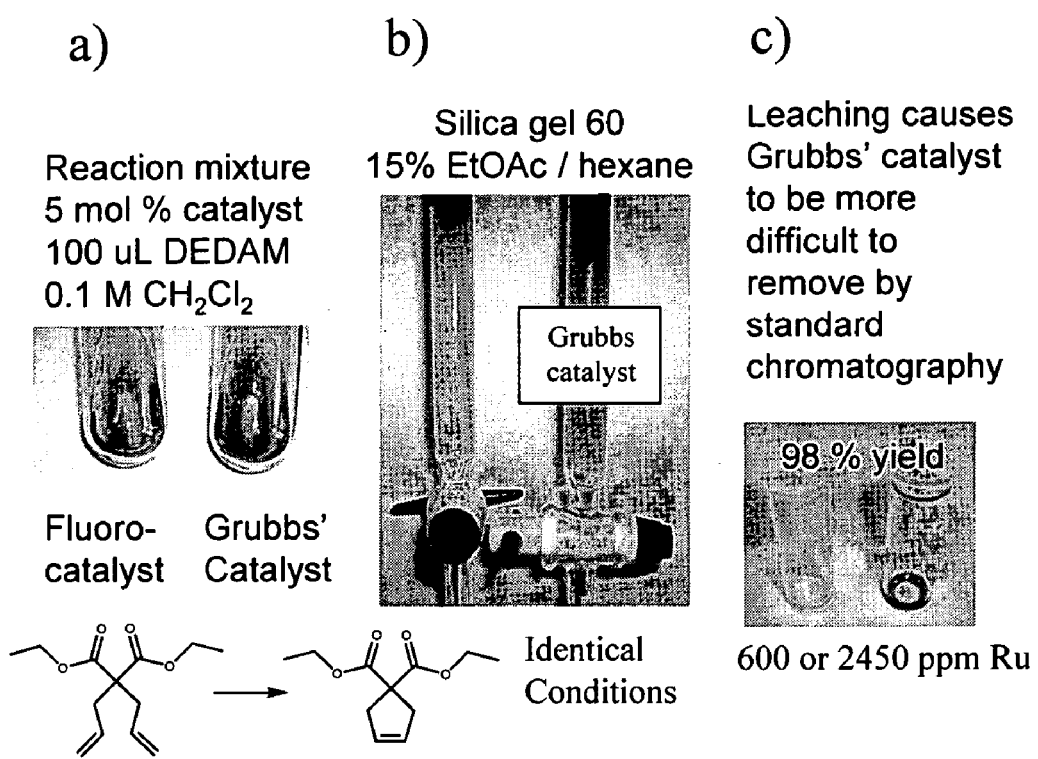
FIG. 9a provides photographs to compare reaction mixtures using diethyldiallyl malonate as a substrate, for a catalyst compound of the present invention (left) to a Grubbs catalyst (right).
FIG. 9b provides photographs to compare column chromatography purification of a catalyst compound of the present invention (left) to a Grubbs catalyst (right).
FIG. 9c provides photographs to compare the isolated ring closed product as an oil after column chromatography using the present invention (left) and Grubbs' catalyst (right). The dark color represents transition metal impurities.

Improved Chromatographic Purification of the Compounds of the Present Invention RCM reactions were conducted for the "benchmark substrate" diethyldiallyl malonate under conditions as previously described, but using 5 mol % Ru(OC$_6$F$_5$)$_2$(CHPh)(IMes)(py) or the Grubbs first generation catalyst RuCl$_2$(PCy$_3$)$_2$(CHPh), using 100 μL substrate, 0.1 M CH$_2$Cl$_2$ and purifying the product with identical chromatography conditions to obtain 98% yield. The reaction mixtures are shown in FIG. 9a, and the chromatography columns are shown in FIG. 9b: the column with the compound of the present invention on the left, that with the Grubbs catalyst on the right. The organic solvent used in chromatography was evaporated off to obtain the product as an oil-based product (see comparison photo of vials in FIG. 9c). Again, the oil-based product obtained using the catalyst of the present invention is shown at left, Grubbs catalyst on the right. The results of the experiment give a colourless organic oil-based product for the compound of the present invention, whereas the oil-based product from the experiment using Grubbs catalyst is black, showing high residues of decomposed Ru even after chromatography. Quantification by ICPMS revealed only 600 ppm of residue ruthenium using the present invention and 2450 ppm using prior art in the product. It may be noted that this experiment was optimized for purification of the inferior (Grubbs) system, and that higher purities are therefore attainable using the catalyst of the present invention, for which smaller solvent volumes are required to effect complete recovery of the organic product.

The ease of separation is attributed to the difference in polarity as shown below:

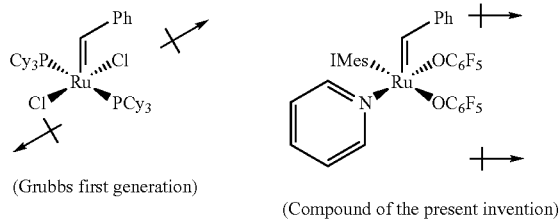

(Grubbs first generation)    (Compound of the present invention)

Tables of crystal data collection and refinement parameters atomic coordinates, bond lengths and angles, anisotropic displacement parameters and hydrogen coordinates.

TABLE 6

Crystal data and structure refinement for 4c, Ru($\equiv$CPh)(OC$_6$F$_5$)(PCy$_3$)$_2$

| | |
|---|---|
| Empirical formula | C$_{61}$H$_{83}$F$_5$OP$_2$Ru |
| Formula weight | 1090.28 |
| Temperature | 203(2) K |
| Wavelength | 0.71073 Å |
| Crystal system, space group | Triclinic, P-1 |
| Unit cell dimensions | a = 10.3672(11) Å α = 93.966(2)° |
| | b = 11.4682(12) Å β = 112.125(2)° |
| | c = 13.4815(14) Å γ = 99.494(2)° |
| Volume | 1449.3(3)Å$^3$ |
| Z, Calculated density | 1, 1.249 Mg/m$^3$ |
| Absorption coefficient | 0.380 mm$^{-1}$ |
| F(000) | 576 |
| Crystal size | 0.20 × 0.10 × 0.10 mm |
| Theta range for data collection | 1.82 to 28.39 deg. |
| Limiting indices | −13 <= h <= 12, −15 <= k <= 15, 0 <= l <= 17 |
| Reflections collected/unique | 12274/6402 [R(int) = 0.0289] |
| Completeness to theta | 28.39 88.2% |
| Absorption correction | Semi-empirical from equivalents |
| Max. and min. transmission | 1.000000 and 0.767622 |
| Refinement method | Full-matrix least-squares on F$^2$ |
| Data/restraints/parameters | 6402/0/349 |
| Goodness-of-fit on F$^2$ | 1.048 |
| Final R indices [I > 2sigma(I)] | R1 = 0.0438, wR2 = 0.1794 |
| R indices (all data) | R1 = 0.0456, wR2 = 0.1809 |
| Largest diff. peak and hole | 0.912 and −0.638 e.Å$^{-3}$ |

Definition of R indices: $R_1 = \Sigma(F_o - F_c)/\Sigma(F_o)$; $wR_2 = [\Sigma[w(F_o^2 - F_c^2)^2]/\Sigma[w(F_o^2)^2]]^{1/2}$

TABLE 7

Atomic coordinates (×10$^4$) and equivalent isotropic displacement parameters (A$^2$ × 10$^3$) for 4c. U(eq) is defined as one third of the trace of the orthogonalized Uij tensor.

| | x | y | z | U(eq) |
|---|---|---|---|---|
| Ru | 5000 | 5000 | 5000 | 21(1) |
| P(1) | 3944(1) | 4665(1) | 3054(1) | 25(1) |
| O(1) | 6012(16) | 3710(16) | 4988(15) | 48(4) |
| C(31) | 6180(30) | 3810(30) | 4940(30) | 68(9) |
| F(1) | 8882(6) | 4476(5) | 5225(4) | 49(1) |
| F(2) | 10599(6) | 2962(6) | 5244(6) | 63(2) |
| F(3) | 9636(8) | 514(6) | 5028(7) | 81(2) |
| F(4) | 6887(7) | −333(5) | 4803(6) | 63(2) |
| F(5) | 5163(6) | 1171(5) | 4810(5) | 51(1) |
| C(1) | 8350(5) | 3432(5) | 5116(4) | 49(1) |
| C(2) | 9226(6) | 2635(6) | 5122(4) | 61(2) |
| C(3) | 8763(7) | 1420(7) | 5026(5) | 68(2) |
| C(4) | 7377(7) | 968(5) | 4915(5) | 57(1) |
| C(5) | 6469(5) | 1755(5) | 4891(4) | 48(1) |
| C(6) | 6924(5) | 3012(4) | 4994(3) | 38(1) |
| C(7) | 6635(4) | 5265(4) | 2889(3) | 35(1) |
| C(8) | 7765(5) | 4793(5) | 2595(3) | 41(1) |
| C(9) | 7245(5) | 4419(5) | 1372(4) | 45(1) |
| C(10) | 5825(6) | 3514(5) | 929(4) | 49(1) |
| C(11) | 4698(5) | 3988(4) | 1234(3) | 41(1) |
| C(12) | 5235(4) | 4323(3) | 2478(3) | 29(1) |
| C(13) | 2976(5) | 2176(3) | 2821(4) | 40(1) |
| C(14) | 1747(5) | 1071(4) | 2440(4) | 48(1) |
| C(15) | 623(5) | 1261(4) | 2870(4) | 48(1) |
| C(16) | 44(5) | 2367(4) | 2497(4) | 44(1) |
| C(17) | 1257(4) | 3489(3) | 2876(4) | 37(1) |
| C(18) | 2448(4) | 3328(3) | 2484(3) | 29(1) |
| C(19) | 2105(6) | 5662(4) | 1234(3) | 46(1) |
| C(20) | 1312(6) | 6692(5) | 906(4) | 52(1) |
| C(21) | 2343(6) | 7894(5) | 1183(4) | 52(1) |
| C(22) | 3363(5) | 8123(4) | 2371(4) | 44(1) |
| C(23) | 4164(4) | 7094(3) | 2692(4) | 36(1) |
| C(24) | 3096(4) | 5897(3) | 2443(3) | 30(1) |
| C(25) | 6815(8) | 9869(7) | 912(7) | 83(2) |
| C(26) | 6782(8) | 9610(9) | 1888(9) | 102(3) |
| C(27) | 7446(11) | 8739(9) | 2372(7) | 104(3) |
| C(28) | 8177(10) | 8153(6) | 1879(8) | 99(3) |
| C(29) | 8205(9) | 8429(6) | 900(7) | 82(2) |
| C(30) | 7515(9) | 9287(6) | 444(6) | 78(2) |

TABLE 8

Bond lengths [Å] and angles [°] for 4c.

| | | | |
|---|---|---|---|
| Ru—C(31) | 2.00(3) | Ru—C(31)#1 | 2.00(3) |
| Ru—O(1) | 1.953(14) | Ru—O(1)#1 | 1.953(14) |
| Ru—P(1) | 2.4063(9) | Ru—P(1)#1 | 2.4063(9) |
| P(1)-C(12) | 1.861(4) | P(1)-C(24) | 1.864(4) |
| P(1)-C(18) | 1.871(4) | O(1)-C(6) | 1.333(13) |
| C(31)-C(6) | 1.28(3) | F(1)-C(1) | 1.207(8) |
| F(2)-C(2) | 1.354(8) | F(3)-C(3) | 1.485(7) |

TABLE 8-continued

Bond lengths [Å] and angles [°] for 4c.

| | | | |
|---|---|---|---|
| F(3)-F(3)#2 | 1.514(10) | F(4)-C(4) | 1.473(8) |
| F(5)-C(5) | 1.368(8) | C(1)-C(2) | 1.389(7) |
| C(1)-C(6) | 1.420(7) | C(2)-C(3) | 1.378(10) |
| C(3)-C(4) | 1.391(9) | C(4)-C(5) | 1.401(7) |
| C(5)-C(6) | 1.421(7) | C(7)-C(8) | 1.534(6) |
| C(7)-C(12) | 1.541(5) | C(8)-C(9) | 1.534(6) |
| C(9)-C(10) | 1.533(7) | C(10)-C(11) | 1.539(6) |
| C(11)-C(12) | 1.552(5) | C(13)-C(14) | 1.542(6) |
| C(13)-C(18) | 1.545(5) | C(14)-C(15) | 1.522(7) |
| C(15)-C(16) | 1.528(6) | C(16)-C(17) | 1.546(6) |
| C(17)-C(18) | 1.546(5) | C(19)-C(24) | 1.540(5) |
| C(19)-C(20) | 1.545(6) | C(20)-C(21) | 1.524(8) |
| C(21)-C(22) | 1.526(7) | C(22)-C(23) | 1.547(5) |
| C(23)-C(24) | 1.542(5) | C(25)-C(30) | 1.348(12) |
| C(25)-C(26) | 1.380(13) | C(26)-C(27) | 1.370(14) |
| C(27)-C(28) | 1.398(14) | C(28)-C(29) | 1.387(13) |
| C(29)-C(30) | 1.357(11) | | |
| C(31)-Ru—C(31)#1 | 180.000(8) | C(31)-Ru—O(1) | 6.3(11) |
| C(31)#1-Ru—O(1) | 173.7(11) | C(31)-Ru—O(1)#1 | 173.7(11) |
| C(31)#1-Ru—O(1)#1 | 6.3(11) | O(1)-Ru—O(1)#1 | 180.000(5) |
| C(31)-Ru—P(1) | 88.3(10) | C(31)#1-Ru—P(1) | 91.7(10) |
| O(1)-Ru—P(1) | 89.7(5) | O(1)#1-Ru—P(1) | 90.3(5) |
| C(31)-Ru—P(1)#1 | 91.7(10) | C(31)#1-Ru—P(1)#1 | 88.3(10) |
| O(1)-Ru—P(1)#1 | 90.3(5) | O(1)#1-Ru—P(1)#1 | 89.7(5) |
| P(1)-Ru—P(1)#1 | 180.0 | C(12)-P(1)-C(24) | 111.11(17) |
| C(12)-P(1)-C(18) | 103.49(17) | C(24)-P(1)-C(18) | 102.92(17) |
| C(12)-P(1)-Ru | 111.57(12) | C(24)-P(1)-Ru | 113.73(12) |
| C(18)-P(1)-Ru | 113.28(12) | C(6)-O(1)-Ru | 168.1(13) |
| C(6)-C(31)-Ru | 174(2) | C(3)-F(3)-F(3)#2 | 173.4(11) |
| F(1)-C(1)-C(2) | 115.8(6) | F(1)-C(1)-C(6) | 123.5(5) |
| C(2)-C(1)-C(6) | 120.6(5) | F(2)-C(2)-C(3) | 113.8(6) |
| F(2)-C(2)-C(1) | 124.3(7) | C(3)-C(2)-C(1) | 121.9(5) |
| C(2)-C(3)-C(4) | 119.5(5) | C(2)-C(3)-F(3) | 125.0(6) |
| C(4)-C(3)-F(3) | 115.5(7) | C(3)-C(4)-C(5) | 119.6(6) |
| C(3)-C(4)-F(4) | 119.1(5) | C(5)-C(4)-F(4) | 121.3(6) |
| F(5)-C(5)-C(4) | 112.1(5) | F(5)-C(5)-C(6) | 125.8(5) |
| C(4)-C(5)-C(6) | 122.0(5) | O(1)-C(6)-C(31) | 9.4(17) |
| O(1)-C(6)-C(1) | 124.7(9) | C(31)-C(6)-C(1) | 116.0(12) |
| O(1)-C(6)-C(5) | 118.8(8) | C(31)-C(6)-C(5) | 127.5(13) |
| C(1)-C(6)-C(5) | 116.4(4) | C(8)-C(7)-C(12) | 110.8(3) |
| C(7)-C(8)-C(9) | 111.6(3) | C(10)-C(9)-C(8) | 111.3(4) |
| C(9)-C(10)-C(11) | 111.4(4) | C(10)-C(11)-C(12) | 110.8(4) |
| C(7)-C(12)-C(11) | 109.3(3) | C(7)-C(12)-P(1) | 113.9(3) |
| C(11)-C(12)-P(1) | 118.4(3) | C(14)-C(13)-C(18) | 112.1(4) |
| C(15)-C(14)-C(13) | 110.5(4) | C(14)-C(15)-C(16) | 110.5(4) |
| C(15)-C(16)-C(17) | 110.8(4) | C(18)-C(17)-C(16) | 111.8(3) |
| C(13)-C(18)-C(17) | 110.1(3) | C(13)-C(18)-P(1) | 110.9(3) |
| C(17)-C(18)-P(1) | 109.8(2) | C(24)-C(19)-C(20) | 111.2(4) |
| C(21)-C(20)-C(19) | 111.7(4) | C(20)-C(21)-C(22) | 111.5(4) |
| C(21)-C(22)-C(23) | 111.9(4) | C(24)-C(23)-C(22) | 110.3(3) |
| C(19)-C(24)-C(23) | 109.7(3) | C(19)-C(24)-P(1) | 118.0(3) |
| C(23)-C(24)-P(1) | 113.2(3) | C(30)-C(25)-C(26) | 120.6(8) |
| C(27)-C(26)-C(25) | 119.5(9) | C(26)-C(27)-C(28) | 119.1(8) |
| C(29)-C(28)-C(27) | 120.6(8) | C(30)-C(29)-C(28) | 118.2(8) |
| C(25)-C(30)-C(29) | 122.0(8) | | |

Symmetry transformations used to generate equivalent atoms:
1 −x + 1, −y + 1, −z + 1
2 −x + 2, −y, −z + 1

TABLE 9

Anisotropic displacement parameters ($Å^2 \times 10^3$) for 4c.
The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| Ru | 26(1) | 18(1) | 22(1) | 4(1) | 10(1) | 8(1) |
| P(1) | 29(1) | 22(1) | 23(1) | 4(1) | 10(1) | 6(1) |
| O(1) | 30(5) | 96(12) | 29(5) | 11(6) | 18(4) | 27(6) |
| C(31) | 69(14) | 74(13) | 39(10) | 21(9) | 13(8) | −31(10) |
| F(1) | 62(3) | 32(3) | 43(3) | 6(2) | 12(2) | 8(2) |
| F(2) | 42(3) | 72(4) | 81(4) | 11(3) | 25(3) | 23(3) |
| F(3) | 91(5) | 64(4) | 122(6) | 32(4) | 53(5) | 70(4) |
| F(4) | 77(4) | 28(3) | 93(5) | 15(3) | 37(4) | 25(3) |
| F(5) | 50(3) | 44(3) | 63(3) | 15(3) | 24(3) | 13(2) |
| C(1) | 45(2) | 72(3) | 33(2) | 8(2) | 14(2) | 23(2) |
| C(2) | 45(3) | 97(5) | 49(3) | 12(3) | 19(2) | 34(3) |
| C(3) | 65(4) | 85(4) | 68(4) | 12(3) | 28(3) | 49(3) |

TABLE 9-continued

Anisotropic displacement parameters ($A^2 \times 10^3$) for 4c.
The anisotropic displacement factor exponent takes the form:
$-2 pi^2 [h^2 a^{*2} U11 + \ldots + 2 h k a^* b^* U12]$

|  | U11 | U22 | U33 | U23 | U13 | U12 |
|---|---|---|---|---|---|---|
| C(4) | 72(3) | 53(3) | 56(3) | 12(2) | 27(3) | 30(3) |
| C(5) | 48(2) | 64(3) | 39(2) | 11(2) | 18(2) | 23(2) |
| C(6) | 43(2) | 54(2) | 23(2) | 8(2) | 12(2) | 24(2) |
| C(7) | 34(2) | 38(2) | 31(2) | 4(2) | 13(2) | 7(2) |
| C(8) | 36(2) | 58(3) | 34(2) | 10(2) | 17(2) | 16(2) |
| C(9) | 47(2) | 65(3) | 36(2) | 13(2) | 25(2) | 22(2) |
| C(10) | 61(3) | 57(3) | 35(2) | −3(2) | 26(2) | 13(2) |
| C(11) | 39(2) | 55(3) | 28(2) | −2(2) | 14(2) | 6(2) |
| C(12) | 35(2) | 31(2) | 25(2) | 5(1) | 14(1) | 9(1) |
| C(13) | 41(2) | 22(2) | 56(3) | 4(2) | 20(2) | 7(2) |
| C(14) | 52(3) | 26(2) | 62(3) | 0(2) | 21(2) | 3(2) |
| C(15) | 48(2) | 28(2) | 65(3) | 7(2) | 24(2) | −4(2) |
| C(16) | 35(2) | 36(2) | 58(3) | 5(2) | 17(2) | 2(2) |
| C(17) | 34(2) | 28(2) | 49(2) | 3(2) | 18(2) | 6(2) |
| C(18) | 32(2) | 25(2) | 29(2) | 1(1) | 10(1) | 3(1) |
| C(19) | 60(3) | 36(2) | 32(2) | 7(2) | 3(2) | 18(2) |
| C(20) | 54(3) | 51(3) | 43(2) | 14(2) | 4(2) | 24(2) |
| C(21) | 74(3) | 44(2) | 48(3) | 23(2) | 24(2) | 30(2) |
| C(22) | 55(3) | 29(2) | 52(3) | 13(2) | 22(2) | 15(2) |
| C(23) | 40(2) | 25(2) | 43(2) | 12(2) | 16(2) | 9(2) |
| C(24) | 35(2) | 26(2) | 27(2) | 6(1) | 11(1) | 10(1) |
| C(25) | 60(4) | 73(4) | 94(5) | 15(4) | 8(4) | 7(3) |
| C(26) | 59(4) | 112(7) | 125(8) | −22(6) | 47(5) | −21(4) |
| C(27) | 111(7) | 94(6) | 75(5) | 11(4) | 31(5) | −54(6) |
| C(28) | 97(6) | 45(3) | 104(6) | 23(3) | −8(5) | −14(4) |
| C(29) | 88(5) | 55(4) | 83(5) | −12(3) | 22(4) | 0(3) |
| C(30) | 92(5) | 67(4) | 55(3) | 4(3) | 14(3) | −3(4) |

TABLE 10

Hydrogen coordinates ($\times 10^4$) and isotropic displacement parameters
($A^2 \times 10^3$) for 4c.

|  | x | y | z | U(eq) |
|---|---|---|---|---|
| H(1A) | 8704 | 4256 | 5194 | 59 |
| H(2A) | 10162 | 2934 | 5194 | 73 |
| H(3A) | 9378 | 900 | 5035 | 82 |
| H(4A) | 7053 | 141 | 4856 | 69 |
| H(5A) | 5530 | 1441 | 4805 | 58 |
| H(7A) | 6457 | 5993 | 2567 | 41 |
| H(7B) | 6986 | 5469 | 3677 | 41 |
| H(8A) | 7999 | 4106 | 2969 | 49 |
| H(8B) | 8633 | 5416 | 2843 | 49 |
| H(9A) | 7130 | 5126 | 1005 | 54 |
| H(9B) | 7960 | 4064 | 1218 | 54 |
| H(10A) | 5970 | 2765 | 1222 | 59 |
| H(10B) | 5482 | 3344 | 140 | 59 |
| H(11A) | 3819 | 3375 | 972 | 49 |
| H(11B) | 4483 | 4693 | 883 | 49 |
| H(12A) | 5518 | 3596 | 2774 | 35 |
| H(13A) | 3668 | 2048 | 2513 | 47 |
| H(13B) | 3461 | 2275 | 3611 | 47 |
| H(14A) | 1315 | 924 | 1647 | 58 |
| H(14B) | 2119 | 368 | 2696 | 58 |
| H(15A) | 1041 | 1359 | 3662 | 58 |
| H(15B) | −158 | 558 | 2610 | 58 |
| H(16A) | −665 | 2484 | 2791 | 53 |
| H(16B) | −427 | 2247 | 1705 | 53 |
| H(17A) | 867 | 4178 | 2598 | 44 |
| H(17B) | 1661 | 3653 | 3668 | 44 |
| H(18A) | 2056 | 3257 | 1685 | 35 |
| H(19A) | 1411 | 4913 | 1085 | 55 |
| H(19B) | 2667 | 5576 | 800 | 55 |
| H(20A) | 735 | 6541 | 126 | 62 |
| H(20B) | 669 | 6719 | 1281 | 62 |
| H(21A) | 1803 | 8532 | 1028 | 62 |
| H(21B) | 2890 | 7910 | 727 | 62 |
| H(22A) | 2827 | 8216 | 2824 | 52 |
| H(22B) | 4056 | 8871 | 2507 | 52 |

TABLE 10-continued

Hydrogen coordinates ($\times 10^4$) and isotropic displacement parameters
($A^2 \times 10^3$) for 4c.

|  | x | y | z | U(eq) |
|---|---|---|---|---|
| H(23A) | 4772 | 7046 | 2289 | 43 |
| H(23B) | 4774 | 7254 | 3465 | 43 |
| H(24A) | 2473 | 6037 | 2825 | 35 |
| H(25A) | 6346 | 10455 | 571 | 100 |
| H(26A) | 6307 | 10028 | 2218 | 123 |
| H(27A) | 7411 | 8538 | 3027 | 125 |
| H(28A) | 8653 | 7566 | 2213 | 119 |
| H(29A) | 8688 | 8032 | 563 | 98 |
| H(30A) | 7527 | 9481 | −219 | 94 |

TABLE 11

Crystal data and structure refinement for 5.

| Empirical formula | $C_{48}H_{38}F_{10}N_3O_2Ru$ |
|---|---|
| Formula weight | 979.88 |
| Temperature | 203(2) K |
| Wavelength | 0.71073 Å |
| Crystal system, space group | Triclinic, P-1 |
| Unit cell dimensions | α = 10.3425(13) Å  alpha = 81.473(2) |
|  | β = 13.0063(17) Å  beta = 72.540(2) |
|  | γ = 16.638(2) Å  gamma = 85.148(2) |
| Volume | 2109.4(5) $Å^3$ |
| Z, Calculated density | 2, 1.543 $Mg/m^3$ |
| Absorption coefficient | 0.460 $mm^{-1}$ |
| F(000) | 994 |
| Crystal size | 0.10 × 0.05 × 0.05 mm |
| Theta range for data collection | 1.58 to 28.87 deg. |
| Limiting indices | −9 <= h <= 13, −17 <= k <= 16, −21 <= l <= 22 |
| Reflections collected/unique | 11312/8648 [R(int) = 0.0287] |
| Completeness to theta = 28.87 | 78.0% |
| Absorption correction | Semi-empirical from equivalents |
| Max. and min. transmission | 0.9774 and 0.9554 |
| Refinement method | Full-matrix least-squares on $F^2$ |
| Data/restraints/parameters | 8648/0/577 |
| Goodness-of-fit on $F^2$ | 1.003 |
| Final R indices [I > 2sigma(I)] | R1 = 0.0487, wR2 = 0.0973 |
| R indices (all data) | R1 = 0.0826, wR2 = 0.1097 |
| Largest diff. peak and hole | 0.496 and −0.765 $e.A^{-3}$ |

Definition of R indices: $R_1 = \Sigma(F_o - F_c)/\Sigma(F_o); wR_2 = [\Sigma[w(F_o^2 - F_c^2)^2]/\Sigma[w(F_o^2)^2]]^{1/2}$

TABLE 12

Atomic coordinates ($\times 10^4$) and equivalent isotropic displacement
parameters ($A^2 \times 10^3$) for 5. U(eq) is defined as one third of
the trace of the orthogonalized Uij tensor.

|  | x | y | z | U(eq) |
|---|---|---|---|---|
| Ru | 4129(1) | 2359(1) | 2477(1) | 22(1) |
| F(1) | 3920(2) | 212(2) | 2448(2) | 40(1) |
| F(2) | 2572(3) | −1433(2) | 2319(2) | 50(1) |
| F(3) | −70(3) | −1678(2) | 3236(2) | 47(1) |
| F(4) | −1368(2) | −240(2) | 4289(2) | 43(1) |
| F(5) | −77(2) | 1427(2) | 4394(2) | 38(1) |
| F(6) | 3588(2) | 3993(2) | 720(1) | 38(1) |
| F(7) | 4470(3) | 4116(2) | −978(2) | 51(1) |
| F(8) | 4619(3) | 2418(2) | −1776(2) | 58(1) |
| F(9) | 3865(4) | 552(2) | −818(2) | 71(1) |
| F(10) | 3005(3) | 383(2) | 882(2) | 63(1) |
| N(1) | 5777(3) | 2602(2) | 1391(2) | 25(1) |
| N(2) | 6296(3) | 1729(2) | 3407(2) | 28(1) |
| N(3) | 5148(3) | 3070(2) | 3885(2) | 26(1) |
| O(1) | 2603(3) | 1690(2) | 3495(2) | 33(1) |

TABLE 12-continued

Atomic coordinates (×10⁴) and equivalent isotropic displacement parameters ($Å^2 \times 10^3$) for 5. U(eq) is defined as one third of the trace of the orthogonalized Uij tensor.

| | x | y | z | U(eq) |
|---|---|---|---|---|
| O(2) | 2927(3) | 2063(2) | 1720(2) | 31(1) |
| C(1) | 2599(4) | 126(3) | 2895(2) | 31(1) |
| C(2) | 1917(4) | −721(3) | 2838(3) | 34(1) |
| C(3) | 588(4) | −847(3) | 3294(3) | 34(1) |
| C(4) | −60(4) | −120(3) | 3816(3) | 32(1) |
| C(5) | 611(4) | 726(3) | 3870(2) | 28(1) |
| C(6) | 1961(4) | 892(3) | 3412(2) | 26(1) |
| C(7) | 3670(4) | 3110(3) | 363(2) | 26(1) |
| C(8) | 4120(4) | 3197(3) | −510(3) | 32(1) |
| C(9) | 4195(5) | 2333(3) | −919(3) | 38(1) |
| C(10) | 3808(5) | 1403(3) | −429(3) | 42(1) |
| C(11) | 3371(5) | 1321(3) | 439(3) | 38(1) |
| C(12) | 3303(4) | 2168(3) | 891(2) | 26(1) |
| C(13) | 3687(4) | 3763(3) | 2468(3) | 24(1) |
| C(14) | 1119(4) | 3776(3) | 2944(2) | 31(1) |
| C(15) | −106(4) | 4341(3) | 3094(3) | 39(1) |
| C(16) | −136(4) | 5417(3) | 2915(3) | 39(1) |
| C(17) | 1052(4) | 5930(3) | 2575(3) | 33(1) |
| C(18) | 2287(4) | 5373(3) | 2424(2) | 29(1) |
| C(19) | 2338(4) | 4293(3) | 2609(2) | 23(1) |
| C(20) | 6342(4) | 3501(3) | 983(3) | 32(1) |
| C(21) | 7259(4) | 3595(3) | 197(3) | 40(1) |
| C(22) | 7668(4) | 2731(3) | −216(3) | 43(1) |
| C(23) | 7147(4) | 1783(3) | 200(3) | 39(1) |
| C(24) | 6211(4) | 1750(3) | 990(3) | 33(1) |
| C(25) | 5258(4) | 2410(3) | 3286(2) | 23(1) |
| C(26) | 6780(4) | 1952(3) | 4046(3) | 38(1) |
| C(27) | 6066(4) | 2794(3) | 4339(3) | 35(1) |
| C(28) | 2966(4) | 3875(3) | 4616(2) | 27(1) |
| C(29) | 2148(4) | 4783(3) | 4761(2) | 32(1) |
| C(30) | 2580(4) | 5758(3) | 4358(3) | 33(1) |
| C(31) | 3892(4) | 5833(3) | 3818(3) | 32(1) |
| C(32) | 4764(4) | 4956(3) | 3649(3) | 29(1) |
| C(33) | 4241(4) | 3985(3) | 4042(2) | 25(1) |
| C(34) | 2460(4) | 2842(3) | 5089(3) | 39(1) |
| C(35) | 1645(5) | 6720(3) | 4486(3) | 48(1) |
| C(36) | 6180(4) | 5070(3) | 3083(3) | 44(1) |
| C(37) | 8121(4) | 1078(3) | 2258(3) | 39(1) |
| C(38) | 8739(5) | 252(4) | 1816(3) | 51(1) |
| C(39) | 8186(5) | −711(4) | 2003(3) | 51(1) |
| C(40) | 7005(5) | −869(3) | 2653(3) | 45(1) |
| C(41) | 6337(4) | −83(3) | 3137(3) | 35(1) |
| C(42) | 6922(4) | 899(3) | 2905(3) | 30(1) |
| C(43) | 8782(5) | 2110(4) | 2043(3) | 55(1) |
| C(44) | 8891(6) | −1601(4) | 1498(4) | 80(2) |
| C(45) | 5145(5) | −310(3) | 3892(3) | 47(1) |
| C(47) | 648(5) | 4042(4) | 7(4) | 59(1) |
| C(48) | 145(6) | 4468(5) | 752(3) | 62(2) |
| C(49) | −520(5) | 5435(5) | 739(3) | 60(1) |

TABLE 13

| Bond lengths [Å] and angles [°] for 5. | | | |
|---|---|---|---|
| Ru—C(13) | 1.843(3) | Ru—C(25) | 2.040(4) |
| Ru—O(1) | 2.076(3) | Ru—N(1) | 2.085(3) |
| Ru—O(2) | 2.110(3) | F(1)-C(1) | 1.350(4) |
| F(2)-C(2) | 1.358(4) | F(3)-C(3) | 1.354(4) |
| F(4)-C(4) | 1.355(4) | F(5)-C(5) | 1.361(4) |
| F(6)-C(7) | 1.354(4) | F(7)-C(8) | 1.338(4) |
| F(8)-C(9) | 1.349(4) | F(9)-C(10) | 1.352(4) |
| F(10)-C(11) | 1.350(4) | N(1)-C(20) | 1.346(5) |
| N(1)-C(24) | 1.352(5) | N(2)-C(25) | 1.376(4) |
| N(2)-C(26) | 1.379(5) | N(2)-C(42) | 1.451(4) |
| N(3)-C(27) | 1.375(5) | N(3)-C(25) | 1.383(4) |
| N(3)-C(33) | 1.456(4) | O(1)-C(6) | 1.323(4) |
| O(2)-C(12) | 1.305(4) | C(1)-C(2) | 1.387(5) |
| C(1)-C(6) | 1.404(5) | C(2)-C(3) | 1.366(6) |
| C(3)-C(4) | 1.372(5) | C(4)-C(5) | 1.377(5) |
| C(5)-C(6) | 1.393(5) | C(7)-C(8) | 1.377(5) |
| C(7)-C(12) | 1.406(5) | C(8)-C(9) | 1.384(5) |
| C(9)-C(10) | 1.372(6) | C(10)-C(11) | 1.367(6) |
| C(11)-C(12) | 1.408(5) | C(13)-C(19) | 1.472(5) |
| C(14)-C(15) | 1.384(5) | C(14)-C(19) | 1.401(5) |
| C(15)-C(16) | 1.386(6) | C(16)-C(17) | 1.373(6) |
| C(17)-C(18) | 1.387(5) | C(18)-C(19) | 1.393(5) |
| C(20)-C(21) | 1.362(5) | C(21)-C(22) | 1.374(5) |
| C(22)-C(23) | 1.387(6) | C(23)-C(24) | 1.376(5) |
| C(26)-C(27) | 1.337(5) | C(28)-C(33) | 1.380(5) |
| C(28)-C(29) | 1.401(5) | C(28)-C(34) | 1.502(5) |
| C(29)-C(30) | 1.386(6) | C(30)-C(31) | 1.386(6) |
| C(30)-C(35) | 1.515(5) | C(31)-C(32) | 1.401(5) |
| C(32)-C(33) | 1.405(6) | C(32)-C(36) | 1.491(6) |
| C(37)-C(42) | 1.387(6) | C(37)-C(38) | 1.393(5) |
| C(37)-C(43) | 1.504(6) | C(38)-C(39) | 1.375(7) |
| C(39)-C(40) | 1.375(7) | C(39)-C(44) | 1.534(5) |
| C(40)-C(41) | 1.400(5) | C(41)-C(42) | 1.412(5) |
| C(41)-C(45) | 1.486(6) | C(47)-C(48) | 1.371(7) |

TABLE 13-continued

Bond lengths [Å] and angles [°] for 5.

| | | | |
|---|---|---|---|
| C(47)-C(49)#1 | 1.362(7) | C(48)-C(49) | 1.382(8) |
| C(49)-C(47)#1 | 1.362(7) | | |
| C(13)-Ru—C(25) | 91.22(14) | C(13)-Ru—O(1) | 103.12(13) |
| C(25)-Ru—O(1) | 88.91(13) | C(13)-Ru—N(1) | 92.58(13) |
| C(25)-Ru—N(1) | 93.78(13) | O(1)-Ru—N(1) | 164.02(10) |
| C(13)-Ru—O(2) | 96.72(13) | C(25)-Ru—O(2) | 171.18(12) |
| O(1)-Ru—O(2) | 85.57(10) | N(1)-Ru—O(2) | 89.70(11) |
| C(20)-N(1)-C(24) | 116.2(3) | C(20)-N(1)-Ru | 129.0(2) |
| C(24)-N(1)-Ru | 114.2(3) | C(25)-N(2)-C(26) | 112.5(3) |
| C(25)-N(2)-C(42) | 126.4(3) | C(26)-N(2)-C(42) | 121.1(3) |
| C(27)-N(3)-C(25) | 111.9(3) | C(27)-N(3)-C(33) | 120.4(3) |
| C(25)-N(3)-C(33) | 127.6(3) | C(6)-O(1)-Ru | 120.4(2) |
| C(12)-O(2)-Ru | 125.4(2) | F(1)-C(1)-C(2) | 119.3(3) |
| F(1)-C(1)-C(6) | 118.9(3) | C(2)-C(1)-C(6) | 121.9(4) |
| F(2)-C(2)-C(3) | 119.4(3) | F(2)-C(2)-C(1) | 119.7(4) |
| C(3)-C(2)-C(1) | 120.9(3) | F(3)-C(3)-C(2) | 120.5(3) |
| F(3)-C(3)-C(4) | 120.8(4) | C(2)-C(3)-C(4) | 118.7(4) |
| F(4)-C(4)-C(3) | 119.8(3) | F(4)-C(4)-C(5) | 119.6(3) |
| C(3)-C(4)-C(5) | 120.6(4) | F(5)-C(5)-C(4) | 118.4(3) |
| F(5)-C(5)-C(6) | 118.8(3) | C(4)-C(5)-C(6) | 122.8(3) |
| O(1)-C(6)-C(5) | 121.9(3) | O(1)-C(6)-C(1) | 122.9(4) |
| C(5)-C(6)-C(1) | 115.1(3) | F(6)-C(7)-C(8) | 116.9(3) |
| F(6)-C(7)-C(12) | 119.3(3) | C(8)-C(7)-C(12) | 123.7(3) |
| F(7)-C(8)-C(7) | 121.0(3) | F(7)-C(8)-C(9) | 118.9(4) |
| C(7)-C(8)-C(9) | 120.1(4) | F(8)-C(9)-C(10) | 121.8(4) |
| F(8)-C(9)-C(8) | 120.3(4) | C(10)-C(9)-C(8) | 118.0(4) |
| F(9)-C(10)-C(9) | 118.7(4) | F(9)-C(10)-C(11) | 119.7(4) |
| C(9)-C(10)-C(11) | 121.6(4) | F(10)-C(11)-C(10) | 118.4(3) |
| F(10)-C(11)-C(12) | 118.5(4) | C(10)-C(11)-C(12) | 123.1(4) |
| O(2)-C(12)-C(7) | 124.6(3) | O(2)-C(12)-C(11) | 121.9(3) |
| C(7)-C(12)-C(11) | 113.5(3) | C(19)-C(13)-Ru | 128.4(3) |
| C(15)-C(14)-C(19) | 119.9(4) | C(14)-C(15)-C(16) | 120.4(4) |
| C(17)-C(16)-C(15) | 120.2(4) | C(16)-C(17)-C(18) | 120.0(4) |
| C(17)-C(18)-C(19) | 120.7(4) | C(18)-C(19)-C(14) | 118.8(3) |
| C(18)-C(19)-C(13) | 117.4(3) | C(14)-C(19)-C(13) | 123.7(3) |
| N(1)-C(20)-C(21) | 123.8(3) | C(20)-C(21)-C(22) | 119.5(4) |
| C(21)-C(22)-C(23) | 118.1(4) | C(24)-C(23)-C(22) | 119.1(4) |
| N(1)-C(24)-C(23) | 123.1(4) | N(2)-C(25)-N(3) | 101.7(3) |
| N(2)-C(25)-Ru | 127.6(2) | N(3)-C(25)-Ru | 130.5(2) |
| C(27)-C(26)-N(2) | 106.6(3) | C(26)-C(27)-N(3) | 107.3(3) |
| C(33)-C(28)-C(29) | 117.1(4) | C(33)-C(28)-C(34) | 122.7(3) |
| C(29)-C(28)-C(34) | 120.2(4) | C(30)-C(29)-C(28) | 122.4(4) |
| C(31)-C(30)-C(29) | 118.3(3) | C(31)-C(30)-C(35) | 120.4(4) |
| C(29)-C(30)-C(35) | 121.3(4) | C(30)-C(31)-C(32) | 122.0(4) |
| C(31)-C(32)-C(33) | 116.9(4) | C(31)-C(32)-C(36) | 120.5(4) |
| C(33)-C(32)-C(36) | 122.6(3) | C(28)-C(33)-C(32) | 123.1(3) |
| C(28)-C(33)-N(3) | 119.4(3) | C(32)-C(33)-N(3) | 117.3(3) |
| C(42)-C(37)-C(38) | 117.8(4) | C(42)-C(37)-C(43) | 122.4(4) |
| C(38)-C(37)-C(43) | 119.8(4) | C(39)-C(38)-C(37) | 121.8(5) |
| C(40)-C(39)-C(38) | 119.2(4) | C(40)-C(39)-C(44) | 120.5(5) |
| C(38)-C(39)-C(44) | 120.3(5) | C(39)-C(40)-C(41) | 122.4(4) |
| C(40)-C(41)-C(42) | 116.3(4) | C(40)-C(41)-C(45) | 120.9(4) |
| C(42)-C(41)-C(45) | 122.6(3) | C(37)-C(42)-C(41) | 122.5(3) |
| C(37)-C(42)-N(2) | 118.9(3) | C(41)-C(42)-N(2) | 118.4(4) |
| C(48)-C(47)-C(49)#1 | 121.0(5) | C(47)-C(48)-C(49) | 119.0(5) |
| C(47)#1-C(49)-C(48) | 120.0(5) | | |

Symmetry transformations used to generate equivalent atoms:
1 −x, −y + 1, −z

TABLE 14

Anisotropic displacement parameters ($Å^2 \times 10^3$) for 5.
The anisotropic displacement factor exponent takes the form:
$-2 \pi^2 [h^2 a^{*} U11 + \ldots + 2 h k a^{*} b^{*} U12]$

| | U1 | U22 | U33 | U23 | U13 | U12 |
|---|---|---|---|---|---|---|
| Ru | 23(1) | 19(1) | 24(1) | −7(1) | −5(1) | 1(1) |
| F(1) | 31(1) | 47(1) | 37(1) | −6(1) | −1(1) | −1(1) |
| F(2) | 56(2) | 32(1) | 59(2) | −22(1) | −5(1) | 3(1) |
| F(3) | 51(2) | 29(1) | 64(2) | −7(1) | −20(1) | −9(1) |
| F(4) | 27(1) | 40(1) | 56(2) | 0(1) | −5(1) | −3(1) |
| F(5) | 34(1) | 35(1) | 41(1) | −12(1) | −1(1) | 4(1) |

TABLE 14-continued

Anisotropic displacement parameters ($Å^2 \times 10^3$) for 5.
The anisotropic displacement factor exponent takes the form:
$-2 \pi^2 [h^2 a^{*} U11 + \ldots + 2 h k a^{*} b^{*} U12]$

| | U1 | U22 | U33 | U23 | U13 | U12 |
|---|---|---|---|---|---|---|
| F(6) | 53(2) | 24(1) | 40(2) | −11(1) | −16(1) | 3(1) |
| F(7) | 72(2) | 32(1) | 39(2) | 5(1) | −4(1) | −6(1) |
| F(8) | 86(2) | 54(2) | 28(2) | −8(1) | −6(1) | 3(2) |
| F(9) | 142(3) | 34(1) | 44(2) | −16(1) | −31(2) | −9(2) |
| F(10) | 121(3) | 33(1) | 42(2) | −1(1) | −30(2) | −27(2) |
| N(1) | 25(2) | 22(2) | 28(2) | −7(1) | −7(1) | 1(1) |

TABLE 14-continued

Anisotropic displacement parameters ($A^2 \times 10^3$) for 5.
The anisotropic displacement factor exponent takes the form:
$-2 \pi^2 [h^2 a^{*} U11 + \ldots + 2 h k a^{*} b^{*} U12]$

| | U1 | U22 | U33 | U23 | U13 | U12 |
|---|---|---|---|---|---|---|
| N(2) | 31(2) | 25(2) | 31(2) | −10(1) | −14(2) | 10(1) |
| N(3) | 24(2) | 26(2) | 28(2) | −12(1) | −8(1) | 8(1) |
| O(1) | 36(2) | 35(1) | 28(2) | −6(1) | −6(1) | −12(1) |
| O(2) | 32(2) | 36(2) | 26(2) | −5(1) | −8(1) | −9(1) |
| C(1) | 31(2) | 31(2) | 29(2) | −3(2) | −7(2) | −2(2) |
| C(2) | 40(3) | 27(2) | 34(2) | −9(2) | −8(2) | 3(2) |
| C(3) | 41(3) | 22(2) | 42(3) | 1(2) | −16(2) | −7(2) |
| C(4) | 26(2) | 29(2) | 39(2) | 4(2) | −10(2) | −1(2) |
| C(5) | 30(2) | 24(2) | 28(2) | −6(2) | −6(2) | 5(2) |
| C(6) | 32(2) | 27(2) | 20(2) | 0(2) | −9(2) | −2(2) |
| C(7) | 27(2) | 24(2) | 32(2) | −8(2) | −11(2) | 1(2) |
| C(8) | 33(2) | 27(2) | 32(2) | 1(2) | −8(2) | 0(2) |
| C(9) | 50(3) | 39(2) | 22(2) | −6(2) | −8(2) | 2(2) |
| C(10) | 64(3) | 30(2) | 37(3) | −14(2) | −18(2) | 1(2) |
| C(11) | 60(3) | 25(2) | 30(2) | 0(2) | −17(2) | −11(2) |
| C(12) | 24(2) | 29(2) | 25(2) | −5(2) | −7(2) | −3(2) |
| C(13) | 23(2) | 25(2) | 24(2) | −10(2) | −4(2) | −4(1) |
| C(14) | 31(2) | 29(2) | 35(2) | −8(2) | −10(2) | −2(2) |
| C(15) | 23(2) | 49(3) | 44(3) | −9(2) | −6(2) | −2(2) |
| C(16) | 33(3) | 47(2) | 38(3) | −15(2) | −12(2) | 16(2) |
| C(17) | 36(3) | 28(2) | 38(3) | −10(2) | −14(2) | 7(2) |
| C(18) | 30(2) | 29(2) | 28(2) | −7(2) | −7(2) | 1(2) |
| C(19) | 26(2) | 26(2) | 20(2) | −10(2) | −7(2) | 7(2) |
| C(20) | 24(2) | 28(2) | 39(2) | −10(2) | 0(2) | −2(2) |
| C(21) | 32(2) | 29(2) | 48(3) | 3(2) | 2(2) | −3(2) |
| C(22) | 38(3) | 44(2) | 37(3) | −9(2) | 4(2) | 2(2) |
| C(23) | 39(3) | 37(2) | 32(2) | −14(2) | 2(2) | 8(2) |
| C(24) | 35(2) | 23(2) | 36(2) | −8(2) | −3(2) | 0(2) |
| C(25) | 21(2) | 23(2) | 23(2) | −6(2) | −4(2) | 4(1) |
| C(26) | 38(3) | 41(2) | 43(3) | −17(2) | −24(2) | 13(2) |
| C(27) | 37(2) | 38(2) | 41(3) | −18(2) | −23(2) | 12(2) |
| C(28) | 28(2) | 32(2) | 26(2) | −13(2) | −12(2) | 3(2) |
| C(29) | 23(2) | 43(2) | 29(2) | −18(2) | −6(2) | 7(2) |
| C(30) | 36(2) | 33(2) | 36(2) | −19(2) | −18(2) | 12(2) |
| C(31) | 36(2) | 24(2) | 40(3) | −8(2) | −18(2) | 2(2) |
| C(32) | 26(2) | 27(2) | 39(2) | −13(2) | −14(2) | 1(2) |
| C(33) | 21(2) | 26(2) | 33(2) | −14(2) | −11(2) | 6(2) |
| C(34) | 40(3) | 38(2) | 37(3) | −9(2) | −5(2) | −4(2) |
| C(35) | 48(3) | 49(3) | 57(3) | −28(2) | −29(3) | 30(2) |
| C(36) | 30(3) | 36(2) | 62(3) | −13(2) | −7(2) | −5(2) |
| C(37) | 29(2) | 45(2) | 41(3) | −11(2) | −10(2) | 12(2) |
| C(38) | 38(3) | 66(3) | 47(3) | −21(2) | −12(2) | 27(2) |
| C(39) | 57(3) | 54(3) | 47(3) | −29(2) | −22(3) | 31(2) |
| C(40) | 69(3) | 27(2) | 49(3) | −18(2) | −29(3) | 15(2) |
| C(41) | 45(3) | 28(2) | 38(3) | −9(2) | −23(2) | 11(2) |
| C(42) | 35(2) | 26(2) | 32(2) | −10(2) | −16(2) | 13(2) |
| C(43) | 38(3) | 63(3) | 62(4) | −9(3) | −11(3) | 1(2) |
| C(44) | 91(5) | 77(4) | 82(4) | −57(3) | −32(4) | 49(3) |
| C(45) | 59(3) | 37(2) | 43(3) | −3(2) | −14(3) | 1(2) |
| C(47) | 38(3) | 54(3) | 92(5) | −6(3) | −29(3) | −7(2) |
| C(48) | 59(4) | 85(4) | 48(3) | 19(3) | −30(3) | −32(3) |
| C(49) | 46(3) | 86(4) | 49(3) | −22(3) | −4(3) | −17(3) |

TABLE 15

Hydrogen coordinates ($\times 10^4$) and isotropic displacement parameters ($A^2 \times 10^3$) for 5.

| | x | y | z | U(eq) |
|---|---|---|---|---|
| H(13A) | 4419 | 4197 | 2359 | 28 |
| H(14A) | 1133 | 3047 | 3066 | 37 |
| H(15A) | −923 | 3993 | 3318 | 47 |
| H(16A) | −972 | 5796 | 3027 | 47 |
| H(17A) | 1029 | 6659 | 2444 | 40 |
| H(18A) | 3098 | 5729 | 2195 | 35 |
| H(20A) | 6088 | 4100 | 1258 | 38 |
| H(21A) | 7610 | 4246 | −62 | 48 |
| H(22A) | 8284 | 2780 | −765 | 51 |
| H(23A) | 7429 | 1171 | −55 | 46 |
| H(24A) | 5856 | 1106 | 1264 | 39 |
| H(26A) | 7475 | 1584 | 4238 | 45 |
| H(27A) | 6172 | 3135 | 4774 | 42 |
| H(29A) | 1273 | 4730 | 5146 | 38 |
| H(31A) | 4206 | 6493 | 3556 | 38 |
| H(34A) | 3151 | 2300 | 4916 | 58 |
| H(34B) | 1643 | 2698 | 4962 | 58 |
| H(34C) | 2260 | 2861 | 5695 | 58 |
| H(35A) | 775 | 6528 | 4883 | 72 |
| H(35B) | 1518 | 7029 | 3946 | 72 |
| H(35C) | 2044 | 7218 | 4711 | 72 |
| H(36A) | 6336 | 5801 | 2881 | 65 |
| H(36B) | 6312 | 4691 | 2603 | 65 |
| H(36C) | 6812 | 4794 | 3398 | 65 |
| H(38A) | 9555 | 356 | 1377 | 61 |
| H(40A) | 6631 | −1529 | 2778 | 54 |
| H(43A) | 9606 | 2073 | 1575 | 83 |
| H(43B) | 9004 | 2276 | 2535 | 83 |
| H(43C) | 8164 | 2647 | 1881 | 83 |
| H(44A) | 8368 | −2220 | 1712 | 120 |
| H(44B) | 9794 | −1743 | 1562 | 120 |
| H(44C) | 8957 | −1403 | 902 | 120 |
| H(45A) | 4906 | −1026 | 3937 | 71 |
| H(45B) | 4383 | 152 | 3831 | 71 |
| H(45C) | 5366 | −204 | 4399 | 71 |
| H(47A) | 1088 | 3380 | 12 | 71 |
| H(48A) | 251 | 4108 | 1263 | 74 |
| H(49A) | −883 | 5733 | 1245 | 73 |

TABLE 16

Torsion angles [deg] for 5.

| | | | |
|---|---|---|---|
| C(13)-Ru—N(1)-C(20) | 9.7(3) | C(25)-Ru—N(1)-C(20) | −81.7(3) |
| O(1)-Ru—N(1)-C(20) | 179.0(4) | O(2)-Ru—N(1)-C(20) | 106.4(3) |
| C(13)-Ru—N(1)-C(24) | −161.0(3) | C(25)-Ru—N(1)-C(24) | 107.6(3) |
| O(1)-Ru—N(1)-C(24) | 8.3(3) | O(2)-Ru—N(1)-C(24) | −64.3(3) |
| C(13)-Ru—O(1)-C(6) | 132.5(3) | C(25)-Ru—O(1)-C(6) | −136.5(3) |

TABLE 16-continued

Torsion angles [deg] for 5.

| | | | |
|---|---|---|---|
| N(1)-Ru—O(1)-C(6) | −36.5(5) | O(2)-Ru—O(1)-C(6) | 36.6(3) |
| C(13)-Ru—O(2)-C(12) | 86.3(3) | C(25)-Ru—O(2)-C(12) | −119.6(8) |
| O(1)-Ru—O(2)-C(12) | −170.9(3) | N(1)-Ru—O(2)-C(12) | −6.2(3) |
| F(1)-C(1)-C(2)-F(2) | −1.8(6) | C(6)-C(1)-C(2)-F(2) | 178.9(3) |
| F(1)-C(1)-C(2)-C(3) | 178.7(4) | C(6)-C(1)-C(2)-C(3) | −0.5(6) |
| F(2)-C(2)-C(3)-F(3) | 0.6(6) | C(1)-C(2)-C(3)-F(3) | −179.9(4) |
| F(2)-C(2)-C(3)-C(4) | 180.0(4) | C(1)-C(2)-C(3)-C(4) | −0.5(6) |
| F(3)-C(3)-C(4)-F(4) | 0.9(6) | C(2)-C(3)-C(4)-F(4) | −178.5(4) |
| F(3)-C(3)-C(4)-C(5) | −179.7(3) | C(2)-C(3)-C(4)-C(5) | 0.9(6) |
| F(4)-C(4)-C(5)-F(5) | −0.9(5) | C(3)-C(4)-C(5)-F(5) | 179.7(3) |
| F(4)-C(4)-C(5)-C(6) | 179.1(3) | C(3)-C(4)-C(5)-C(6) | −0.4(6) |
| Ru—O(1)-C(6)-C(5) | −149.2(3) | Ru—O(1)-C(6)-C(1) | 34.2(5) |
| F(5)-C(5)-C(6)-O(1) | 2.4(5) | C(4)-C(5)-C(6)-O(1) | −177.5(4) |
| F(5)-C(5)-C(6)-C(1) | 179.3(3) | C(4)-C(5)-C(6)-C(1) | −0.7(6) |
| F(1)-C(1)-C(6)-O(1) | −1.3(6) | C(2)-C(1)-C(6)-O(1) | 177.9(4) |
| F(1)-C(1)-C(6)-C(5) | −178.1(3) | C(2)-C(1)-C(6)-C(5) | 1.1(6) |
| F(6)-C(7)-C(8)-F(7) | 0.6(5) | C(12)-C(7)-C(8)-F(7) | −179.2(3) |
| F(6)-C(7)-C(8)-C(9) | −178.3(4) | C(12)-C(7)-C(8)-C(9) | 1.9(6) |
| F(7)-C(8)-C(9)-F(8) | 0.3(6) | C(7)-C(8)-C(9)-F(8) | 179.2(4) |
| F(7)-C(8)-C(9)-C(10) | −178.8(4) | C(7)-C(8)-C(9)-C(10) | 0.1(6) |
| F(8)-C(9)-C(10)-F(9) | 0.4(7) | C(8)-C(9)-C(10)-F(9) | 179.5(4) |
| F(8)-C(9)-C(10)-C(11) | −179.6(4) | C(8)-C(9)-C(10)-C(11) | −0.5(7) |
| F(9)-C(10)-C(11)-F(10) | −0.1(7) | C(9)-C(10)-C(11)-F(10) | 179.9(4) |
| F(9)-C(10)-C(11)-C(12) | 179.0(4) | C(9)-C(10)-C(11)-C(12) | −0.9(7) |
| Ru—O(2)-C(12)-C(7) | −61.5(5) | Ru—O(2)-C(12)-C(11) | 118.8(4) |
| F(6)-C(7)-C(12)-O(2) | −2.7(6) | C(8)-C(7)-C(12)-O(2) | 177.1(4) |
| F(6)-C(7)-C(12)-C(11) | 177.1(3) | C(8)-C(7)-C(12)-C(11) | −3.1(6) |
| F(10)-C(11)-C(12)-O(2) | 1.5(6) | C(10)-C(11)-C(12)-O(2) | −177.6(4) |
| F(10)-C(11)-C(12)-C(7) | −178.2(4) | C(10)-C(11)-C(12)-C(7) | 2.6(6) |
| C(25)-Ru—C(13)-C(19) | −129.9(3) | O(1)-Ru—C(13)-C(19) | −40.8(3) |
| N(1)-Ru—C(13)-C(19) | 136.2(3) | O(2)-Ru—C(13)-C(19) | 46.2(3) |
| C(19)-C(14)-C(15)-C(16) | 0.0(6) | C(14)-C(15)-C(16)-C(17) | 1.0(6) |
| C(15)-C(16)-C(17)-C(18) | −1.3(6) | C(16)-C(17)-C(18)-C(19) | 0.5(6) |
| C(17)-C(18)-C(19)-C(14) | 0.5(5) | C(17)-C(18)-C(19)-C(13) | −177.3(3) |
| C(15)-C(14)-C(19)-C(18) | −0.7(6) | C(15)-C(14)-C(19)-C(13) | 176.9(4) |
| Ru—C(13)-C(19)-C(18) | −169.1(3) | Ru—C(13)-C(19)-C(14) | 13.3(5) |
| C(24)-N(1)-C(20)-C(21) | 2.7(6) | Ru—N(1)-C(20)-C(21) | −167.8(3) |
| N(1)-C(20)-C(21)-C(22) | −1.1(7) | C(20)-C(21)-C(22)-C(23) | −1.5(7) |
| C(21)-C(22)-C(23)-C(24) | 2.3(7) | C(20)-N(1)-C(24)-C(23) | −1.8(6) |
| Ru—N(1)-C(24)-C(23) | 170.1(3) | C(22)-C(23)-C(24)-N(1) | −0.7(7) |
| C(26)-N(2)-C(25)-N(3) | 0.6(4) | C(42)-N(2)-C(25)-N(3) | −175.4(4) |
| C(26)-N(2)-C(25)-Ru | −175.7(3) | C(42)-N(2)-C(25)-Ru | 8.3(6) |
| C(27)-N(3)-C(25)-N(2) | −0.2(4) | C(33)-N(3)-C(25)-N(2) | 177.6(3) |
| C(27)-N(3)-C(25)-Ru | 176.0(3) | C(33)-N(3)-C(25)-Ru | −6.2(6) |
| C(13)-Ru—C(25)-N(2) | −157.3(3) | O(1)-Ru—C(25)-N(2) | 99.6(3) |
| N(1)-Ru—C(25)-N(2) | −64.7(3) | O(2)-Ru—C(25)-N(2) | 48.4(10) |
| C(13)-Ru—C(25)-N(3) | 27.3(4) | O(1)-Ru—C(25)-N(3) | −75.8(3) |
| N(1)-Ru—C(25)-N(3) | 120.0(3) | O(2)-Ru—C(25)-N(3) | −126.9(7) |
| C(25)-N(2)-C(26)-C(27) | −0.8(5) | C(42)-N(2)-C(26)-C(27) | 175.4(4) |
| N(2)-C(26)-C(27)-N(3) | 0.7(5) | C(25)-N(3)-C(27)-C(26) | −0.3(5) |
| C(33)-N(3)-C(27)-C(26) | −178.3(4) | C(33)-C(28)-C(29)-C(30) | −0.4(5) |
| C(34)-C(28)-C(29)-C(30) | 178.3(4) | C(28)-C(29)-C(30)-C(31) | −2.5(6) |
| C(29)-C(30)-C(31)-C(35) | 176.3(4) | C(29)-C(30)-C(31)-C(32) | 2.1(6) |
| C(35)-C(30)-C(31)-C(32) | −176.7(4) | C(30)-C(31)-C(32)-C(33) | 1.2(6) |
| C(30)-C(31)-C(32)-C(36) | −178.3(4) | C(29)-C(28)-C(33)-C(32) | 4.0(5) |
| C(34)-C(28)-C(33)-C(32) | −174.7(4) | C(29)-C(28)-C(33)-N(3) | 178.3(3) |
| C(34)-C(28)-C(33)-N(3) | −0.4(5) | C(31)-C(32)-C(33)-C(28) | −4.4(5) |
| C(36)-C(32)-C(33)-C(28) | 175.1(4) | C(31)-C(32)-C(33)-N(3) | −178.8(3) |
| C(36)-C(32)-C(33)-N(3) | 0.7(5) | C(27)-N(3)-C(33)-C(28) | −92.9(4) |
| C(25)-N(3)-C(33)-C(28) | 89.5(5) | C(27)-N(3)-C(33)-C(32) | 81.7(5) |
| C(25)-N(3)-C(33)-C(32) | −95.9(4) | C(42)-C(37)-C(38)-C(39) | 0.4(7) |
| C(43)-C(37)-C(38)-C(39) | 178.6(4) | C(37)-C(38)-C(39)-C(40) | −1.1(7) |
| C(37)-C(38)-C(39)-C(44) | 179.7(4) | C(38)-C(39)-C(40)-C(41) | −0.1(7) |
| C(44)-C(39)-C(40)-C(41) | 179.2(4) | C(39)-C(40)-C(41)-C(42) | 1.8(6) |
| C(39)-C(40)-C(41)-C(45) | −173.5(4) | C(38)-C(37)-C(42)-C(41) | 1.5(6) |
| C(43)-C(37)-C(42)-C(41) | −176.6(4) | C(38)-C(37)-C(42)-N(2) | 176.7(4) |
| C(43)-C(37)-C(42)-N(2) | −1.5(6) | C(40)-C(41)-C(42)-C(37) | −2.6(6) |
| C(45)-C(41)-C(42)-C(37) | 172.7(4) | C(40)-C(41)-C(42)-N(2) | −177.7(3) |
| C(45)-C(41)-C(42)-N(2) | −2.5(6) | C(25)-N(2)-C(42)-C(37) | 97.1(5) |
| C(26)-N(2)-C(42)-C(37) | −78.5(5) | C(25)-N(2)-C(42)-C(41) | −87.5(5) |
| C(26)-N(2)-C(42)-C(41) | 96.8(5) | C(49)#1-C(47)-C(48)-C(49) | 1.1(9) |
| C(47)-C(48)-C(49)-C(47)#1 | −1.1(9) | | |

Symmetry transformations used to generate equivalent atoms:
1 −x, −y + 1, −z

TABLE 17

Crystal data and structure refinement for df302.

| | |
|---|---|
| Identification code | df302 |
| Empirical formula | C56.57 H46.14 F8 N3 O2.89 Ru |
| Formula weight | 1067.28 |
| Temperature | 207(2) K |
| Wavelength | 0.71073 Å |
| Crystal system | Monoclinic |
| Space group | C2/c |
| Unit cell dimensions | a = 41.971(8) Å  α = 90°. |
| | b = 11.122(2) Å  β = 128.65(3)°. |
| | c = 27.440(6) Å  γ = 90°. |
| Volume | 10004(3) Å$^3$ |
| Z | 8 |
| Density (calculated) | 1.417 Mg/m$^3$ |
| Absorption coefficient | 0.391 mm$^{-1}$ |
| F(000) | 4366 |
| Crystal size | 0.55 × 0.45 × 0.20 mm$^3$ |
| Theta range for data collection | 1.49 to 24.82°. |
| Index ranges | −49 <= h <= 34, −13 <= k <= 13, −32 <= l <= 32 |
| Reflections collected | 27646 |
| Independent reflections | 8458 [R(int) = 0.0554] |
| Completeness to theta = 24.82° | 97.8% |
| Absorption correction | Empirical, Multiscan |
| Max. and min. transmission | 1.0 and 0.5 |
| Refinement method | Full-matrix least-squares on F$^2$ |
| Data/restraints/parameters | 8458/2/656 |
| Goodness-of-fit on F$^2$ | 1.125 |
| Final R indices [I > 2sigma(I)] | R1 = 0.0618, wR2 = 0.1535 |
| R indices (all data) | R1 = 0.0893, wR2 = 0.1640 |
| Largest diff. peak and hole | 0.803 and −0.374 e.Å$^{-3}$ |

TABLE 18

Atomic coordinates (×10$^4$) and equivalent isotropic displacement parameters (Å$^2$ × 10$^3$) for df302. U(eq) is defined as one third of the trace of the orthogonalized U$^{ij}$ tensor.

| | x | y | z | U(eq) |
|---|---|---|---|---|
| Ru(1) | 3855(1) | 1784(1) | 3207(1) | 30(1) |
| C(2) | 3359(2) | 1023(6) | 2764(3) | 37(1) |
| C(3) | 3239(2) | −187(6) | 2498(3) | 36(1) |
| C(4) | 3507(2) | −1161(6) | 2747(3) | 48(2) |
| C(5) | 3370(2) | −2283(7) | 2464(4) | 62(2) |
| C(6) | 2980(2) | −2449(7) | 1943(4) | 60(2) |
| C(7) | 2709(2) | −1511(6) | 1694(3) | 53(2) |
| C(8) | 2837(2) | −392(6) | 1980(3) | 43(2) |
| C(9) | 3643(2) | 3152(5) | 2584(2) | 32(1) |
| N(10) | 3273(1) | 3585(4) | 2068(2) | 31(1) |
| C(11) | 3328(2) | 4595(6) | 1829(3) | 41(2) |
| C(12) | 3731(2) | 4824(6) | 2189(3) | 41(2) |
| N(13) | 3917(1) | 3945(4) | 2645(2) | 34(1) |
| C(14) | 4349(2) | 3861(5) | 3146(3) | 35(1) |
| C(15) | 4505(2) | 4273(6) | 3747(3) | 38(1) |
| C(16) | 4922(2) | 4176(6) | 4221(3) | 47(2) |
| C(17) | 5182(2) | 3738(7) | 4114(3) | 53(2) |
| C(18) | 5018(2) | 3394(6) | 3509(3) | 52(2) |
| C(19) | 4604(2) | 3443(6) | 3016(3) | 39(2) |
| C(20) | 4442(2) | 3109(7) | 2362(3) | 51(2) |
| C(21) | 5639(2) | 3657(9) | 4642(4) | 83(3) |
| C(22) | 4239(2) | 4838(6) | 3884(3) | 45(2) |
| C(23) | 2871(2) | 3197(6) | 1826(3) | 37(1) |
| C(24) | 2711(2) | 3645(6) | 2115(3) | 41(2) |
| C(25) | 2317(2) | 3296(7) | 1864(3) | 50(2) |
| C(26) | 2078(2) | 2566(7) | 1338(3) | 51(2) |
| C(27) | 2247(2) | 2194(7) | 1057(3) | 52(2) |
| C(28) | 2640(2) | 2488(6) | 1285(3) | 41(2) |
| C(29) | 2799(2) | 2090(7) | 948(3) | 54(2) |
| C(30) | 1655(2) | 2234(9) | 1080(4) | 79(3) |
| C(31) | 2950(2) | 4489(6) | 2663(3) | 46(2) |
| N(32) | 4071(2) | 842(4) | 2795(2) | 35(1) |
| C(33) | 3835(2) | 516(6) | 2189(3) | 40(2) |
| C(34) | 3969(2) | −152(7) | 1925(3) | 52(2) |
| C(35) | 4372(3) | −481(7) | 2290(4) | 59(2) |

TABLE 18-continued

Atomic coordinates (×10$^4$) and equivalent isotropic displacement parameters (Å$^2$ × 10$^3$) for df302. U(eq) is defined as one third of the trace of the orthogonalized U$^{ij}$ tensor.

| | x | y | z | U(eq) |
|---|---|---|---|---|
| C(36) | 4624(2) | −147(7) | 2908(3) | 56(2) |
| C(37) | 4466(2) | 503(6) | 3147(3) | 43(2) |
| O(38) | 4308(1) | 926(4) | 4017(2) | 39(1) |
| C(39) | 4518(2) | 1382(5) | 4588(3) | 33(1) |
| C(40) | 4954(2) | 1465(5) | 4944(3) | 38(2) |
| C(41) | 5198(2) | 1888(6) | 5538(3) | 41(2) |
| C(42) | 5033(2) | 2343(6) | 5818(3) | 40(2) |
| C(43) | 5277(2) | 2831(6) | 6430(3) | 43(2) |
| C(44) | 5121(2) | 3307(7) | 6693(3) | 54(2) |
| C(45) | 4694(2) | 3332(7) | 6343(3) | 55(2) |
| C(46) | 4452(2) | 2849(7) | 5762(3) | 49(2) |
| C(47) | 4600(2) | 2300(6) | 5474(3) | 38(1) |
| C(48) | 4348(2) | 1720(6) | 4872(3) | 35(1) |
| F(49) | 4043(1) | 2987(4) | 5444(2) | 73(1) |
| F(50) | 4541(2) | 3870(5) | 6600(3) | 92(1) |
| F(51) | 5360(1) | 3739(5) | 7286(5) | 78(1) |
| F(52) | 5688(1) | 2822(4) | 6769(2) | 62(1) |
| O(53) | 3706(1) | 2708(4) | 3705(2) | 37(1) |
| C(54) | 3610(2) | 2011(5) | 3992(3) | 34(1) |
| C(55) | 3910(2) | 1434(5) | 4555(3) | 33(1) |
| C(56) | 3799(2) | 620(5) | 4832(3) | 35(1) |
| C(57) | 4070(2) | −113(6) | 5368(3) | 40(2) |
| C(58) | 3944(2) | −837(6) | 5616(3) | 45(2) |
| C(59) | 3535(2) | −907(6) | 5362(3) | 51(2) |
| C(60) | 3259(2) | −242(6) | 4842(3) | 44(2) |
| C(61) | 3370(2) | 512(6) | 4555(3) | 38(2) |
| C(62) | 3080(2) | 1176(6) | 4009(3) | 48(2) |
| C(63) | 3193(2) | 1886(6) | 3736(3) | 43(2) |
| F(64) | 2860(1) | −285(4) | 4594(2) | 62(1) |
| F(65) | 3416(1) | −1646(4) | 5618(2) | 72(1) |
| F(66) | 4214(1) | −1522(4) | 6128(2) | 64(1) |
| F(67) | 4472(1) | −158(4) | 5635(2) | 52(1) |
| O(68) | 2888(3) | −3564(9) | 642(4) | 129(3) |
| C(69) | 3142(5) | −2556(13) | 772(9) | 157(7) |
| C(70) | 3391(6) | −2917(16) | 647(10) | 190(9) |
| C(71) | 3279(5) | −4034(18) | 337(10) | 186(9) |
| C(72) | 2917(5) | −4296(15) | 230(6) | 145(6) |

TABLE 19

Bond lengths [Å] and angles [°] for df302.

| | |
|---|---|
| Ru(1)-C(2) | 1.834(6) |
| Ru(1)-C(9) | 2.032(6) |
| Ru(1)-O(38) | 2.046(4) |
| Ru(1)-O(53) | 2.096(4) |
| Ru(1)-N(32) | 2.117(5) |
| C(2)-C(3) | 1.463(9) |
| C(3)-C(8) | 1.387(8) |
| C(3)-C(4) | 1.395(9) |
| C(4)-C(5) | 1.391(10) |
| C(5)-C(6) | 1.353(10) |
| C(6)-C(7) | 1.370(10) |
| C(7)-C(8) | 1.388(9) |
| C(9)-N(13) | 1.372(7) |
| C(9)-N(10) | 1.380(7) |
| N(10)-C(11) | 1.390(8) |
| N(10)-C(23) | 1.439(7) |
| C(11)-C(12) | 1.350(9) |
| C(12)-N(13) | 1.382(7) |
| N(13)-C(14) | 1.440(7) |
| C(14)-C(19) | 1.406(8) |
| C(14)-C(15) | 1.418(8) |
| C(15)-C(16) | 1.385(9) |
| C(15)-C(22) | 1.521(9) |
| C(16)-C(17) | 1.386(9) |
| C(17)-C(18) | 1.395(10) |
| C(17)-C(21) | 1.521(9) |
| C(18)-C(19) | 1.382(9) |
| C(19)-C(20) | 1.514(8) |

TABLE 19-continued

Bond lengths [Å] and angles [°] for df302.

| | |
|---|---|
| C(23)-C(28) | 1.401(8) |
| C(23)-C(24) | 1.415(8) |
| C(24)-C(25) | 1.392(9) |
| C(24)-C(31) | 1.505(9) |
| C(25)-C(26) | 1.393(10) |
| C(26)-C(27) | 1.396(10) |
| C(26)-C(30) | 1.493(9) |
| C(27)-C(28) | 1.389(9) |
| C(28)-C(29) | 1.506(9) |
| N(32)-C(33) | 1.348(7) |
| N(32)-C(37) | 1.349(8) |
| C(33)-C(34) | 1.379(9) |
| C(34)-C(35) | 1.374(10) |
| C(35)-C(36) | 1.375(10) |
| C(36)-C(37) | 1.391(9) |
| O(38)-C(39) | 1.327(7) |
| C(39)-C(48) | 1.395(8) |
| C(39)-C(40) | 1.443(8) |
| C(40)-C(41) | 1.356(9) |
| C(41)-C(42) | 1.412(9) |
| C(42)-C(43) | 1.419(9) |
| C(42)-C(47) | 1.431(8) |
| C(43)-C(44) | 1.352(10) |
| C(43)-F(52) | 1.355(7) |
| C(44)-F(51) | 1.358(7) |
| C(44)-C(45) | 1.406(10) |
| C(45)-F(50) | 1.356(8) |
| C(45)-C(46) | 1.357(9) |
| C(46)-F(49) | 1.367(7) |
| C(46)-C(47) | 1.412(9) |
| C(47)-C(48) | 1.444(8) |
| C(48)-C(55) | 1.499(8) |
| O(53)-C(54) | 1.333(7) |
| C(54)-C(55) | 1.398(8) |
| C(54)-C(63) | 1.430(8) |
| C(55)-C(56) | 1.433(8) |
| C(56)-C(57) | 1.425(8) |
| C(56)-C(61) | 1.456(8) |
| C(57)-F(67) | 1.356(7) |
| C(57)-C(58) | 1.357(9) |
| C(58)-F(66) | 1.359(7) |
| C(58)-C(59) | 1.397(10) |
| C(59)-F(65) | 1.361(7) |
| C(59)-C(60) | 1.363(10) |
| C(60)-F(64) | 1.358(7) |
| C(60)-C(61) | 1.415(9) |
| C(61)-C(62) | 1.413(9) |
| C(62)-C(63) | 1.362(9) |
| O(68)-C(69) | 1.429(12) |
| O(68)-C(72) | 1.457(12) |
| C(69)-C(70) | 1.347(14) |
| C(70)-C(71) | 1.411(19) |
| C(71)-C(72) | 1.387(14) |
| C(2)-Ru(1)-C(9) | 93.9(2) |
| C(2)-Ru(1)-O(38) | 113.8(2) |
| C(9)-Ru(1)-O(38) | 152.2(2) |
| C(2)-Ru(1)-O(53) | 88.9(2) |
| C(9)-Ru(1)-O(53) | 91.68(19) |
| O(38)-Ru(1)-O(53) | 88.42(15) |
| C(2)-Ru(1)-N(32) | 96.1(2) |
| C(9)-Ru(1)-N(32) | 91.7(2) |
| O(38)-Ru(1)-N(32) | 86.17(17) |
| O(53)-Ru(1)-N(32) | 173.81(17) |
| C(3)-C(2)-Ru(1) | 130.5(4) |
| C(8)-C(3)-C(4) | 117.9(6) |
| C(8)-C(3)-C(2) | 118.8(5) |
| C(4)-C(3)-C(2) | 123.3(6) |
| C(5)-C(4)-C(3) | 119.7(6) |
| C(6)-C(5)-C(4) | 121.3(7) |
| C(5)-C(6)-C(7) | 120.1(7) |
| C(6)-C(7)-C(8) | 119.5(7) |
| C(3)-C(8)-C(7) | 121.3(6) |
| N(13)-C(9)-N(10) | 102.8(5) |
| N(13)-C(9)-Ru(1) | 119.0(4) |
| N(10)-C(9)-Ru(1) | 138.2(4) |
| C(9)-N(10)-C(11) | 110.7(5) |
| C(9)-N(10)-C(23) | 127.9(5) |
| C(11)-N(10)-C(23) | 121.0(5) |
| C(12)-C(11)-N(10) | 108.0(5) |
| C(11)-C(12)-N(13) | 105.6(5) |
| C(9)-N(13)-C(12) | 112.9(5) |
| C(9)-N(13)-C(14) | 122.2(5) |
| C(12)-N(13)-C(14) | 124.9(5) |
| C(19)-C(14)-C(15) | 122.1(5) |
| C(19)-C(14)-N(13) | 119.0(5) |
| C(15)-C(14)-N(13) | 118.8(5) |
| C(16)-C(15)-C(14) | 117.5(6) |
| C(16)-C(15)-C(22) | 119.5(6) |
| C(14)-C(15)-C(22) | 123.0(5) |
| C(15)-C(16)-C(17) | 121.9(6) |
| C(16)-C(17)-C(18) | 118.6(6) |
| C(16)-C(17)-C(21) | 120.7(7) |
| C(18)-C(17)-C(21) | 120.7(7) |
| C(19)-C(18)-C(17) | 122.7(6) |
| C(18)-C(19)-C(14) | 117.0(6) |
| C(18)-C(19)-C(20) | 120.8(6) |
| C(14)-C(19)-C(20) | 122.2(6) |
| C(28)-C(23)-C(24) | 122.3(6) |
| C(28)-C(23)-N(10) | 119.7(5) |
| C(24)-C(23)-N(10) | 117.8(5) |
| C(25)-C(24)-C(23) | 117.3(6) |
| C(25)-C(24)-C(31) | 121.0(6) |
| C(23)-C(24)-C(31) | 121.7(6) |
| C(24)-C(25)-C(26) | 122.5(6) |
| C(25)-C(26)-C(27) | 117.6(6) |
| C(25)-C(26)-C(30) | 120.4(7) |
| C(27)-C(26)-C(30) | 122.0(7) |
| C(28)-C(27)-C(26) | 123.3(7) |
| C(27)-C(28)-C(23) | 116.9(6) |
| C(27)-C(28)-C(29) | 120.7(6) |
| C(23)-C(28)-C(29) | 122.4(6) |
| C(33)-N(32)-C(37) | 116.0(5) |
| C(33)-N(32)-Ru(1) | 124.0(4) |
| C(37)-N(32)-Ru(1) | 119.9(4) |
| N(32)-C(33)-C(34) | 124.3(6) |
| C(35)-C(34)-C(33) | 118.9(6) |
| C(34)-C(35)-C(36) | 118.3(7) |
| C(35)-C(36)-C(37) | 119.8(7) |
| N(32)-C(37)-C(36) | 122.7(6) |
| C(39)-O(38)-Ru(1) | 125.9(4) |
| O(38)-C(39)-C(48) | 124.6(5) |
| O(38)-C(39)-C(40) | 116.7(5) |
| C(48)-C(39)-C(40) | 118.6(5) |
| C(41)-C(40)-C(39) | 121.6(6) |
| C(40)-C(41)-C(42) | 121.2(6) |
| C(41)-C(42)-C(43) | 122.9(6) |
| C(41)-C(42)-C(47) | 118.8(6) |
| C(43)-C(42)-C(47) | 118.3(6) |
| C(44)-C(43)-F(52) | 118.1(6) |
| C(44)-C(43)-C(42) | 123.3(6) |
| F(52)-C(43)-C(42) | 118.6(6) |
| C(43)-C(44)-F(51) | 122.5(7) |
| C(43)-C(44)-C(45) | 118.6(6) |
| F(51)-C(44)-C(45) | 118.9(7) |
| F(50)-C(45)-C(46) | 122.4(6) |
| F(50)-C(45)-C(44) | 118.0(6) |
| C(46)-C(45)-C(44) | 119.5(6) |
| C(45)-C(46)-F(49) | 115.2(6) |
| C(45)-C(46)-C(47) | 124.1(6) |
| F(49)-C(46)-C(47) | 120.6(6) |
| C(46)-C(47)-C(42) | 115.9(6) |
| C(46)-C(47)-C(48) | 124.8(6) |
| C(42)-C(47)-C(48) | 119.3(6) |
| C(39)-C(48)-C(47) | 119.7(5) |
| C(39)-C(48)-C(55) | 119.3(5) |
| C(47)-C(48)-C(55) | 121.0(5) |
| C(54)-O(53)-Ru(1) | 115.0(3) |
| O(53)-C(54)-C(55) | 121.7(5) |
| O(53)-C(54)-C(63) | 119.7(5) |
| C(55)-C(54)-C(63) | 118.5(5) |
| C(54)-C(55)-C(56) | 120.7(5) |
| C(54)-C(55)-C(48) | 118.3(5) |
| C(56)-C(55)-C(48) | 121.0(5) |
| C(57)-C(56)-C(55) | 126.4(5) |

TABLE 19-continued

Bond lengths [Å] and angles [°] for df302.

| | |
|---|---|
| C(57)-C(56)-C(61) | 114.9(5) |
| C(55)-C(56)-C(61) | 118.7(5) |
| F(67)-C(57)-C(58) | 116.7(6) |
| F(67)-C(57)-C(56) | 120.1(5) |
| C(58)-C(57)-C(56) | 123.2(6) |
| C(57)-C(58)-F(66) | 121.2(6) |
| C(57)-C(58)-C(59) | 121.7(6) |
| F(66)-C(58)-C(59) | 117.1(6) |
| F(65)-C(59)-C(60) | 121.5(6) |
| F(65)-C(59)-C(58) | 120.5(7) |
| C(60)-C(59)-C(58) | 118.0(6) |
| F(64)-C(60)-C(59) | 118.8(6) |
| F(64)-C(60)-C(61) | 118.3(6) |
| C(59)-C(60)-C(61) | 122.9(6) |
| C(62)-C(61)-C(60) | 122.2(6) |
| C(62)-C(61)-C(56) | 118.5(6) |
| C(60)-C(61)-C(56) | 119.3(6) |
| C(63)-C(62)-C(61) | 121.3(6) |
| C(62)-C(63)-C(54) | 121.8(6) |
| C(69)-O(68)-C(72) | 102.9(10) |
| C(70)-C(69)-O(68) | 106.1(13) |
| C(69)-C(70)-C(71) | 113.4(15) |
| C(72)-C(71)-C(70) | 102.7(14) |
| C(71)-C(72)-O(68) | 109.2(11) |

Symmetry transformations used to generate equivalent atoms:

TABLE 20

Anisotropic displacement parameters (Å$^2$ × 10$^3$) for df302.
The anisotropic displacement factor exponent takes the form:
$-2\pi^2[h^2 a^{*2}U^{11} + \ldots + 2 h k a^* b^* U^{12}]$

| | U11 | U22 | U33 | U23 | U13 | U12 |
|---|---|---|---|---|---|---|
| Ru(1) | 23(1) | 37(1) | 26(1) | 3(1) | 12(1) | 3(1) |
| C(2) | 27(3) | 46(4) | 33(3) | 8(3) | 16(3) | 7(3) |
| C(3) | 25(3) | 42(4) | 36(3) | 4(3) | 17(3) | 0(3) |
| C(4) | 29(3) | 48(4) | 54(4) | 6(3) | 20(3) | 1(3) |
| C(5) | 41(4) | 41(4) | 96(6) | 1(4) | 39(4) | 1(3) |
| C(6) | 41(4) | 43(4) | 86(6) | −14(4) | 35(4) | −9(3) |
| C(7) | 39(4) | 53(5) | 52(4) | −3(3) | 22(3) | −14(3) |
| C(8) | 32(3) | 43(4) | 51(4) | 9(3) | 25(3) | 0(3) |
| C(9) | 29(3) | 36(3) | 29(3) | −2(3) | 17(3) | 1(3) |
| N(10) | 22(2) | 39(3) | 25(2) | 2(2) | 12(2) | 2(2) |
| C(11) | 39(4) | 39(4) | 33(3) | 10(3) | 17(3) | 10(3) |
| C(12) | 37(4) | 41(4) | 37(3) | 8(3) | 20(3) | 2(3) |
| N(13) | 29(3) | 39(3) | 29(3) | 0(2) | 15(2) | 0(2) |
| C(14) | 32(3) | 36(3) | 31(3) | 2(3) | 18(3) | 0(3) |
| C(15) | 30(3) | 40(4) | 32(3) | −2(3) | 14(3) | −3(3) |
| C(16) | 41(4) | 55(4) | 38(3) | −3(3) | 21(3) | 0(3) |
| C(17) | 34(4) | 61(5) | 47(4) | −3(4) | 17(3) | 4(3) |
| C(18) | 38(4) | 58(5) | 56(4) | −7(4) | 28(4) | 1(3) |
| C(19) | 37(3) | 43(4) | 34(3) | −3(3) | 21(3) | −3(3) |
| C(20) | 52(4) | 60(4) | 46(4) | −6(4) | 33(4) | −6(4) |
| C(21) | 38(4) | 120(8) | 53(5) | −16(5) | 10(4) | 12(5) |
| C(22) | 35(4) | 50(4) | 42(4) | −11(3) | 20(3) | −6(3) |
| C(23) | 25(3) | 43(3) | 33(3) | 11(3) | 14(3) | 6(3) |
| C(24) | 40(4) | 47(4) | 36(3) | 11(3) | 24(3) | 13(3) |
| C(25) | 35(4) | 63(5) | 55(4) | 16(4) | 29(3) | 14(4) |
| C(26) | 30(3) | 67(5) | 46(4) | 11(4) | 18(3) | 5(3) |
| C(27) | 36(4) | 60(5) | 35(4) | 1(3) | 10(3) | −2(3) |
| C(28) | 31(3) | 49(4) | 25(3) | 6(3) | 9(3) | 4(3) |
| C(29) | 48(4) | 71(5) | 37(4) | −6(3) | 24(3) | 3(4) |
| C(30) | 32(4) | 121(8) | 66(5) | 7(5) | 22(4) | −2(5) |
| C(31) | 39(4) | 57(4) | 41(4) | 6(3) | 24(3) | 14(3) |
| N(32) | 34(3) | 40(3) | 32(3) | 3(2) | 21(2) | 0(2) |
| C(33) | 32(3) | 45(4) | 35(4) | −1(3) | 18(3) | −4(3) |
| C(34) | 58(5) | 66(5) | 35(4) | −12(3) | 30(4) | −10(4) |
| C(35) | 73(5) | 63(5) | 62(5) | 1(4) | 52(5) | 12(4) |
| C(36) | 49(4) | 71(5) | 53(5) | 15(4) | 35(4) | 23(4) |
| C(37) | 34(4) | 56(4) | 36(3) | 2(3) | 21(3) | 3(3) |
| O(38) | 32(2) | 49(3) | 26(2) | 5(2) | 14(2) | 13(2) |
| C(39) | 30(3) | 37(3) | 30(3) | 8(3) | 17(3) | 6(3) |
| C(40) | 29(3) | 42(4) | 42(4) | 5(3) | 22(3) | 3(3) |

TABLE 20-continued

Anisotropic displacement parameters (Å$^2$ × 10$^3$) for df302.
The anisotropic displacement factor exponent takes the form:
$-2\pi^2[h^2 a^{*2}U^{11} + \ldots + 2 h k a^* b^* U^{12}]$

| | U11 | U22 | U33 | U23 | U13 | U12 |
|---|---|---|---|---|---|---|
| C(41) | 29(3) | 43(4) | 40(4) | 6(3) | 15(3) | −1(3) |
| C(42) | 32(3) | 40(4) | 39(4) | 2(3) | 19(3) | −4(3) |
| C(43) | 33(3) | 49(4) | 34(3) | 0(3) | 15(3) | −10(3) |
| C(44) | 53(4) | 62(5) | 36(4) | −13(4) | 22(3) | −23(4) |
| C(45) | 50(4) | 77(5) | 44(4) | −17(4) | 32(4) | −14(4) |
| C(46) | 40(4) | 64(5) | 51(4) | −17(3) | 33(4) | −14(3) |
| C(47) | 31(3) | 46(4) | 29(3) | 2(3) | 15(3) | −3(3) |
| C(48) | 25(3) | 42(4) | 31(3) | 6(3) | 15(3) | 1(3) |
| F(49) | 45(2) | 111(4) | 69(3) | −42(3) | 38(2) | −14(2) |
| F(50) | 85(4) | 137(5) | 76(3) | −53(3) | 61(3) | −28(3) |
| F(51) | 74(3) | 100(4) | 42(2) | −27(2) | 27(3) | −29(3) |
| F(52) | 34(2) | 77(3) | 45(2) | −3(2) | 10(2) | −11(2) |
| O(53) | 33(2) | 41(2) | 38(2) | 5(2) | 22(2) | 7(2) |
| C(54) | 35(3) | 35(4) | 36(3) | −3(3) | 23(3) | 2(3) |
| C(55) | 22(3) | 47(4) | 25(3) | −3(3) | 13(3) | 0(3) |
| C(56) | 31(3) | 37(3) | 34(3) | −3(3) | 20(3) | 0(3) |
| C(57) | 34(3) | 51(4) | 37(3) | −4(3) | 23(3) | −1(3) |
| C(58) | 54(4) | 43(4) | 39(4) | 7(3) | 30(3) | 6(3) |
| C(59) | 67(5) | 52(4) | 59(5) | −1(4) | 52(4) | −6(4) |
| C(60) | 33(3) | 53(4) | 56(4) | −11(3) | 32(3) | −11(3) |
| C(61) | 32(3) | 46(4) | 40(4) | −5(3) | 25(3) | −1(3) |
| C(62) | 30(3) | 58(4) | 53(4) | 0(3) | 25(3) | 4(3) |
| C(63) | 28(3) | 56(4) | 38(3) | 6(3) | 17(3) | 7(3) |
| F(64) | 45(2) | 67(3) | 83(3) | −9(2) | 45(2) | −11(2) |
| F(65) | 85(3) | 76(3) | 84(3) | 12(3) | 67(3) | −7(3) |
| F(66) | 69(3) | 72(3) | 56(3) | 25(2) | 42(2) | 13(2) |
| F(67) | 34(2) | 68(3) | 45(2) | 17(2) | 20(2) | 6(2) |
| O(68) | 134(8) | 146(8) | 120(7) | 19(6) | 86(7) | −9(6) |
| C(69) | 175(16) | 124(12) | 260(20) | −17(12) | 177(17) | −39(11) |
| C(70) | 260(20) | 172(17) | 310(30) | −72(17) | 260(20) | −57(15) |
| C(71) | 181(18) | 200(20) | 260(20) | −106(17) | 181(19) | −88(15) |
| C(72) | 155(14) | 206(17) | 92(9) | −59(10) | 85(10) | −75(12) |

TABLE 21

Hydrogen coordinates (×10$^4$) and isotropic displacement parameters
(Å$^2$ × 10$^3$) for df302.

| | x | y | z | U(eq) |
|---|---|---|---|---|
| H(2A) | 3148 | 1487 | 2698 | 45 |
| H(4A) | 3780 | −1059 | 3104 | 57 |
| H(5A) | 3550 | −2939 | 2638 | 75 |
| H(6A) | 2895 | −3208 | 1751 | 72 |
| H(7A) | 2438 | −1625 | 1333 | 63 |
| H(8A) | 2648 | 240 | 1820 | 52 |
| H(11A) | 3120 | 5040 | 1478 | 49 |
| H(12A) | 3860 | 5451 | 2140 | 49 |
| H(16A) | 5031 | 4416 | 4627 | 57 |
| H(18A) | 5195 | 3117 | 3434 | 62 |
| H(20A) | 4612 | 2485 | 2384 | 76 |
| H(20B) | 4446 | 3812 | 2156 | 76 |
| H(20C) | 4164 | 2817 | 2128 | 76 |
| H(21A) | 5731 | 4383 | 4892 | 125 |
| H(21B) | 5781 | 3567 | 4469 | 125 |
| H(21C) | 5696 | 2967 | 4902 | 125 |
| H(22A) | 3983 | 5099 | 3497 | 67 |
| H(22B) | 4379 | 5524 | 4158 | 67 |
| H(22C) | 4184 | 4251 | 4086 | 67 |
| H(25A) | 2207 | 3562 | 2057 | 60 |
| H(27A) | 2086 | 1720 | 694 | 62 |
| H(29A) | 2587 | 2192 | 502 | 81 |
| H(29B) | 2877 | 1250 | 1039 | 81 |
| H(29C) | 3034 | 2572 | 1085 | 81 |
| H(30A) | 1580 | 1480 | 856 | 118 |
| H(30B) | 1467 | 2859 | 799 | 118 |
| H(30C) | 1642 | 2147 | 1420 | 118 |
| H(31A) | 3035 | 5182 | 2554 | 69 |
| H(31B) | 3189 | 4078 | 3016 | 69 |
| H(31C) | 2781 | 4752 | 2771 | 69 |

TABLE 21-continued

Hydrogen coordinates (×10⁴) and isotropic displacement parameters ($Å^2 × 10^3$) for df302.

| | x | y | z | U(eq) |
|---|---|---|---|---|
| H(33A) | 3560 | 761 | 1930 | 48 |
| H(34A) | 3787 | −378 | 1503 | 63 |
| H(35A) | 4474 | −923 | 2121 | 71 |
| H(36A) | 4901 | −357 | 3168 | 67 |
| H(37A) | 4642 | 715 | 3572 | 51 |
| H(40A) | 5072 | 1219 | 4761 | 45 |
| H(41A) | 5483 | 1879 | 5766 | 49 |
| H(62A) | 2803 | 1127 | 3831 | 57 |
| H(63A) | 2991 | 2306 | 3369 | 52 |
| H(69A) | 2976 | −1871 | 508 | 189 |
| H(69B) | 3301 | −2316 | 1210 | 189 |
| H(70A) | 3669 | −2976 | 1040 | 228 |
| H(70B) | 3390 | −2306 | 389 | 228 |
| H(71A) | 3236 | −3968 | −56 | 223 |
| H(71B) | 3486 | −4648 | 599 | 223 |
| H(72A) | 2910 | −5151 | 311 | 174 |
| H(72B) | 2684 | −4128 | −206 | 174 |

TABLE 22

Torsion angles [°] for df302.

| | |
|---|---|
| C(9)-Ru(1)-C(2)-C(3) | 121.0(6) |
| O(38)-Ru(1)-C(2)-C(3) | −59.6(6) |
| O(53)-Ru(1)-C(2)-C(3) | −147.4(6) |
| N(32)-Ru(1)-C(2)-C(3) | 28.9(6) |
| Ru(1)-C(2)-C(3)-C(8) | −152.8(5) |
| Ru(1)-C(2)-C(3)-C(4) | 28.7(9) |
| C(8)-C(3)-C(4)-C(5) | 1.7(10) |
| C(2)-C(3)-C(4)-C(5) | −179.8(6) |
| C(3)-C(4)-C(5)-C(6) | 1.1(12) |
| C(4)-C(5)-C(6)-C(7) | −2.1(13) |
| C(5)-C(6)-C(7)-C(8) | 0.1(12) |
| C(4)-C(3)-C(8)-C(7) | −3.7(10) |
| C(2)-C(3)-C(8)-C(7) | 177.7(6) |
| C(6)-C(7)-C(8)-C(3) | 2.9(11) |
| C(2)-Ru(1)-C(9)-N(13) | −170.6(4) |
| O(38)-Ru(1)-C(9)-N(13) | 10.7(7) |
| O(53)-Ru(1)-C(9)-N(13) | 100.4(4) |
| N(32)-Ru(1)-C(9)-N(13) | −74.4(4) |
| C(2)-Ru(1)-C(9)-N(10) | 10.1(6) |
| O(38)-Ru(1)-C(9)-N(10) | −168.7(4) |
| O(53)-Ru(1)-C(9)-N(10) | −78.9(6) |
| N(32)-Ru(1)-C(9)-N(10) | 106.3(6) |
| N(13)-C(9)-N(10)-C(11) | 0.7(6) |
| Ru(1)-C(9)-N(10)-C(11) | −179.9(5) |
| N(13)-C(9)-N(10)-C(23) | −172.0(5) |
| Ru(1)-C(9)-N(10)-C(23) | 7.3(9) |
| C(9)-N(10)-C(11)-C(12) | −0.4(7) |
| C(23)-N(10)-C(11)-C(12) | 172.9(5) |
| N(10)-C(11)-C(12)-N(13) | −0.1(7) |
| N(10)-C(9)-N(13)-C(12) | −0.8(6) |
| Ru(1)-C(9)-N(13)-C(12) | 179.7(4) |
| N(10)-C(9)-N(13)-C(14) | 177.8(5) |
| Ru(1)-C(9)-N(13)-C(14) | −1.7(7) |
| C(11)-C(12)-N(13)-C(9) | 0.6(7) |
| C(11)-C(12)-N(13)-C(14) | −178.0(5) |
| C(9)-N(13)-C(14)-C(19) | 106.6(7) |
| C(12)-N(13)-C(14)-C(19) | −75.0(8) |
| C(9)-N(13)-C(14)-C(15) | −77.3(7) |
| C(12)-N(13)-C(14)-C(15) | 101.2(7) |
| C(19)-C(14)-C(15)-C(16) | −4.2(9) |
| N(13)-C(14)-C(15)-C(16) | 179.8(6) |
| C(19)-C(14)-C(15)-C(22) | 174.0(6) |
| N(13)-C(14)-C(15)-C(22) | −2.0(9) |
| C(14)-C(15)-C(16)-C(17) | 2.3(10) |
| C(22)-C(15)-C(16)-C(17) | −175.9(6) |
| C(15)-C(16)-C(17)-C(18) | 0.5(11) |
| C(15)-C(16)-C(17)-C(21) | 179.3(7) |
| C(16)-C(17)-C(18)-C(19) | −1.7(11) |
| C(21)-C(17)-C(18)-C(19) | 179.5(7) |
| C(17)-C(18)-C(19)-C(14) | 0.0(10) |
| C(17)-C(18)-C(19)-C(20) | 177.4(7) |
| C(15)-C(14)-C(19)-C(18) | 3.1(9) |
| N(13)-C(14)-C(19)-C(18) | 179.1(6) |
| C(15)-C(14)-C(19)-C(20) | −174.4(6) |
| N(13)-C(14)-C(19)-C(20) | 1.7(9) |
| C(9)-N(10)-C(23)-C(28) | −104.9(7) |
| C(11)-N(10)-C(23)-C(28) | 83.0(7) |
| C(9)-N(10)-C(23)-C(24) | 80.8(8) |
| C(11)-N(10)-C(23)-C(24) | −91.3(7) |
| C(28)-C(23)-C(24)-C(25) | 3.8(9) |
| N(10)-C(23)-C(24)-C(25) | 177.9(5) |
| C(28)-C(23)-C(24)-C(31) | −174.8(6) |
| N(10)-C(23)-C(24)-C(31) | −0.6(8) |
| C(23)-C(24)-C(25)-C(26) | −2.0(10) |
| C(31)-C(24)-C(25)-C(26) | 176.6(6) |
| C(24)-C(25)-C(26)-C(27) | −0.6(10) |
| C(24)-C(25)-C(26)-C(30) | −179.0(7) |
| C(25)-C(26)-C(27)-C(28) | 1.7(11) |
| C(30)-C(26)-C(27)-C(28) | −180.0(7) |
| C(26)-C(27)-C(28)-C(23) | 0.0(10) |
| C(26)-C(27)-C(28)-C(29) | −178.0(7) |
| C(24)-C(23)-C(28)-C(27) | −2.8(9) |
| N(10)-C(23)-C(28)-C(27) | −176.8(6) |
| C(24)-C(23)-C(28)-C(29) | 175.2(6) |
| N(10)-C(23)-C(28)-C(29) | 1.1(9) |
| C(2)-Ru(1)-N(32)-C(33) | 37.1(5) |
| C(9)-Ru(1)-N(32)-C(33) | −57.0(5) |
| O(38)-Ru(1)-N(32)-C(33) | 150.7(5) |
| O(53)-Ru(1)-N(32)-C(33) | 180(100) |
| C(2)-Ru(1)-N(32)-C(37) | −141.1(5) |
| C(9)-Ru(1)-N(32)-C(37) | 124.7(5) |
| O(38)-Ru(1)-N(32)-C(37) | −27.5(5) |
| O(53)-Ru(1)-N(32)-C(37) | 1.6(19) |
| C(37)-N(32)-C(33)-C(34) | 1.9(9) |
| Ru(1)-N(32)-C(33)-C(34) | −176.5(5) |
| N(32)-C(33)-C(34)-C(35) | −2.4(11) |
| C(33)-C(34)-C(35)-C(36) | 1.2(11) |
| C(34)-C(35)-C(36)-C(37) | 0.3(11) |
| C(33)-N(32)-C(37)-C(36) | −0.2(9) |
| Ru(1)-N(32)-C(37)-C(36) | 178.1(5) |
| C(35)-C(36)-C(37)-N(32) | −0.8(11) |
| C(2)-Ru(1)-O(38)-C(39) | −119.2(5) |
| C(9)-Ru(1)-O(38)-C(39) | 59.4(6) |
| O(53)-Ru(1)-O(38)-C(39) | −31.2(5) |
| N(32)-Ru(1)-O(38)-C(39) | 145.8(5) |
| Ru(1)-O(38)-C(39)-C(48) | 63.0(7) |
| Ru(1)-O(38)-C(39)-C(40) | −120.5(5) |
| O(38)-C(39)-C(40)-C(41) | −178.4(6) |
| C(48)-C(39)-C(40)-C(41) | −1.7(9) |
| C(39)-C(40)-C(41)-C(42) | −4.3(9) |
| C(40)-C(41)-C(42)-C(43) | −177.9(6) |
| C(40)-C(41)-C(42)-C(47) | 2.9(9) |
| C(41)-C(42)-C(43)-C(44) | 177.6(7) |
| C(47)-C(42)-C(43)-C(44) | −3.2(10) |
| C(41)-C(42)-C(43)-F(52) | −2.4(10) |
| C(47)-C(42)-C(43)-F(52) | 176.9(5) |
| F(52)-C(43)-C(44)-F(51) | −2.0(10) |
| C(42)-C(43)-C(44)-F(51) | 178.1(6) |
| F(52)-C(43)-C(44)-C(45) | 179.4(6) |
| C(42)-C(43)-C(44)-C(45) | −0.6(11) |
| C(43)-C(44)-C(45)-F(50) | −176.5(7) |
| F(51)-C(44)-C(45)-F(50) | 4.8(11) |
| C(43)-C(44)-C(45)-C(46) | 2.0(12) |
| F(51)-C(44)-C(45)-C(46) | −176.7(7) |
| F(50)-C(45)-C(46)-F(49) | 2.5(11) |
| C(44)-C(45)-C(46)-F(49) | −175.9(7) |
| F(50)-C(45)-C(46)-C(47) | 178.9(7) |
| C(44)-C(45)-C(46)-C(47) | 0.5(12) |
| C(45)-C(46)-C(47)-C(42) | −4.1(11) |
| F(49)-C(46)-C(47)-C(42) | 172.1(6) |
| C(45)-C(46)-C(47)-C(48) | 176.1(7) |
| F(49)-C(46)-C(47)-C(48) | −7.7(10) |
| C(41)-C(42)-C(47)-C(46) | −175.5(6) |
| C(43)-C(42)-C(47)-C(46) | 5.2(9) |
| C(41)-C(42)-C(47)-C(48) | 4.3(9) |
| C(43)-C(42)-C(47)-C(48) | −175.0(6) |

TABLE 22-continued

Torsion angles [°] for df302.

| | |
|---|---:|
| O(38)-C(39)-C(48)-C(47) | −174.7(5) |
| C(40)-C(39)-C(48)-C(47) | 8.8(9) |
| O(38)-C(39)-C(48)-C(55) | 7.4(9) |
| C(40)-C(39)-C(48)-C(55) | −169.0(5) |
| C(46)-C(47)-C(48)-C(39) | 169.6(6) |
| C(42)-C(47)-C(48)-C(39) | −10.2(9) |
| C(46)-C(47)-C(48)-C(55) | −12.7(10) |
| C(42)-C(47)-C(48)-C(55) | 167.6(6) |
| C(2)-Ru(1)-O(53)-C(54) | 56.2(4) |
| C(9)-Ru(1)-O(53)-C(54) | 150.1(4) |
| O(38)-Ru(1)-O(53)-C(54) | −57.7(4) |
| N(32)-Ru(1)-O(53)-C(54) | −86.8(17) |
| Ru(1)-O(53)-C(54)-C(55) | 78.4(6) |
| Ru(1)-O(53)-C(54)-C(63) | −104.4(5) |
| O(53)-C(54)-C(55)-C(56) | −175.4(5) |
| C(63)-C(54)-C(55)-C(56) | 7.4(8) |
| O(53)-C(54)-C(55)-C(48) | 6.5(8) |
| C(63)-C(54)-C(55)-C(48) | −170.6(5) |
| C(39)-C(48)-C(55)-C(54) | −66.5(8) |
| C(47)-C(48)-C(55)-C(54) | 115.7(6) |
| C(39)-C(48)-C(55)-C(56) | 115.4(6) |
| C(47)-C(48)-C(55)-C(56) | −62.4(8) |
| C(54)-C(55)-C(56)-C(57) | 173.4(6) |
| C(48)-C(55)-C(56)-C(57) | −8.6(9) |
| C(54)-C(55)-C(56)-C(61) | −7.1(8) |
| C(48)-C(55)-C(56)-C(61) | 170.9(5) |
| C(55)-C(56)-C(57)-F(67) | −5.7(9) |
| C(61)-C(56)-C(57)-F(67) | 174.9(5) |
| C(55)-C(56)-C(57)-C(58) | 177.8(6) |
| C(61)-C(56)-C(57)-C(58) | −1.6(9) |
| F(67)-C(57)-C(58)-F(66) | 3.4(9) |
| C(56)-C(57)-C(58)-F(66) | 180.0(6) |
| F(67)-C(57)-C(58)-C(59) | −177.0(6) |
| C(56)-C(57)-C(58)-C(59) | −0.4(10) |
| C(57)-C(58)-C(59)-F(65) | 179.6(6) |
| F(66)-C(58)-C(59)-F(65) | −0.8(10) |
| C(57)-C(58)-C(59)-C(60) | 1.4(10) |
| F(66)-C(58)-C(59)-C(60) | −179.0(6) |
| F(65)-C(59)-C(60)-F(64) | 2.7(10) |
| C(58)-C(59)-C(60)-F(64) | −179.0(6) |
| F(65)-C(59)-C(60)-C(61) | −178.4(6) |
| C(58)-C(59)-C(60)-C(61) | −0.2(10) |
| F(64)-C(60)-C(61)-C(62) | −2.6(9) |
| C(59)-C(60)-C(61)-C(62) | 178.6(7) |
| F(64)-C(60)-C(61)-C(56) | 176.9(5) |
| C(59)-C(60)-C(61)-C(56) | −2.0(10) |
| C(57)-C(56)-C(61)-C(62) | −177.8(6) |
| C(55)-C(56)-C(61)-C(62) | 2.7(9) |
| C(57)-C(56)-C(61)-C(60) | 2.7(8) |
| C(55)-C(56)-C(61)-C(60) | −176.8(6) |
| C(60)-C(61)-C(62)-C(63) | −179.2(6) |
| C(56)-C(61)-C(62)-C(63) | 1.3(10) |
| C(61)-C(62)-C(63)-C(54) | −1.0(10) |
| O(53)-C(54)-C(63)-C(62) | 179.4(6) |
| C(55)-C(54)-C(63)-C(62) | −3.4(9) |
| C(72)-O(68)-C(69)-C(70) | −20.5(19) |
| O(68)-C(69)-C(70)-C(71) | 11(3) |
| C(69)-C(70)-C(71)-C(72) | 5(3) |
| C(70)-C(71)-C(72)-O(68) | −18(2) |
| C(69)-O(68)-C(72)-C(71) | 24.5(19) |

Symmetry transformations used to generate equivalent atoms:

REFERENCES (1) Recent reviews: (a) Trnka, T. M.; Grubbs, R. H. *Acc. Chem. Res.* 2001, 34, 18. (b) Fürstner, A. *Angew. Chem. Int. Ed.* 2000, 39, 3012. (c) Schrock, R. R. *Tetrahedron*, 1999, 55, 8141. (d) Buchmeiser, M. R. *Chem. Rev.* 2000, 100, 1565.

(2) Sanford, M. S.; Love, J. A.; Grubbs, R. H. *Organometallics* 2001, 20, 5314.

(3) (a) Huang, J.; Stevens, E. D.; Nolan, S. P.; Peterson, J. L. *J. Am. Chem. Soc.* 1999, 121, 2674. (b) Huang, J.; Schanz, H. -J.; Stevens, E. D.; Nolan, S. P. *Organometallics* 1999, 18, 5375.

(4) Weskamp, T.; Kohl, F. J.; Hieringer, W.; Gleich, D.; Herrmann, W. A. *Angew. Chem. Int. Ed.* 1999, 38, 2416.

(5) (a) Conrad, J. C.; Yap, G. P. A.; Fogg, D. E. *Organometallics* 2003, 22, 1986. (b) Volland, M. A. O.; Rominger, F.; Eisentrager, F.; Hofmann, P. *J. Organomet. Chem.* 2002, 641, 220. (c) D. Amoroso, J. L. Snelgrove, J. C. Conrad, S. D. Drouin, G. P. A. Yap, D. E. Fogg, *Adv. Synth. Catal.* 2002, 344, 757.

(6) Hoveyda, A. H.; Schrock, R. R. *Chem. Eur. J.* 2001, 7, 945.

(7) (a) McConville, D. H.; Wolf, J. R.; Schrock, R. R. *J. Am. Chem. Soc.* 1993, 115, 4413. (b) Totland, K. M.; Boyd, T. J.; LaVoie, G. G.; Davis, W. M.; Schrock, R. R. *Macromolecules* 1996, 29, 6114.

(8) Tsang, W. C. P.; Hultzsch, K. C.; Alexander, J. B.; P. J. Bonitatebus, J.; Schrock, R. R.; Hoveyda, A. H. *J. Am. Chem. Soc* 2003, 125, 2652.

(9) Chloride exchange reactions of 1a and related species with silver carboxylates yield dimeric products that exhibit low to moderate activity for RCM of diethyldiallylmalonate. (a) Buchowicz, W.; Ingold, F.; Mol, J. C.; Lutz, M.; Spek, A. L. *Chem. Eur. J.* 2001, 7, 2842. (b) Buchowicz, W.; Mol, J. C.; Lutz, M.; Spek, A. L. *J. Organomet. Chem.* 1999, 588, 205. The corresponding exchange of chloride for trifluoroacetate in a $PPh_3$-Ru alkylidene system gave slightly increased activity for metathesis of functionalized olefins: (c) Wu, Z.; Nguyen, S. T.; Grubbs, R. H.; Ziller, J. W. *J. Am. Chem. Soc.* 1995, 117, 5503. Schiff base derivatives exhibit RCM activity at elevated temperatures, and metathesis activity in polar, protic media: (d) Chang, S.; Jones, L.; Wang, C.; Henling, L. M.; Grubbs, R. H. *Organometallics* 1998, 17, 3460.

(10) A heterobifunctional carbene-phenoxide derivative was recently devised through an elegant NHC elaboration strategy. Van Veldhuizen, J. J.; Garber, S. B.; Kingsbury, J. S.; Hoveyda, A. H. *J. Am. Chem. Soc.* 2002, 124, 4954.

(11) Coalter, J. N.; Bollinger, J. C.; Eisenstein, O.; Caulton, K. G. New. *J. Chem.* 2000, 24, 925.

(12) Sanford, M. S.; Henling, L. M.; Day, M. W.; Grubbs, R. H. *Angew. Chem. Int. Ed.* 2000, 39, 3451.

(13) Arduengo, A. J.; Dias, H. V. R.; Harlow, R. L.; Kline, M. *J. Am. Chem. Soc.* 1992, 114, 5530.

(14) Scholl, M.; Ding, S.; Lee, C. W.; Grubbs, R. H. *Org. Lett.* 1999, 1, 953.

(15)(a) Sanford, M. S.; Love, J. A.; Grubbs, R. H. *J. Am. Chem. Soc.* 2001, 123, 6543. (b) Ulman, M.; Grubbs, R. H. *J. Org. Chem.* 1999, 64, 7202.

(16) Turnover numbers are considerably increased for crossmetathesis or RCM in neat substrate, with TON values for 6a in some cases exceeding 200,000. Dinger, M. B.; Mol, J. C. *Adv. Synth. Catal.* 2002, 344, 671.

(17) Fürstner, A.; Ackermann, L. *J. Chem. Soc., Chem. Commun.* 1999, 95.

(18) Connon, S. J.; Blechert, S. *Angew Chem Int Ed* 2003, 42, 1900–1923.

(19) Schurer, C. S.; Gessler, S.; Buschmann, N.; Blechert, S. *Angew Chem Int Ed* 2000, 39, 3898–3891.

(20) Conrad, J. C.; Amoroso, D.; Czechura, P.; Yap, G. P. A.; Fogg, D. E. *Organometallics* 2003, 22, 3634.

(21) Krause, J. O.; Nuyken, O.; Wurst, K.; Buchmeiser, M. R. *Chem. Eur. J.*, 2004, 10, 777.

(22) Buchowicz, W.; Ingold, F.; Mol, J. C.; Lutz, M.; Spek, A. L. *Chem. Eur. J.* 2001 7, 2842.

(23) Sanford, M. S.; Henling, L. M.; Day, M. W.; Grubbs, R. H. *Angew. Chem., Int. Ed.* 2000, 39, 3451.
(24) Chang, S.; Jones II, L.; Wang, C.; Henling, L. M.; Grubbs, R. H. *Organometallics* 1998, 17, 3460.
(25) Clerq, B. D.; Verport, F. *Adv. Syn. Catal.* 2002, 344, 639.
(26) Schmidt, B.; Pohler, M.; Costisella, B. *J. Org. Chem.* 2004, ASAP.
(27) Braddock, D. C.; Wildsmith, A. *J. Tett. Lett.* 2001, 3239.
(28) Furstner, A.; Langemann, K. *J. Org. Chem.* 1996, 61, 3942.
(29) Furstner, A.; Theil, O. R.; Ackermann, L.; Schanz, H. J.; Nolan, S. P. *J. Org. Chem.* 2000, 65, 2204.

The invention claimed is:

1. A compound of the formula Ia or Ib:

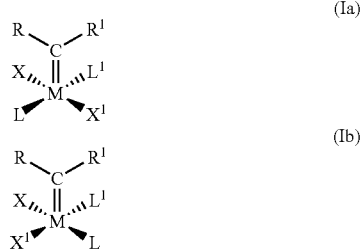

wherein:
M is selected from the group consisting of Ru and Os;
R and $R^1$ are independently selected from the group consisting of hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_{2-20}$ alkenyloxy, aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl; each optionally substituted with one or more $C_1$–$C_5$ alkyl, halogen, $C_1$–$C_5$ alkoxy, phenyl optionally substituted with halogen, $C_1$–$C_5$ alkyl, or $C_1$–$C_5$ alkoxy;
X and $X^1$ are anionic ligands, wherein X and $X^1$ are each independently selected from -Z-Q, or wherein one of X and $X^1$ is halide and the other of X and $X^1$ is -Z-Q, each Z comprising O, S, N, or C, and each Q comprising a planar electron withdrawing group; and
L and $L^1$ are independently selected from any neutral electron donor;
wherein any 2–3 of X, $X^1$, L, or $L^1$ are optionally covalently linked to form a chelating multidentate ligand.

2. The compound according to claim 1, wherein each Q is a $C_3$–$C_{20}$ heterocyclic or aromatic cyclic, bicyclic, or multicyclic ring system that is unsubstituted or substituted with 1–20 electron-withdrawing groups and/or one or more $C_1$–$C_{10}$ alkyl groups.

3. The compound according to claim 1, wherein each Z is S and each Q is CN.

4. The compound according to claim 2, wherein the electron-withdrawing groups are each independently selected from the group consisting of $NO_2$, $CF_3$, halide, ester, and ketone groups.

5. The compound according to claim 2, wherein at least one Q is a 6-carbon ring substituted in at least one position by a halide atom.

6. The compound according to claim 5, wherein at least one Q is selected from $C_6F_5$, $C_6Cl_5$, and $C_6Br_5$.

7. The compound according to claim 6, wherein at least one of X and $X^1$ is $OC_6Br_5$.

8. The compound according to claim 1, wherein X and $X^1$ are linked to form a multidentate chelating ligand.

9. The compound according to claim 8, wherein X and $X^1$ are linked to form a diolate, biphenolate or binaphthalate group that is unsubstituted or substituted with at least one halide.

10. The compound according to claim 9, wherein the biphenolate group is of the formula $O_2C_{12}F_8$.

11. The compound according to claim 1, wherein:
one of L and $L^1$ is selected from the group consisting of N,N'-bis(mesityl)imidazol-2-ylidene (IMes), N,N'-bis-(mesityl)-imidazolidine ($H_2$IMes), N,N'-bis($C_3$–$C_{12}$ aryl or $C_1$–$C_{12}$ alkyl)imidazolidine and N,N'-bis ($C_1$–$C_{12}$ alkyl or $C_3$–$C_{12}$ aryl)imidazol-2-ylidene;
and the other of L or $L^1$ is pyridine unsubstituted or substituted with one or more electron withdrawing groups.

12. The compound according to claim 11, wherein the pyridine group is substituted in the 3-position by Br.

13. The compound according to claim 1, wherein each Z is oxygen.

14. A catalyst for catalyzing olefin metathesis reactions, the catalyst comprising a compound according to claim 1, wherein M is Ru.

15. The catalyst according to claim 14, wherein the olefin metathesis reaction comprises a reaction selected from ring-closing metathesis, ring-opening metathesis and cross-metathesis.

16. The catalyst according to claim 14, wherein the catalyst is capable of generating stereospecific products.

17. The catalyst according to claim 14, wherein the catalyst is tethered to a solid support.

18. The catalyst according to claim 17, wherein the catalyst is tethered through X, or $X^1$, or through both X and $X^1$.

19. The catalyst according to claim 18, wherein the catalyst remains catalytically active without separation from the solid support.

20. The catalyst according to claim 19, wherein the solid support is selected from the group consisting of Sepharose™, glass beads, magnetic beads, and polystyrene.

21. The catalyst according to claim 14, wherein the catalyst remains active in fluorous reaction media.

22. A method for olefin metathesis, the method comprising the steps of exposing the olefin to a catalyst of claim 14, and purifying or partially purifying the products.

23. The method according to claim 22, wherein the olefin metathesis reaction is selected from ring-closing metathesis, ring opening metathesis, and cross-metathesis.

24. A method for producing a catalyst for olefin metathesis reactions, comprising the steps of:
providing a compound according to forumla I as shown in claim 1, wherein M is Ru, X and $X^1$ are halide, and each L a neutral ligand;
reacting the compound with TlOY, wherein Y is a cyclic or bicyclic carbon-ring system comprising from 3 to 12 carbon atoms that are unsubstituted, or substituted with from 1 to 10 electron-withdrawing groups; and
purifying or partially purifying the catalyst.

25. The method according to claim 24, wherein X and $X^1$ are Cl, and one of L or $L^1$ is pyridine, optionally substituted with one or more electron withdrawing groups, and the other of L and $L^1$ is IMes.

26. A compound of formula III:

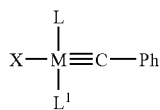

(III)

wherein M is Ru or Os;
X is an anionic ligand of the formula -Z-Q, wherein each Z is selected from the group consisting of unsubstituted or substituted O, S, N, or C and each Q comprises a planar electron withdrawing group; and
L and $L^1$ are independently selected from any neutral electron donor;
wherein any 2–3 of X, $X^1$, L, or $L^1$ are optionally covalently linked to form a chelating multidentate ligand.

27. The compound according to claim 26, wherein each Q is a $C_3$–$C_{20}$ is a heterocyclic or aromatic cyclic, bicyclic, or multicyclic ring system that is unsubstituted or substituted with 1–20 electron-withdrawing groups and/or one or more $C_1$–$C_{10}$ alkyl groups.

28. The compound according to claim 26, wherein each Z is S and each Q is CN.

29. The compound according to claim 26, wherein Q is a 6-carbon ring unsubstituted or substituted with one or more halide atoms.

30. The compound according to claim 26, wherein each Z is oxygen and each Q is $C_6F_5$.

31. Use of a catalyst according to claim 14, for catalyzing an olefin metathesis reaction.

32. The compound according to claim 1, wherein the compound is selected from the group consisting of:

Ru(OC$_6$F$_5$)$_2$(CHPh)(3-Br-py)(IMes);
Ru(OC$_6$Cl$_5$)Cl(CHPh)(IMes)(py);
Ru(OC$_6$Br$_5$)Cl(CHPh)(py)(IMes);
Ru(OC$_6$Br$_5$)Cl(CHPh)(Br-py)(IMes);
Ru(SCN)$_2$(CHPh)(py)(IMes);
Ru(SC$_6$F$_5$)$_2$(CHPh)(IMes)(py);
Ru(CHPh)(3,5-CF$_3$—OC$_6$H$_3$)$_2$(IMes)(py; and
Ru(O$_2$C$_{20}$H$_4$F$_8$)(CHPh)(IMes)(py).

* * * * *